US012570736B2

(12) United States Patent
Crowe et al.

(10) Patent No.: US 12,570,736 B2
(45) Date of Patent: *Mar. 10, 2026

(54) COMPOSITIONS

(71) Applicant: SORRISO PHARMACEUTICALS, INC., San Diego, CA (US)

(72) Inventors: Scott Crowe, Cambridge (GB); Mike West, Cambridge (GB); Kevin Roberts, Cambridge (GB); Tim Carlton, Cambridge (GB); Luana Maggiore, Cambridge (GB); Marion Cubitt, Cambridge (GB); Lurdes Duarte, Cambridge (GB); Keith Ray, Cambridge (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 1106 days.

This patent is subject to a terminal disclaimer.

(21) Appl. No.: 17/620,036

(22) PCT Filed: Jun. 19, 2020

(86) PCT No.: PCT/GB2020/051497
§ 371 (c)(1),
(2) Date: Dec. 16, 2021

(87) PCT Pub. No.: WO2020/254828
PCT Pub. Date: Dec. 24, 2020

(65) Prior Publication Data
US 2023/0143091 A1 May 11, 2023

(30) Foreign Application Priority Data

Jun. 21, 2019 (EP) .................................... 19181869

(51) Int. Cl.
| | |
|---|---|
| *C07K 16/28* | (2006.01) |
| *A61P 1/00* | (2006.01) |
| *A61P 29/00* | (2006.01) |
| *C07K 16/24* | (2006.01) |

(52) U.S. Cl.
CPC .............. *C07K 16/241* (2013.01); *A61P 1/00* (2018.01); *A61P 29/00* (2018.01); *C07K 16/2866* (2013.01); *C07K 2317/569* (2013.01); *C07K 2317/76* (2013.01); *C07K 2317/92* (2013.01); *C07K 2319/50* (2013.01)

(58) Field of Classification Search
CPC .......................... C07K 16/241; C07K 16/2866
See application file for complete search history.

(56) References Cited

U.S. PATENT DOCUMENTS

| | | |
|---|---|---|
| 3,300,077 A | 1/1967 | David et al. |
| 5,512,459 A | 4/1996 | Wagner et al. |
| 5,780,028 A | 7/1998 | Graham |

| | | |
|---|---|---|
| 7,442,159 B1 | 10/2008 | Riechmann et al. |
| 8,399,188 B2 | 3/2013 | Zhao et al. |
| 8,697,654 B2 | 4/2014 | Cheng et al. |
| 9,080,157 B2 | 7/2015 | Convents et al. |
| 9,527,925 B2 | 12/2016 | Gschwind et al. |
| 9,932,412 B2 | 4/2018 | Kim et al. |
| 10,633,438 B2 | 4/2020 | Crowe et al. |
| 10,772,839 B2 | 9/2020 | Crowe et al. |
| 10,980,748 B2 | 4/2021 | Crowe et al. |
| 11,623,952 B2 | 4/2023 | Crowe et al. |
| 11,667,719 B2 | 6/2023 | Crowe et al. |
| 12,173,054 B2 | 12/2024 | Crowe et al. |
| 12,234,279 B2 | 2/2025 | Crowe et al. |
| 12,247,079 B2 | 3/2025 | Crowe et al. |
| 2004/0041867 A1 | 3/2004 | Lapstun et al. |
| 2005/0147612 A1 | 7/2005 | Yayon et al. |
| 2006/0034833 A1 | 2/2006 | Beirnaert |
| 2006/0034845 A1 | 2/2006 | Silence et al. |
| 2006/0057197 A1 | 3/2006 | Han et al. |
| 2006/0138181 A1 | 6/2006 | Thom et al. |
| 2007/0020267 A1 | 1/2007 | Fuh et al. |
| 2007/0042399 A1 | 2/2007 | Wright et al. |
| 2007/0077249 A1 | 4/2007 | Silence et al. |
| 2007/0178082 A1 | 8/2007 | Silence et al. |
| 2007/0237769 A1 | 10/2007 | Silence et al. |
| 2008/0026820 A1 | 1/2008 | Okada |
| 2008/0031770 A1 | 2/2008 | Heselton et al. |
| 2008/0039761 A1 | 2/2008 | Heaton et al. |
| 2008/0122965 A1 | 5/2008 | Fang |
| 2008/0145420 A1 | 6/2008 | Simon |
| 2008/0149143 A1 | 6/2008 | Chou et al. |
| 2008/0260738 A1 | 10/2008 | Moore et al. |
| 2008/0260820 A1 | 10/2008 | Borrelly et al. |
| 2009/0064457 A1 | 3/2009 | Brustle |

(Continued)

FOREIGN PATENT DOCUMENTS

| | | |
|---|---|---|
| AU | 2014214850. A1 | 8/2015 |
| CA | 2817265 A1 | 10/2004 |
| CN | 1809383 A | 7/2006 |
| CN | 101128182 A | 2/2008 |
| CN | 102090373 A | 6/2011 |
| CN | 102388069 A | 3/2012 |
| CN | 102971341 A | 3/2013 |
| CN | 103703129 A | 4/2014 |
| CN | 106715471 A | 5/2017 |

(Continued)

OTHER PUBLICATIONS

Burkovitz et al. Large-scale analysis of somatic hypermutations in antibodies reveals which structural regions, positions and amino acids are modified to improve affinity. FEBS 281(1):306-319 (2014).

(Continued)

*Primary Examiner* — Mark Halvorson

(74) *Attorney, Agent, or Firm* — WILSON SONSINI GOODRICH & ROSATI

(57) ABSTRACT

There is provided inter alia a composition comprising a TNF-alpha binding polypeptide and an IL-7R binding polypeptide.

22 Claims, 12 Drawing Sheets

Specification includes a Sequence Listing.

(56) References Cited

U.S. PATENT DOCUMENTS

| | | |
|---|---|---|
| 2009/0064460 A1 | 3/2009 | Tang et al. |
| 2010/0077422 A1 | 3/2010 | Bushinsky |
| 2010/0137213 A1 | 6/2010 | Fernandez et al. |
| 2010/0239682 A1 | 9/2010 | Andremont et al. |
| 2010/0260857 A1 | 10/2010 | Fallon et al. |
| 2011/0028695 A1 | 2/2011 | Revets et al. |
| 2011/0098518 A1 | 4/2011 | Minoux et al. |
| 2011/0109365 A1 | 5/2011 | Mai |
| 2011/0112229 A1 | 5/2011 | Nagaoka et al. |
| 2011/0229476 A1 | 9/2011 | Liu et al. |
| 2012/0130872 A1 | 5/2012 | Baughman et al. |
| 2012/0151199 A1 | 6/2012 | Shriver |
| 2013/0173687 A1 | 7/2013 | Tuchman et al. |
| 2014/0030049 A1 | 1/2014 | Imai et al. |
| 2014/0044730 A1 | 2/2014 | Yancopoulos et al. |
| 2014/0141152 A1 | 5/2014 | Sostek et al. |
| 2014/0170212 A1 | 6/2014 | Ortenzi et al. |
| 2014/0186365 A1 | 7/2014 | Robinson et al. |
| 2014/0294826 A1 | 10/2014 | Shoemaker |
| 2014/0377287 A1 | 12/2014 | Govindan et al. |
| 2015/0017183 A1 | 1/2015 | Seidah et al. |
| 2015/0058173 A1 | 2/2015 | Schmeling et al. |
| 2015/0147318 A1 | 5/2015 | Bergeron et al. |
| 2015/0176031 A1 | 6/2015 | Streffer |
| 2015/0337035 A1 | 11/2015 | Anderson et al. |
| 2016/0060338 A1 | 3/2016 | Barrett et al. |
| 2016/0156465 A1 | 6/2016 | Vaikuntanathan et al. |
| 2016/0264659 A1 | 9/2016 | Heavner et al. |
| 2017/0002069 A1 | 1/2017 | Crowe et al. |
| 2017/0022271 A1 | 1/2017 | Hoffman et al. |
| 2017/0260266 A1 | 9/2017 | Ahmed et al. |
| 2018/0009881 A1 | 1/2018 | Crowe et al. |
| 2018/0037639 A1 | 2/2018 | Crowe et al. |
| 2018/0100008 A1 | 4/2018 | Crowe et al. |
| 2018/0100009 A1 | 4/2018 | Crowe et al. |
| 2019/0008778 A1 | 1/2019 | Crowe et al. |
| 2019/0040156 A1 | 2/2019 | Demarest et al. |
| 2019/0092855 A1 | 3/2019 | Crowe et al. |
| 2019/0137495 A1 | 5/2019 | Shaked et al. |
| 2019/0307891 A1 | 10/2019 | Crowe et al. |
| 2020/0079844 A1 | 3/2020 | Beirnaert |
| 2020/0317769 A1 | 10/2020 | Crowe et al. |
| 2021/0198345 A1 | 7/2021 | Crowe et al. |
| 2021/0317195 A1 | 10/2021 | Crowe et al. |
| 2022/0242945 A1 | 8/2022 | Crowe et al. |
| 2023/0056445 A1 | 2/2023 | Crowe et al. |
| 2023/0287098 A1 | 9/2023 | Crowe et al. |
| 2024/0277864 A1 | 8/2024 | Crowe et al. |
| 2025/0277043 A1 | 9/2025 | Crowe et al. |

FOREIGN PATENT DOCUMENTS

| | | | |
|---|---|---|---|
| EP | 2275443 A1 | 1/2011 | |
| EP | 2275443 B1 | 12/2015 | |
| EP | 2955196 A1 | 12/2015 | |
| WO | WO-9102078 A1 | 2/1991 | |
| WO | WO-9201047 A1 | 1/1992 | |
| WO | WO-9300077 A1 | 1/1993 | |
| WO | WO-9404678 A1 | 3/1994 | |
| WO | WO-9425591 A1 | 11/1994 | |
| WO | WO-9508562 A1 | 3/1995 | |
| WO | WO-9634103 A1 | 10/1996 | |
| WO | WO-9923221 A2 | 5/1999 | |
| WO | WO-0212502 A2 | 2/2002 | |
| WO | WO-0248382 A2 | 6/2002 | |
| WO | WO-03035694 A2 | 5/2003 | |
| WO | WO-2004009776 A2 | 1/2004 | |
| WO | WO-2004037205 A2 | 5/2004 | |
| WO | WO-2004041862 A2 | 5/2004 | |
| WO | WO-2004041863 A2 | 5/2004 | |
| WO | WO-2004041865 A2 | 5/2004 | |
| WO | WO-2004041867 A2 | 5/2004 | |
| WO | WO-2006056306 A2 | 6/2006 | |
| WO | WO-2006071877 A2 | 7/2006 | |
| WO | WO-2006122786 A2 | 11/2006 | |
| WO | WO-2006122787 A1 | 11/2006 | |
| WO | WO-2006138181 A2 | 12/2006 | |
| WO | WO-2007005955 A2 | 1/2007 | |
| WO | WO-2007025977 A2 | 3/2007 | |
| WO | WO-2007027714 A2 | 3/2007 | |
| WO | WO-2007048022 A2 | 4/2007 | |
| WO | WO-2007070948 A1 | 6/2007 | |
| WO | WO-2007104529 A2 | 9/2007 | |
| WO | WO-2008020079 A1 | 2/2008 | |
| WO | WO-2008031770 A2 | 3/2008 | |
| WO | WO-2008039761 A2 | 4/2008 | |
| WO | WO-2008049897 A1 | 5/2008 | |
| WO | WO-2008074840 A2 | 6/2008 | |
| WO | WO-2008101985 A2 | 8/2008 | |
| WO | WO-2008101985 A3 | 10/2008 | |
| WO | WO-2008122965 A2 | 10/2008 | |
| WO | WO-2008124170 A2 | 10/2008 | |
| WO | WO-2008144753 A2 | 11/2008 | |
| WO | WO-2008124170 A3 | 12/2008 | |
| WO | WO-2008149143 A2 | 12/2008 | |
| WO | WO-2009021754 A2 | 2/2009 | |
| WO | WO-2008149143 A3 | 4/2009 | |
| WO | WO-2009046168 A1 | 4/2009 | |
| WO | WO-2009064457 A2 | 5/2009 | |
| WO | WO-2009064460 A2 | 5/2009 | |
| WO | WO-2009068627 A2 | 6/2009 | |
| WO | WO-2009147248 A2 | 12/2009 | |
| WO | WO-2010020811 A1 | 2/2010 | |
| WO | WO-2010045506 A2 | 4/2010 | |
| WO | WO-2010056550 A1 | 5/2010 | |
| WO | WO-2010045506 A3 | 7/2010 | |
| WO | WO-2010077422 A2 | 7/2010 | |
| WO | WO-2010085643 A1 | 7/2010 | |
| WO | WO-2010115998 A2 | 10/2010 | |
| WO | WO-2011009365 A1 | 1/2011 | |
| WO | WO-2011083175 A1 | 7/2011 | |
| WO | WO-2011094259 A2 | 8/2011 | |
| WO | WO-2011098518 A2 | 8/2011 | |
| WO | WO-2011104687 A1 | 9/2011 | |
| WO | WO-2011112229 A2 | 9/2011 | |
| WO | WO-2011135026 A1 | 11/2011 | |
| WO | WO-2011135040 A1 | 11/2011 | |
| WO | WO-2011139269 A1 | 11/2011 | |
| WO | WO-2011139629 A2 | 11/2011 | |
| WO | WO-2012007880 A2 | 1/2012 | |
| WO | WO-2011139629 A3 | 4/2012 | |
| WO | WO-2012055030 A1 | 5/2012 | |
| WO | WO-2012078878 A2 | 6/2012 | |
| WO | WO-2012130872 A1 | 10/2012 | |
| WO | WO-2012131053 A1 | 10/2012 | |
| WO | WO-2012151199 A1 | 11/2012 | |
| WO | WO-2012175741 A2 | 12/2012 | |
| WO | WO-2013024059 A2 | 2/2013 | |
| WO | WO-2013056984 A1 | 4/2013 | |
| WO | WO-2013058833 A1 | 4/2013 | |
| WO | WO-2013064701 A2 | 5/2013 | |
| WO | WO-2013087857 A2 | 6/2013 | |
| WO | WO-2013087874 A1 | 6/2013 | |
| WO | WO-2013091103 A1 | 6/2013 | |
| WO | WO-2013173687 A1 | 11/2013 | |
| WO | WO-2013184871 A1 | 12/2013 | |
| WO | WO-2014030049 A2 | 2/2014 | |
| WO | WO-2014058875 A3 | 6/2014 | |
| WO | WO-2014141152 A2 | 9/2014 | |
| WO | WO-2015009996 A1 | 1/2015 | |
| WO | WO-2015058173 A1 | 4/2015 | |
| WO | WO-2015065987 A1 | 5/2015 | |
| WO | WO-2015100409 A2 | 7/2015 | |
| WO | WO-2015144852 A1 | 10/2015 | |
| WO | WO-2015176031 A2 | 11/2015 | |
| WO | WO-2015189302 A1 | 12/2015 | |
| WO | WO-2016065323 A2 | 4/2016 | |
| WO | WO-2016103093 A1 | 6/2016 | |
| WO | WO-2016156465 A1 | 10/2016 | |
| WO | WO-2016156466 A1 | 10/2016 | |
| WO | WO-2016162537 A1 | 10/2016 | |
| WO | WO-2016202411 A1 | 12/2016 | |
| WO | WO-2016202414 A1 | 12/2016 | |
| WO | WO-2016202415 A1 | 12/2016 | |

(56)        References Cited

FOREIGN PATENT DOCUMENTS

WO    WO-2018060453 A1    4/2018
WO    WO-2018104483 A1    6/2018
WO    WO-2020254826 A1    12/2020
WO    WO-2020254827 A1    12/2020
WO    WO-2020254828 A1    12/2020

OTHER PUBLICATIONS

Clark et al. Trends in antibody sequence changes during the somatic hypermutation process. J Immunol 177(1):333-340 (2006).

Julian et al. Efficient affinity maturation of antibody variable domains requires co-selection of compensatory mutations to maintain thermodynamic stability. Sci Rep 7:45259 (2017).

Lu et al. Immune Modulation by Human Secreted RNases at the Extracellular Space. Front Immunol 9:1012 (2018).

Murphy et al. Enhancing recombinant antibody performance by optimally engineering its format. J Immunol Methods 463:127-133 (2018).

Murtaugh et al. A combinatorial histidine scanning library approach to engineer highly pH-dependent protein switches. Protein Sci 20(9):1619-1631 (2011).

U.S. Appl. No. 16/950,758 Office Action dated Oct. 23, 2023.

U.S. Appl. No. 17/196,498 Office Action dated Jul. 19, 2023.

U.S. Appl. No. 17/698,823 Office Action dated Nov. 7, 2023.

Wallace et al. Immunopathology of inflammatory bowel disease. World J Gastroenterol 20(1):6-21 (2014).

Yusakul et al. Effect of linker length between variable domains of single chain variable fragment antibody against daidzin on its reactivity. Biosci Biotechnol Biochem 80(7):1306-1312 (2016).

Gustot et al. Profile of soluble cytokine receptors in Crohn's disease. Gut. 54(4):488-495 (2005).

Katoh et al. MAFFT multiple sequence alignment software version 7: improvements in performance and usability. Mol Biol Evol. 30(4):772-780 (2013).

Koh et al. Generation of a family-specific phage library of llama single chain antibody fragments that neutralize HIV-1. Journal of Biological Chemistry 285(25):19116-19124 (2010).

Merchlinsky et al. Construction of an infectious molecular clone of the autonomous parvovirus minute virus of mice. Journal of Virology 47(1):227-232 (1983).

Nelson et al. Monoclonal antibodies. Mol Pathol. 53(3):111-117 (2000).

Reimund et al. Increased production of tumour necrosis factor-alpha interleukin-1 beta, and interleukin-6 by morphologically normal intestinal biopsies from patients with Crohn's disease. Gut 39(5):684-689 (1996).

Reimund et al. Mucosal inflammatory cytokine production by intestinal biopsies in patients with ulcerative colitis and Crohn's disease. Journal of Clinical Immunology 16(3):144-150 (1996).

Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).

U.S. Appl. No. 16/950,758 Office Action dated Feb. 29, 2024.

U.S. Appl. No. 17/196,498 Office Action dated Dec. 14, 2023.

U.S. Appl. No. 17/196,498 Office Action dated Jun. 7, 2024.

Barata et al. Flip the coin: IL-7 and IL-7R in health and disease. Nat Immunol 20(12):1584-1593 (2019).

Casset et al. A peptide mimetic of an anti-CD4 monoclonal antibody by rational design. Biochemical and Biophysical Research Communication 307:198-205 (2003).

Chen et al. Enhancement and destruction of antibody function U by somatic mutation: unequal occurrence is controlled by V gene combinatorial associations. The EMBO Journal 14(12):2784-2794 (1995).

Lee et al. Anti-IL-7 receptor-a reverses established type 1 diabetes in nonobese diabetic mice by modulating effector T-cell function. PNAS USA 109(31):12674-12679 (2012).

Maccallum et al.: Antibody-antigen interactions: contact analysis and binding site topography. J Mol Biol. 262(5):732-745 (1996).

Marković et al. Modulation of Signaling Mediated by TSLP and IL-7 in Inflammation, Autoimmune Diseases, and Cancer. Front Immunol 11:1557 (2020).

U.S. Appl. No. 16/821,287 Office Action dated Oct. 21, 2022.

U.S. Appl. No. 17/752,710 Office Action dated Nov. 4, 2022.

2005 Drug Bank Data (https://wwwdrugbank.caldrugs/DB00085) for Pancrelipase.

Arbabi-Ghahroudi et al.: Selection and identification of single domain antibody fragments from camel heavy-chain antibodies. FEBS Letters 414(3):521-526 (1997).

Baumgart et al.: Crohn's disease. Lancet 380(9853):1590-1605 (2012).

Bendig. Humanization of Rodent Monoclonal Antibodies by CDR Grafting. Methods a Companion to Methods in Enzymology 8:83-93 (1995).

Biancheri et al. Differential Cleavage of Anti-Tumor Necrosis Factor-Alpha Agents by Matrix Metalloproteinase (MMP)-10 and MMP-12 In Inflammatory Bowel Disease. ECCO, Abstract, 1 page, Dublin (2011).

Biancheri et al.: Proteolytic cleavage and loss of function of biologic agents that neutralize tumor necrosis factor in the mucosa of patients with inflammatory bowel disease. Gastroenterology 149(6):1564-1574 (2015).

Binz et al.: Designing repeat proteins: well-expressed, soluble and stable proteins from combinatorial libraries of consensus ankyrin repeat proteins. J. Mol. Biology 332(2):489-503 (2003).

Bjerkan et al. Multiple Functions of the New Cytokine-Based Antimicrobial Peptide Thymic Stromal Lymphopoietin (TSLP). Pharmaceuticals (Basel) 9(3):E41 (2016).

Blattler et al. New heterobifunctional protein crosslinking reagent that forms an acid-labile link. Biochemistry 24(6):1517-1524 (1985).

Bruno et al.: Basics and recent advances in peptide and protein drug delivery. Ther Deliv. 4(11):1443-1467 (2013).

Caldas et al. Humanization of the anti-CD18 antibody 6.7: an unexpected effect of a framework residue in binding to antigen. Mol Immunol. 39(15):941-952 (2003).

Chen et al. Fusion Protein Linkers: Property, Design and Functionality. Adv Drug Deliv Rev 65:1357-1369 (2013). Available online Sep. 29, 2012.

Chomczynski, et al. Single-step method of RNA isolation by acid guanidinium thiocyanate-phenol-chloroform extraction. Anal Biochem. Apr. 1987;162(1):156-9.

Cianferoni et al. Eosinophilic Esophagitis and Gastroenteritis. Curr Allergy Asthma Rep. 15(9):58 (2015).

Colman et al., Effects of amino acid sequence changes on antibody-antigen interactions, Research in Immunology, 1994; 145(1):33-36.

Colombel et al. Adalimumab for maintenance of clinical response and remission in patients with Crohn's disease: the CHARM trial. Gastroenterology 132:52-65 (2007).

Coppieters et al.: Formatted anti-tumor necrosis factor alpha VHH proteins derived from camelids show superior potency and targeting to inflamed joints in a murine model of collagen-induced arthritis. Arthritis Rheum 54(6):1856-1866 (2006).

Corren et al. Tezepelumab in Adults with Uncontrolled Asthma. N Engl J Med. 377(10):936-946 (2017).

Crawley et al. Soluble IL-7R alpha (sCD127) inhibits IL-7 activity and is increased in HIV infection. J Immunol. 184(9):4679-4687 (2010).

Crowe et al.: Gastrointestinal Stability and Tissue Penetration of V565: a Novel Orally Administered Anti-TNFa VorabodyTM. Poster from 10th Annual Proteins and Antibodies Congress [1] (2017).

Crowe et al.: Gastrointestinal Stability and Tissue Penetration of V565: A Novel Orally Administered Anti-TNFa VorabodyTm. Vhsquared, Poster from PEGS Europe Protein and Antibody Engineering Summit, Lisbon, Portugal [1] (2017).

Crowe et al.: Oral Delivery of a Novel Engineered Anti TNFa Domain Antibody (VorabodyTM) for the Treatment of Intestinal Bowel Disease. PEGS Europe Protein & Antibody Engineering Summit [1] (2017).

Crowe et al.: Preclinical Assessment of a Novel Anti-TNFa VorabodyTM as an Oral Therapy for Crohn's Disease. 18th International Congress of Mucosal Immunology, Washington D.C. [1] (2017).

(56)             References Cited

OTHER PUBLICATIONS

Crowe et al: Preclinical Development of a Novel, Orally-Administered Anti-Tumour Necrosis Factor Domain Antibody for the Treatment of Inflammatory Bowel Disease. Scientific Reports 8:4941 [1-13] (2018).

Croxford et al. IL-23: one cytokine in control of autoimmunity. Eur J Immunol. 42:2263-2273 (2012).

Danese: New therapies for inflammatory bowel disease: from the bench to the bedside. Gut 61(6):918-932 (2012).

Deschacht et al.: A novel promiscuous class of camelid single-domain antibody contributes to the antigen-binding repertoire. J. Immmunol 184(10):5696-5704 (2010).

Desmet et al. Structural basis of IL-23 antagonism by an Alphabody protein scaffold. Nature Communications 5:5237 (2014).

Desmyter et al.: Neutralization of Human Interleukin 23 by Multivalent Nanobodies Explained by the Structure of Cytokine-Nanobody Complex. Front Immunol. 8:884 (2017).

Dooms. Interleukin-7: Fuel for the autoimmune attack. J Autoimmun. 45:40-48 (2013).

Ebersbach et al.: Affilin-novel binding molecules based on human gamma-B-crystallin, an all beta-sheet protein. J. Molecular Biology 372(1):172-185 (2007).

Eken et al. Interleukin 23 in Crohn's disease. Inflamm Bowel Dis. 20:587-595 (2014).

Ellis et al. Anti-IL-7 receptor α monoclonal antibody (GSK2618960) in healthy subjects—a randomized, double-blind, placebo-controlled study. Br J Clin Pharmacol. 85(2):304-315 (2019).

Fadda et al.: Physiological bicarbonate buffers: stabilisation and use as dissolution media for modified release systems. Int. J. Pharm. 382(1-2):56-60 (2009).

Faisst et al.: Isolation of a fully infectious variant of parvovirus H-1 supplanting the standard strain in human cells. Journal of Virology 69(7):4538-4543 (1995).

Fields et al. Dual-attribute continuous monitoring of cell proliferation/cytotoxicity. Am Biotechnol Lab 11(4):48-50 (1993).

Fornasa et al. Dichotomy of short and long thymic stromal lymphopoietin isoforms in inflammatory disorders of the bowel and skin. J Allergy Clin Immunol. 136(2):413-422 (2015).

Frenken et al. Isolation of antigen specific llama VHH antibody fragments and their high level secretion by *Saccharomyces cerevisiae*. J Biotechnol 78(1):11-21 (2000).

Fry et al. Interleukin-7: from bench to clinic. Blood 99(11):3892-3904 (2002).

Fry et al. The many faces of IL-7: from lymphopoiesis to peripheral T cell maintenance. J Immunol. 174(11):6571-6576 (2005).

Furfaro et al. IL-23 Blockade for Crohn's disease: next generation of anti-cytokine therapy. Expert Rev Clin Immunol. 13:457-467 (2017).

Garbacz et al.: A dynamic system for the simulation of fasting luminal pH-gradients using hydrogen carbonate buffers for dissolution testing of ionisable compounds. Eur J Pharm Sci. 51:224-231 (2014).

Giusti et al. Somatic diversification of S107 from an antiphosphocholine to an anti-DNA autoantibody is due to a single base change in its heavy chain variable region. PNAS USA 84(9):2926-30 (1987).

Goldberg et al.: Engineering a targeted delivery platform using Centyrins. Protein Eng Des Sel. 29(12):563-572 (2016).

Goldberg et al. The unusual suspects—innate lymphoid cells as novel therapeutic targets in IBD. Nat Rev Gastroenterol Hepatol (5):271-283 (2015).

Gomes et al., Comparison of yeasts as hosts for recombinant protein production. Microorganisms 6(2):38 [1-23] (2018).

Goyanes et al.: Gastrointestinal release behaviour of modified-release drug products: dynamic dissolution testing of mesalazine formulations. Int. J. Pharm. 484(1-2):103-108 (2015).

Grabulovski et al. A novel, non-immunogenic Fyn SH3-derived binding protein with tumor vascular targeting properties. J Biol Chem. 282(5):3196-3204 (2007).

Griffiths et al.: Shark Variable New Antigen Receptor (VNAR) Single Domain Antibody Fragments: Stability and Diagnostic Applications. Antibodies 2(1):66-81 (2013).

Grundstrom et al.: Oligonucleotide-directed mutagenesis by microscale 'shot-gun' gene synthesis. Nucleic Acids Research 13(9):3305-3316 (1985).

Guerra et al.: Management of inflammatory bowel disease in poor responders to infliximab. Clin Exp Gastroenterol 7:359-367 (2014).

Hafler et al. Risk alleles for multiple sclerosis identified by a genomewide study. N Engl J Med. 357(9):851-862 (2007).

Hamers-Casterman et al. Naturally occurring antibodies devoid of light chains. Nature 363(6428):446-8 (1993).

Hanauer et al. Human anti-tumor necrosis factor monoclonal antibody (adalimumab) in Crohn's disease: the CLASSIC-I trial. Gastroenterology 130:323-333 (2006).

Hanauer et al, Maintenance infliximab for Crohn's disease: the ACCENT I randomized trial. Lancet 359:1541-1549 (2002).

Harmsen et al.: Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).

Harmsen et al. Properties, production, and applications of camelid single-domain antibody fragments. Appl. Microbiol. Biotechnol. 77:13-22 (2007).

Harmsen et al.: Selection and Optimization of Proteolytically Stable Llama Single-Domain Antibody Fragments for Oral Immunotherapy. Applied Microbiology and Biotechnology 72(3):544-551 (2006).

Hashimoto et al.: Effects of signal sequences on the secretion of hen lysozyme by yeast: construction of four secretion cassette vectors. Protein Engineering 11(2):75-77 (1998).

Hendrickson et al.: Clinical aspects and pathophysiology of inflammatory bowel disease. Clinical Microbiology Reviews 15(1):79-94 (2002).

Henikoff et al. Amino acid substitution matrices from protein blocks. PNAS USA 89(22):10915-10919 (1992) .

Heninger et al. IL-7 abrogates suppressive activity of human CD4+CD25+FOXP3+ regulatory T cells and allows expansion of alloreactive and autoreactive T cells. J Immunol. 189(12):5649-5658 (2012).

Hoefman et al.: Pre-Clinical Intravenous Serum Pharmacokinetics of Albumin Binding and Non-Half-Life Extended Nanobodies(R). Antibodies 4(3):141-156 (2015).

Hoogenboom et al. Multi-subunit proteins on the surface of filamentous phage: methodologies for displaying antibody (Fab) heavy and light chains. Nucleic Acids Res. 19(15):4133-4137 (1991).

Horwitz et al.: Secretion of functional antibody and Fab fragment from yeast cells. Proc. Natl. Acad. Sci. U.S.A. 85(22):8678-8682 (1988).

Hu et al., A phylogenomic approach to reconstructing the diversification of serine proteases in fungi. J Evol Biol. 17(6):1204-1214 (2004).

Humphreys et al.: Modes of L929 cell death induced by TNF-alpha and other cytotoxic agents. Cytokine 11(10):773-782 (1999).

Huse et al. Generation of a large combinatorial library of the immunoglobulin repertoire in phage lambda. Science 246(4935):1275-1281 (1989).

Hussack et al: A V(L) single-domain antibody library shows a high-propensity to yield non-aggregating binders. Protein Eng Des Sel. 25(6):313-318 (2012).

Hussack et al. Chapter 14: Isolation and characterization of Clostridium difficile toxin-specific single-domain antibodies. Methods Mol Biol. 911:211-239 (2012).

Hussack et al. Engineered Single-Domain Antibodies with High Protease Resistance and Thermal Stability. PLoS One. 6(11):e28218 (2011).

Hussack et al.: Neutralization of Clostridium difficile toxin A with single-domain antibodies targeting the cell receptor binding domain. J. Biol. Chem. 286(11):8961-8976 (2011).

Hussack et al.: Protease-resistant single-domain antibodies inhibit Campylobacter jejuni motility. Protein Eng Des Sel. 27(6):191-198 (2014).

(56)                    References Cited

OTHER PUBLICATIONS

Hussack et al.: Single-domain Antibody Inhibitors of Clostridium difficile Toxins. Thesis submitted to the Faculty of Graduate and Postdoctoral Studies, Dept. of Biochemistry, Microbiology and Immunology [1-227] (2011).

Hussack: Single-domain Antibody Inhibitors of Clostridium difficule Toxins. Universite d'Ottawa website [1-3] https://ruor.uottawa.ca/handle/10393/20362 (2013).

Hussan et al. A review on recent advances ofenteric coating. IOSR J Pharm 2(6):5-11 (2012).

Johnson et al.: Sensitive affimer and antibody based impedimetric label-free assays for c-reactive protein. Analytical Chemistry 84(15):6553-6560 (2012).

Jones et al.: Targeted localized use of therapeutic antibodies: a review of non-systemic, topical and oral applications. Crit Rev Biotechnol 36(3):506-520 (2015).

Kabat et al. Sequences of proteins of immunological interest. NIH Publ. No. 91-3242 1:647-669 (1991).

Kamm et al.: Practical application of anti-TNF therapy for luminal Crohn's disease. Inflammatory Bowel Diseases. 17(11):2366-2391 (2011).

Karlin, et al. Applications and statistics for multiple high-scoring segments in molecular sequences. PNAS USA 90:5873-5877 (1993).

Khantasup et al. Design and Generation of Humanized Single-chain Fv Derived from Mouse Hybridoma for Potential Targeting Application. Monoclon Antib Immunodiagn Immunother. 34(6):404-17 (2015).

Kim et al. A Dual Target-directed Agent against Interleukin-6 Receptor and Tumor Necrosis Factor α ameliorates experimental arthritis. Scientific Reports 6:20150 (2015).

Kim et al.: Antibody light chain variable domains and their biophysically improved versions for human immunotherapy. Mabs. 6(1):219-235 (2014).

Knezevic et al. Quantitation of affinity, avidity, and binding kinetics of protein analytes with a dynamically switchable biosurface. J Am Chem Soc 134(37):15225-15228 (2012).

Kohler et al. Continuous cultures of fused cells secreting antibody of predefined specificity. Nature256(5517):495-497 (1975).

Koide et al. Monobodies: antibody mimics based on the scaffold of the fibronectin type III domain. Methods in Molecular Biology 352:95-111 (2007).

Krehenbrink et al.: Artificial binding proteins (Affitins) as probes for conformational changes in secretin PulD. J Mol Biol. 383(5):1058-1068 (2008).

Ling et al.: Approaches to DNA Mutagenesis: An Overview. Analytical Biochemistry 254(2):157-178 (1997).

Lipovsek: Adnectins: engineered target-binding protein therapeutics. Protein Engineering, Design & Selection 24(1-2):3-9 (2011).

Liu et al. Crucial role of interleukin-7 in T helper type 17 survival and expansion in autoimmune disease. Nat Med. 16(2):191-197 (2010) (retraction in: Nat Med. 2013 19(12):1673).

Liu et al.: Targeting TNF-alpha with a tetravalent mini-antibody TNF-TeAb. Biochemical Journal 406(2):237-246 (2007).

Liu. Thymic stromal lymphopoietin: master switch for allergic inflammation. J Exp Med 203(2):269-273 (2006).

Lopes et al.: Mechanism of high-copy-No. integration of pMIRY-type vectors into the ribosomal DNA of *Saccharomyces cerevisiae*. Gene. 105(1):83-90 (1991).

McCoy et al.: Neutralisation of HIV-1 cell-cell spread by human and llama antibodies. Retrovirology 11:83 doi: 10.1186/s12977-014-0083-y [1-15] (2014).

McGovern et al. The IL23 axis plays a key role in the pathogenesis of IBD. Gut 56:1333-1336 (2007).

Merchant et al.: Predicting the gastrointestinal behaviour of modified-release products: utility of a novel dynamic dissolution test apparatus involving the use of bicarbonate buffers. Int. J. Pharm. 475(1-2):585-591 (2014).

Merchlinksy et al.: Construction of an infectious molecular clone of the autonomous parvovirus minute virus of mice. Journal of Virology 47(1):227-232 (1983).

Michael. The role of digestive enzymes in orally induced immune tolerance. Immunol Invest. 18(9-10):1049-1054 (1989) (Abstract).

Miethe et al.: Production of Single Chain Fragment Variable (scFv) Antibodies in *Escherichia coli* Using the LEX TM Bioreactor. Journal of Biotechnology 163(2):105-111 (2012).

Molhoj et al. CD19-/CD3-bispecific antibody of the BiTE class is far superior to tandem diabody with respect to redirected tumor cell lysis. Mol Immunol. 44(8):1935-43 (2007).

Muszewska et al., Fungal lifestyle reflected in serine protease repertoire. Sci Rep. 7(1):9147 [1-12] (2017).

Muyldermans. Nanobodies: natural single-domain antibodies. Annu Rev Biochem 82:775-797 (2013).

Muyldermans et al. Sequence and structure of VH domain from naturally occurring camel heavy chain immunoglobulins lacking light chains. Protein Engineering 7(9):1129-1133 (1994).

Nambiar, et al. Total synthesis and cloning of a gene coding for the ribonuclease S protein. Science 223(4642):1299-301 (1984).

Nelson et al.: Nonoclonal antibodies. Molecular Pathology 53(3):111-117 (2000).

Nguyen et al. Functional heavy-chain antibodies in Camelidae. Adv Immunol 79:261-296 (2001).

Nixon et al. Engineered protein inhibitors of proteases. Curr Opin Drug Discov Devel. 9(2):261-268 (2006).

Nogi et al.: Nucleotide sequence of the transcriptional initiation region of the yeast GAL7 gene. Nucleic Acid Research 11(24):8555-8568 (1983).

Noti et al. Thymic stromal lymphopoietin-elicited basophil responses promote eosinophilic esophagitis. Nat Med. 19(8):1005-1013 (2013).

Nurbhai et al.: Measured and Modelled Data Suggest That Oral Administration of V565, A Novel Domain Antibody to TNF-alpha, Could Be Beneficial in the Treatment of IBD. 13th Congress of ECCO, Vienna, Austria, 1 page (2018).

Nurbhai et al.: Oral Anti-Tumour Necrosis Factor Domain Antibody V565 Provides High Intestinal Concentrations, and Reduces Markers of Inflammation in Ulcerative Colitis Patients. Sci Rep. 9(1):14042 (2019).

Nygren. Alternative binding proteins: affibody binding proteins developed from a small three-helix bundle scaffold. FEBS J. 275(11):2668-2676 (2008).

Ordas et al.: Anti-TNF monoclonal antibodies in inflammatory bowel disease: pharmacokinetics-based dosing paradigms. Clin Pharmacol Ther. 91(4):635-646 (2012).

Ortonne. Recent developments in the understanding of the pathogenesis of psoriasis. British Journal of Dermatology 140(Suppl 54):1-7 (1999).

Padlan. Anatomy of the Antibody Molecule. Mol Immunol 31(3):169-217 (1994).

Patnaik et al. Penicillin fermentation: mechanisms and models for industrial-scale bioreactors. Crit Rev Biotechnol 20:1-15 (2015).

Paul. Fundamental Immunology. 3rd Edition, pp. 292-295, Raven Press (1993).

PCT/EP2016/057021 International Search Report and Written Opinion dated Aug. 8, 2016.

PCT/EP2016/057022 International Search Report and Written Opinion dated Jun. 14, 2016.

PCT/EP2016/057024 International Search Report and Written Opinion dated Jun. 16, 2016.

PCT/EP2016/057032 International Search Report and Written Opinion dated Aug. 4, 2016.

PCT/EP2016/057034 International Search Report and Written Opinion dated Aug. 3, 2016.

PCT/EP2017/057775 International Search Report and Written Opinion dated Jul. 7, 2017.

PCT/GB2020/051495 International Search Report and Written Opinion dated Sep. 30, 2020.

PCT/GB2020/051496 International Search Report and Written Opinion dated Oct. 20, 2020.

PCT/GB2020/051497 International Search Report and Written Opinion dated Sep. 17, 2020.

PCT/MT2017/000001 International Search Report and Written Opinion dated Oct. 20, 2017.

Peters et al. Innate lymphoid cells in inflammatory bowel diseases. Immunol Lett. 172:124-131 (2015).

(56)         References Cited

OTHER PUBLICATIONS

Rimoldi et al. Intestinal immune homeostasis is regulated by the crosstalk between epithelial cells and dendritic cells. Nat Immunol. 6(5):507-514 (2005).

Robinson et al.: A Protease-Resistant Oral Domain Antibody to TNFa Delivers High Concentrations of Active Compound in Ileal Fluid of Subjects with an Ileostomy. 25th United European Gastroenterology Week, Barcelona, Spain [1] (2017).

Rose et al. Identification and biochemical characterization of human plasma soluble IL-7R: lower concentrations in HIV-1-infected patients. J Immunol. 182(12):7389-7397 (2009).

Rose-John: IL-6 trans-signaling via the soluble IL-6 receptor: importance for the pro-inflammatory activities of IL-6. Int. J. Biol. Sci. 8(9):1237-1247 (2012).

Roux et al.: Structural analysis of the nurse shark (new) antigen receptor (NAR): molecular convergence of NAR and unusual mammalian immunoglobulins. PNAS USA 95(20):11804-11809 (1998).

Rudikoff et al. Single amino acid substitution altering antigen-binding Specificity. PNAS USA 79:1979-1983 (1982).

Saerens et al. Identification of a universal VHH framework to graft non-canonical antigen-binding loops of camel single-domain antibodies. J Mol Biol. 352(3):597-607 (2005).

Sakmar et al.: Total synthesis and expression of a gene for the alpha-subunit of bovine rod outer segment guanine nucleotide-binding protein (transducin). Nucleic Acids Research 16(14A):6361-6372 (1988).

Sandborn et al. Certolizumab pegol for the treatment of Crohn's disease. N Engl J Med. 357:228-238 (2007).

Schreiber et al. Maintenance therapy with certolizumab pegol for Crohn's disease. N Engl J Med. 357:239-250 (2007).

Shaji, et al. Protein and Peptide drug delivery: oral approaches. Indian J Pharm Sci. May-Jun. 70(3):269-77 (2008).

Shealy et al.: Characterization of golimumab, a human monoclonal antibody specific for human tumor necrosis factor a. MAbs 2(4):428-439 (2010).

Silverman et al., Multivalent avimer proteins evolved by exon shuffling of a family of human receptor domains. Nat. Biotechnol. 23 (12):1556-1561 (2005).

Siontorou: Nanobodies as novel agents for disease diagnosis and therapy. Int J Nanomedicine 8:4215-4227 (2013).

Skerra: Alternative binding proteins: anticalins—harnessing the structural plasticity of the lipocalin ligand pocket to engineer novel binding activities. FEBS J. 275(11):2677-2683 (2008).

Skerra et al. Assembly of a functional Immunoglobulin Fv fragment in *Escherichia coli*. Science 240(4855):1038-1041 (1988).

STIC report (2019).

Suderman et al.: Development of polyol-responsive antibody mimetics for single-step protein purification. Protein Expr Purif. 134:114-124 (2017).

Tal et al.: Interleukin 7 and thymic stromal lymphopoietin: from immunity to leukemia. Cell Mol Life Sci. 71(3):365-378 (2014).

Tanha et al.: Selection by phage display of llama conventional V(H) fragments with heavy chain antibody V(H)H properties. Journal of Immunological Methods 263(1-2):97-109 (2002).

Teng et al. IL-12 and IL-23 cytokines: from discovery to targeted therapies for immune-mediated inflammatory diseases. Nat Med. 21:719-729 (2015).

Teutsch et al. Identification of 11 novel and common single nucleotide polymorphisms in the interleukin-7 receptor-alpha gene and their associations with multiple sclerosis. Eur J Hum Genet. 11(7):509-515 (2003).

Thomassen et al.: Large-scale production of VHH antibody fragments by *Saccharomyces cerevisiae*. Enzyme and Microbial Technology 30(3):273-278 (2002).

Tsilingiri et al. Thymic Stromal Lymphopoietin: To Cut a Long Story Short. Cell Mol Gastroenterol Hepatol. 3(2):174-182 (2017).

Ungar et al.: Optimizing Anti-TNF-a Therapy: Serum Levels of Infliximab and Adalimumab Are Associated With Mucosal Healing in Patients With Inflammatory Bowel Diseases. Clin Gastroenterol Hepatol. 14(4):550-557 (2016).

Unger et al.: Selection of nanobodies that block the enzymatic and cytotoxic activities of the binary Clostridium difficile toxin CDT. Scientific Reports 5:7850 [1-10] (2015).

UniProt Database: Uncharacterized protein. Accession No. B5H131, 2 pages (2008) http://www.uniprot.org/uniprot/B5H131.

U.S. Appl. No. 15/273,353 Office Action dated Aug. 16, 2018.

U.S. Appl. No. 15/273,353 Office Action dated Jan. 23, 2018.

U.S. Appl. No. 15/273,353 Office Action dated Jun. 4, 2019.

U.S. Appl. No. 15/717,174 Office Action dated Apr. 22, 2020.

U.S. Appl. No. 15/717,174 Office Action dated Aug. 8, 2019.

U.S. Appl. No. 15/717,174 Office Action dated Mar. 6, 2019.

U.S. Appl. No. 15/717,174 Office Action dated Sep. 16, 2020.

U.S. Appl. No. 15/717,230 Office Action dated Jan. 21, 2020.

U.S. Appl. No. 15/717,230 Office Action dated May 18, 2020.

U.S. Appl. No. 15/717,230 Office Action dated Sep. 3, 2019.

U.S. Appl. No. 16/140,843 Office Action dated Nov. 26, 2019.

U.S. Appl. No. 16/988,506 Office Action dated Oct. 6, 2020.

Van Schie et al.: The antibody response against human and chimeric anti-TNF therapeutic antibodies primarily targets the TNF binding region. Ann Rheum Dis. 74(1):311-314 (2015).

Vandenbroucke et al. Orally administered L. lactis secreting an anti-TNF nanobody demonstrate efficacy in chronic colitis. Mucosal Immunology 3(1):49-56 (2010).

Vandeventer: Anti-TNF antibody treatment of Crohn's disease. Ann Rheum Dis. 58(Suppl I):1114-1120 (1999).

Verma et al. Modified oligonucleotides: synthesis and strategy for users. Annu Rev Biochem 67:99-134 (1998).

Verstraete et al. Structure and antagonism of the receptor complex mediated by human TSLP in allergy and asthma. Nat Commun. 8:14937 (2017).

Vetter et al. Emerging oral targeted therapies in inflammatory bowel diseases: opportunities and challenges. Therap Adv Gastroenterol. 10(10):773-790 (2017).

Vincke et al. General strategy to humanize a camelid single-domain antibody and identification of a universal humanized nanobody scaffold. J. Biol. Chem. 284(5):3273-3284 (2009).

Volkel et al.: Optimized linker sequences for the expression of monomeric and dimeric bispecific single-chain diabodies. Protein Eng. 14(10):815-823 (2001).

Vossenkamper et al.: A CD3-specific antibody reduces cytokine production and alters phosphoprotein profiles in intestinal tissues from patients with inflammatory bowel disease. Gastroenterology 147(1):172-183 (2014).

Vu et al.: Comparison of llama VH sequences from conventional and heavy chain antibodies. Molecular Immunology 34(16-17):1121-1131 (1997).

Wahlich et al.: Oral Delivery of a Novel Domain Antibody (VorabodyTM) for the Treatment of Chron's Disease. PEGS Europe Protein & Antibody Engineering Summit, Lisbon, Portugal, 1 page (2017).

Walsh. Structural insights into the common γ-chain family of cytokines and receptors from the interleukin-7 pathway. Immunol Rev. 250(1):303-316 (2012).

Ward et al. Binding activities of a repertoire of single immunoglobulin variable domains secreted from *Escherichia coli*. Nature 341(6242):544-546 (1989).

Wells et al. Cassette mutagenesis: an efficient method for generation of multiple mutations at defined sites. Gene 34:315-323 (1985).

West et al.: Predicting intestinal tract luminal concentrations after oral dosing of an anti-TNFa domain antibody engineered for intestinal protease resistance. VHsquared Antibody Engineering & Therapeutics Meeting, San Diego, USA, 1 page (2017).

Winkler et al. Changing the antigen binding specificity by single point mutations of an anti-p24 (HIV-1) antibody. J Immunol. 165(8):4505-4514 (2000).

Yan et al. Construction of a synthetic phage-displayed Nanobody library with CDR3 regions randomized by trinucleotide cassettes for diagnostic applications. Journal of Translational Medicine 12:343 (2014).

(56)　　　　　References Cited

OTHER PUBLICATIONS

Yu et al., Interaction between Bevacizumab and Murine VEGF-A: A Reassessment. Investigative Ophthalmology & Visual Science 49(2):522-527 (2008).

Zabetakis et al. Contributions of the complementarity determining regions to the thermal stability of a single-domain antibody. PLoS One 8(10):e77678 (2013).

Analysis methods: Gene correlation networks (GCNs) generate disease-relevant transcriptional modules to enable systems-level analysis (Presentation abstract) Presented at the Johnson and Johnson Innovative medicine. p. 1. Retrieved on May 9, 2025.

Colombel, Jean-Frédéric. et al. Adalimumab for maintenance of clinical response and remission in patients with Crohn's disease: the CHARM trial. Gastroenterology 132(1):52-65 (2007).

Differentially Expressed Genes at Week 12 compared with baseline pre-treatment, 2022: [retrieved on May 9, 2024]. Available at URL:https://prociromme.ueq.eu/week2022/#/details/presentations/767 p. 1.

Endoscopic, Histologic and molecular changes are observed as early as week 4 with COMBO compared with monotherapy (Presentation abstract) Presented at the Johnson and Johnson Innovative medicine. p. 1. Retrieved on May 9, 2025.

Key Single cell-derived transcriptional modules identified IL-22 as a Mechanistic link to epithelial Inflammation (Presentation abstract) Presented at the Johnson and Johnson Innovative medicine. p. 1. Retrieved on May 9, 2025.

Key Single cell-derived transcriptional modules were identified as proximal markers of the IL-23 pathway and patient response (Presentation abstract) Presented at the Johnson and Johnson Innovative medicine. p. 1. Retrieved on May 9, 2025.

Richards, D. et al. Abstract DOP54: Guselkumab and golimumab combination induction therapy in Ulcerative Colitis results in early local tissue healing that is sustained through guselkumab maintenance therapy. Journal of Crohn's and Colitis 18(Supplement_1):i171-i172 (2024).

Richards, Dylan. et al. DOP54: Guselkumab and golimumab combination induction therapy in Ulcerative Colitis results in early local tissue healing that is sustained through guselkumab maintenance therapy (Presentation) Presented at the Janssen Research and development. pp. 1-7. Retrieved on May 9, 2025.

UEG Week 2022 Oral Presentations. United European Gastroenterology 10(Suppl8):144-145 (2022).

U.S. Appl. No. 17/620,030 Ex Parte Quayle Action dated Aug. 2, 2024.

Co-pending U.S. Appl. No. 19/025,399, inventors Crowe; Scott et al., filed Jan. 16, 2025.

U.S. Appl. No. 17/620,026 Office Action dated Jun. 4, 2025.

Williams, Andrew. *Sun Pharmaceutical Industries, Ltd.* v. *Eli Lilly & Co.* (Fed. Cir. 2010). Patent Docs, Jul. 29, 2010; [retrieved on Jun. 11, 2025]. Available at URL: https://www.patentdocs.org/2010/07/sun-pharmaceutical-industries-ltd-v-eli-lilly-co-fed-cir-2010.html pp. 1-3.

Figure 12

Survival at 4 hours in human faecal supernatant

COMPOSITIONS

CROSS-REFERENCE TO RELATED APPLICATIONS

This application is a U.S. National Entry Application of International Application No. PCT/GB2020/051497, filed internationally on Jun. 19, 2020, which claims the benefit of European Application No. 19181869.9, filed on Jun. 21, 2019, all of which are incorporated by reference in their entireties.

SEQUENCE LISTING

The content of the ASCII text file of the sequence listing named Sorriso_60790-711_831_Sequence_Listing_08-19-2022.txt, which is 25,172 bytes in size was created on Aug. 19, 2022 and electronically submitted on Aug. 19, 2022, is incorporated herein by reference in its entirety.

FIELD OF THE INVENTION

The present invention relates to compositions and constructs comprising a TNF-alpha binding polypeptide and an IL-7R binding polypeptide. The present invention also relates to nucleic acids encoding such constructs, to methods for preparing such compositions and constructs, to cDNA and vectors comprising nucleic acids encoding such constructs, to host cells expressing or capable of expressing such constructs and to uses of such compositions and constructs.

BACKGROUND OF THE INVENTION

Tumour necrosis factor-alpha is a homotrimeric proinflammatory cytokine involved in systemic inflammation which exists in both soluble and membrane-bound forms. TN F-alpha is secreted predominantly by monocytes and macrophages but is also secreted by tumour cell lines as well as CD4+ and CD8+ peripheral blood T lymphocytes and some cultured T and B cell lines. TNF-alpha has been implicated in inflammatory diseases, autoimmune diseases, viral, bacterial and parasitic infections, malignancies, and/or neurodegenerative diseases and is a target for specific biological therapy in autoimmune/autoinflammatory diseases such as rheumatoid arthritis and Crohn's disease (CD).

Interleukin-7 (IL-7) is produced constitutively by non-haematopoietic stromal and epithelial cells and is essential for the development of T-lymphocytes in the thymus and for the survival and homeostatic regulation of peripheral T cells. In the intestinal mucosa IL-7 also regulates phenotypically and functionally distinct populations of innate lymphoid cells that are important for the initial priming of immune responses to pathogenic microbial challenges as well as CD4+ lymphoid tissue inducer (LTi) cells, which have the capacity to promote lymphoid tissue organogenesis and some dendritic cell populations. The functional effects of IL-7 on T cells makes IL-7 a critical enhancer of protective immunity, as well as of autoimmunity and inflammation. The effects of IL-7 on different target cells are mediated through the IL-7R, a heterodimeric complex that includes the IL-7Ra subunit (CD127) and the common cytokine receptor gamma chain (γc) (CD132). The IL-7Ra is not only available in the cell-membrane-bound format, but also as a soluble form (sIL-7Ra). In addition to the roles played by the IL-7/IL-7Ra in human T cell development and homeostasis, preclinical studies have demonstrated the involvement of the IL-7/IL-7Ra pathway in animal models of different autoimmune and inflammatory diseases.

TSLP is a cytokine which seems to be involved in the regulation of inflammatory processes at mucosal surfaces of the body. TSLP stimulates dendritic cells (DCs) and innate lymphoid cells (ILCs) to induce the secretion of Th2 cytokines (IL-4, IL-5 and IL-13) and promotes the development of Th2-type inflammation. TSLP is now thought to underlie the development of some allergic disorders including atopic dermatitis, rhinitis and also promote intestinal disorders including eosinophilic oesophagitis (EoE) and ulcerative colitis (UC). Paradoxically, TSLP was also reported to be important for the maintenance of immune homeostasis and mucosal protection in the gastrointestinal tract. Recently, the discovery that TSLP can be expressed as two different isoforms has provided a biological explanation for the apparently contrasting activities of this cytokine (Fornasa et al 2015; Tsilingiri et al 2017). Molecular studies have shown that the TSLP gene can give rise to two coding RNAs that are regulated by two different promoter regions. One of the transcripts encodes a long isoform of TSLP (L-TSLP) of 159aa (UNIPROT entry Q969D9, SEQ ID NO: 22) and the second transcript a short form of TSLP (S-TSLP) that encompasses the C-terminal 63aa of L-TSLP (UNIPROT entry Q969D9-2, SEQ ID NO: 23). L-TSLP acts on target cells via a receptor complex that includes a TSLP-specific receptor chain (TSLPR) and the IL-7Ra chain. Recently, structural studies have shown that interactions of IL-7 and L-TSLP with the IL-7Ra chain of the TSLP-receptor complex involve a common IL-7Ra binding site (Verstraete et al 2017). S-TSLP does not bind to the TSLPR and it is not capable of inhibiting the binding of L-TSLP to this receptor. To the best of the author's knowledge, a specific receptor for S-TSLP has not been identified to date. Importantly, it has been shown that S-TSLP is expressed preferentially by healthy skin and in healthy intestinal mucosal tissue by epithelial and lamina propria cells. S-TSLP has anti-inflammatory activity; in vitro S-TSLP inhibits the production of pro-inflammatory cytokines by monocyte derived DCs and contributes to the conditioning of CD103+ DCs to a tolerogenic phenotype.

TNF-alpha, IL-7 and L-TSLP are all therefore cytokines that regulate cell types and pathways involved in the development and maintenance of intestinal inflammation in IBD. Anti-TNF-alpha antibodies have transformed the treatment of Crohn's disease and ulcerative colitis. However, approximately one-third of patients prescribed an anti-TNF-alpha agent are primary non-responders. Among the primary responders, subsequent loss of response may vary between 10 and 50% per year (secondary non-response). Patients with a primary non-response are unlikely to benefit from switching to a second anti-TNF-alpha agent; consequently, new effective therapies are needed, to better address the unmet clinical needs in these patients. Currently, the efficacy of IL-7R blocking antibodies has not been tested in patients with intestinal inflammatory diseases. However, preclinical studies have demonstrated that the short-term systemic administration of IL-7R-blocking antibodies can be an effective treatment in models of gastrointestinal inflammation. In the murine IBD models the primary mechanism for efficacy following IL-7R-antagonist treatment involves the local depletion or functional inhibition of pathogenic T cells (IL-7R+ effector/memory T cells) that express moderate to high levels of the IL-7Ra and are activated due to increased production of IL-7 in inflamed intestinal tissue. Inhibition of the IL-7/IL-7R pathway represents a novel strategy to address proinflammatory T cells by a mechanism that is distinct from that involved in the action of TNF-alpha neutralising antibodies. Compositions or constructs that successfully combine the effects of anti-TNF-alpha and anti-IL-7R antibodies therefore have potential for improved efficacy and/or efficacy in a wider group of patients with IBD.

WO2004041862, WO2006122786 and Coppieters et al 2006 (herein incorporated by reference in their entirety) disclose single domain antibodies directed against TNF-alpha and related aspects. WO2013056984, WO2015189302, WO2011094259 and WO2011104687 (herein incorporated by reference in their entirety) disclose antibodies directed against IL-7R and related aspects.

Compositions or constructs of the present invention may, in at least some embodiments, have one or more of the following advantages compared to substances of the prior art. These advantages may be realised by each of the component polypeptides in a composition of the invention in their own right, or alternatively the combination of the polypeptides in a composition of the invention may result in an additive or even synergistic effect in respect of one or more of the below advantages.

(a) increased affinity and/or avidity for TNF-alpha and/or IL-7R;

(b) increased neutralising capability against TNF-alpha and/or IL-7R;

(c) increased inhibition of phosphorylation of signalling proteins;

(d) increased inhibition of cytokine production;

(e) reduced immunogenicity, for example when administered to a mouse, cynomolgus monkey or human;

(f) increased stability in the presence of proteases, for example (a) in the presence of proteases found in the small and/or large intestine and/or IBD inflammatory proteases, for example trypsin, chymotrypsin, enterokinase, MMP3, MMP10, MMP12, other MMPs and cathepsin and/or (b) in the presence of proteases such as cell membrane-attached proteases, secreted proteases and proteases released on cell lysis from gut commensal microflora and/or pathogenic bacteria, found in the small and/or large intestine;

(g) increased stability to protease degradation during production (for example resistance to yeast proteases);

(h) increased suitability for oral administration;

(i) increased suitability for local delivery to the intestinal tract and lamina propria following oral administration;

(j) increased suitability for expression in a heterologous host such as bacteria (e.g. *Escherichia coli*) or a yeast (e.g. *Saccharomyces cerevisiae* or *Pichia pastoris*);

(k) suitability for, and improved properties for, use in a pharmaceutical;

(l) suitability for, and improved properties for, use in a functional food;

(m) improved tissue penetration such as penetration of inflamed colonic mucosal epithelium and submucosal tissues to access the sub mucosal lamina propria;

(n) decreased immunogenicity in humans for example due to increased sequence similarity to human immunoglobulins;

(o) more effective prevention or treatment of autoimmune disease and/or inflammatory disease, including amelioration of the symptoms thereof, including in particular inflammatory bowel disease and/or mucositis, particularly when administered orally; and (p) binding to novel epitopes.

SUMMARY OF THE INVENTION

The present inventors have provided surprisingly effective compositions and constructs comprising a TNF-alpha binding polypeptide and an IL-7R binding polypeptide. In particular, it has been found that the provision of a TNF-alpha binding polypeptide and an IL-7R binding polypeptide in a single composition may be more effective than the provision of each binding polypeptide separately. In some embodiments, the combination of these polypeptides in compositions of the invention may have an additive effect and in further embodiments, the combination of these polypeptides in compositions of the invention may have a synergistic effect.

Based on the findings disclosed herein using ex vivo cultured intestinal mucosal tissue from inflammatory bowel disease patients (Examples 4 and 5) it may be expected that these compositions have particular utility in the prevention or treatment of autoimmune and or inflammatory disease. More specifically, the findings disclosed herein indicate that these compositions may have particular utility in the prevention or treatment of inflammatory bowel disease (for example Crohn's disease, ulcerative colitis or check-point inhibitor induced colitis), or in the prevention or treatment of mucositis or oesophagitis, particularly when administered orally.

It may be expected that the same benefits may be derived by the use of a TNF-alpha binding polypeptide in the treatment or prevention of disease, together with an IL-7R binding polypeptide, wherein the polypeptides are not combined in the same composition. Similarly, it may be expected that the same benefits may be derived by the use of an IL-7R binding polypeptide in the treatment or prevention of disease, together with a TNF-alpha binding polypeptide, wherein the polypeptides are not combined in the same composition.

The present invention provides a composition comprising a TNF-alpha binding polypeptide and an IL-7R binding polypeptide.

Also provided is a construct comprising a TNF-alpha binding polypeptide and an IL-7R binding polypeptide, and a polynucleotide encoding said construct.

Also provided is a TNF-alpha binding polypeptide for use in the treatment or prevention of an autoimmune disease and/or inflammatory disease, together with an IL-7R binding polypeptide; and an IL-7R binding polypeptide for use in the treatment or prevention of an autoimmune disease and/or inflammatory disease, together with a TNF-alpha binding polypeptide.

The specific TNF-alpha binding polypeptide and some of the data disclosed herein are also disclosed in PCT application number WO/2016/156465 (which is incorporated herein by reference in its entirety, particularly in so far as the application relates to the TNF-alpha binding polypeptide ID-38F).

DESCRIPTION OF THE SEQUENCES

Figure 1:
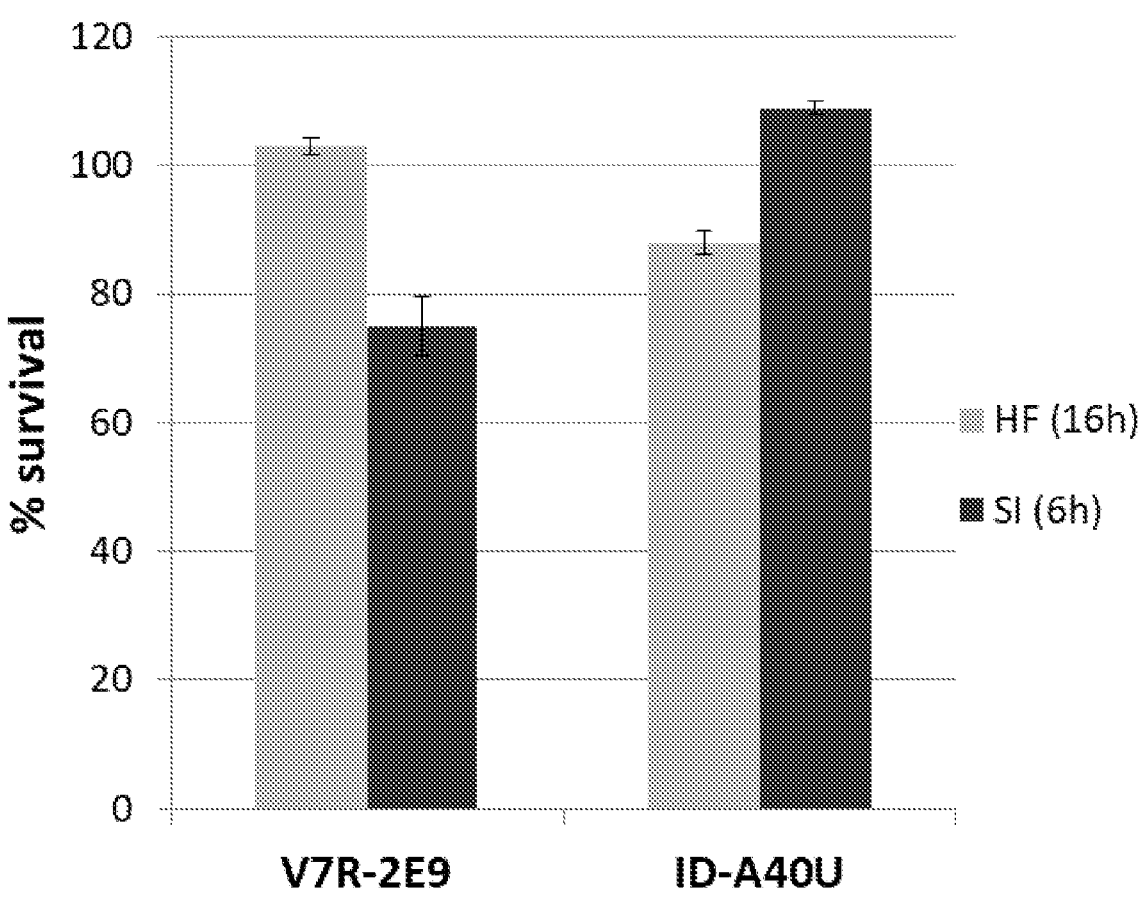
FIG. 1—% survival of V7R-2E9 and ID-A40U in gastrointestinal extracts

SEQ ID NO: 1—Polypeptide sequence of CDR1 of ID-38F

SEQ ID NO: 2—Polypeptide sequence of CDR2 of ID-38F

SEQ ID NO: 3—Polypeptide sequence of CDR3 of ID-38F

SEQ ID NO: 4—Polypeptide sequence of FR1 of ID-38F

SEQ ID NO: 5—Polypeptide sequence of FR2 of ID-38F

SEQ ID NO: 6—Polypeptide sequence of FR3 of ID-38F

SEQ ID NO: 7—Polypeptide sequence of FR4 of ID-38F

SEQ ID NO: 8—Polypeptide sequence of ID-38F

SEQ ID NO: 9—Polypeptide sequence of CDR1 of ID-A62U

SEQ ID NO: 10—Polypeptide sequence of CDR2 of ID-A62U

SEQ ID NO: 11—Polypeptide sequence of CDR3 of ID-A62U

SEQ ID NO: 12—Polypeptide sequence of FR1 of ID-A62U

SEQ ID NO: 13—Polypeptide sequence of FR2 of ID-A62U

SEQ ID NO: 14—Polypeptide sequence of FR3 of ID-A62U

SEQ ID NO: 15—Polypeptide sequence of FR4 of ID-A62U

SEQ ID NO: 16—Polypeptide sequence of ID-A62U

SEQ ID NO: 17—Polynucleotide sequence encoding ID-38F (including two stop codons)

SEQ ID NO: 18—Polynucleotide sequence encoding ID-A62U (including two stop codons)

SEQ ID NO: 19—Polypeptide sequence of enterokinase cleavage site

SEQ ID NO: 20—Polypeptide sequence comprising enterokinase cleavage site

SEQ ID NO: 21—Polypeptide sequence of specific labile linker used in FU3K

SEQ ID NO: 22—Polypeptide sequence of L-TSLP

SEQ ID NO: 23—Polypeptide sequence of S-TSLP

SEQ ID NO: 24—Polypeptide sequence of ID-A40U

SEQ ID NO: 25—Polypeptide sequence of V7R-2E9

SEQ ID NO: 26—Polypeptide sequence of FU3K bihead

SEQ ID NO: 27—Polynucleotide sequence encoding FU3K bihead

SEQ ID NO: 28—Polypeptide sequence of CDR1 with an optional conservative substitution at residue 1 of SEQ ID NO: 9

SEQ ID NO: 29—Polypeptide sequence of CDR2 with optional conservative substitutions at residues 2, 3, 7, 12 and 16 of SEQ ID NO: 10

SEQ ID NO: 30—Polypeptide sequence of CDR3 with optional conservative substitutions at residues 3 and 9 of SEQ ID NO: 11

SEQ ID NO: 31—Polypeptide sequence of a non-protease-labile peptide linker format SEQ ID NO: 32—Polypeptide sequence of a trypsin protease-labile peptide linker format SEQ ID NO: 33—Polypeptide sequence of a trypsin protease-labile peptide linker format SEQ ID NO: 34—Polypeptide sequence of a second trypsin protease-labile peptide linker format SEQ ID NO: 35—Polypeptide sequence of example trypsin protease-labile peptide linker SEQ ID NO: 36—Polypeptide sequence of example trypsin protease-labile peptide linker SEQ ID NO: 37—Polypeptide sequence of example trypsin protease-labile peptide linker SEQ ID NO: 38—Polypeptide sequence of example trypsin protease-labile peptide linker SEQ ID NO: 39—Polypeptide sequence of example trypsin protease-labile peptide linker SEQ ID NO: 40—Polypeptide sequence of example trypsin protease-labile peptide linker SEQ ID NO: 41—Polypeptide sequence of example trypsin protease-labile peptide linker SEQ ID NO: 42—Polypeptide sequence of third trypsin protease-labile peptide linker format SEQ ID NO: 43—Polypeptide sequence of chymotrypsin protease-labile peptide linker format

DETAILED DESCRIPTION OF THE INVENTION

Polypeptides Such as Antibodies and Antibody Fragments Including Immunoglobulin Chain Variable Domains (ICVDs) Such as the VH and VHH Polypeptides are organic polymers consisting of a number of amino acid residues bonded together in a chain. As used herein, 'polypeptide' is used interchangeably with 'protein' and 'peptide'. Polypeptides are said to be binding polypeptides when they contain one or more stretches of amino acid residues which form a binding site, capable of binding to an epitope on a target, with an affinity (suitably expressed as a Kd value, a Ka value, a $K_{on}$-rate and/or a $k_{off}$-rate, as further described herein).

Binding polypeptides include polypeptides such as DARPins (Binz et al. 2003), Affimers™ (Johnson et al 2012), Fynomers™ (Grabulovski et al 2007), Centyrins (Goldberg et al 2016), Affitins (e.g. Nanofitins®, Krehenbrink et al 2008), cyclic peptides, antibodies and antibody fragments. Binding polypeptides also include polypeptides such as Affibodies (Nygren 2008), Affilins (Ebersbach et al. 2007), Alphabodies (Desmet et al 2014), Anticalins (Skerra et al 2008), Avimers (Silverman et al 2005), Kunitz domain peptides (Nixon and Wood 2006), Monobodies (Koide and Koide 2007), nanoCLAMPs (Suderman et al 2017), Adnectins (Lipovsek 2011) and bicyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains ('ICVDs').

The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991 Sequences of Proteins of Immunological Interest, *Fifth Edition U.S. Department of Health and Human Services*, NIH Publication Number 91-3242, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL.

The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994 *Mol Immunol* 31:169-217).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans et al 2013, Hamers-Casterman et al 1993, Muyldermans et al 1994, herein incorporated by reference in their entirety).

An antibody fragment as used herein refers to a portion of an antibody that specifically binds to a target (e.g. a molecule in which one or more immunoglobulin chains is not full length, but which specifically binds to a target).

Examples of binding fragments encompassed within the term antibody fragment (or 'antigen-binding fragment') include:

(i) a Fab fragment (a monovalent fragment consisting of the VLC, VHC, CL and CH1 domains);

(ii) a F(ab')2 fragment (a bivalent fragment comprising two Fab fragments linked by a disulfide bridge at the hinge region);

(iii) a Fd fragment (consisting of the VHC and CH1 domains);

(iv) a Fv fragment (consisting of the VLC and VHC domains of a single arm of an antibody);

(v) an scFv fragment (consisting of VLC and VHC domains joined, using recombinant methods, by a synthetic linker that enables them to be made as a single protein chain in which the VLC and VHC regions pair to form monovalent molecules);

(vi) a VH (an immunoglobulin chain variable domain consisting of a VHC domain from a conventional 4 chain immunoglobulin (Ward et al 1989);

(vii) a VL (an immunoglobulin chain variable domain consisting of a VLC domain);

(viii) a V-NAR (an immunoglobulin chain variable domain consisting of a VHC domain from chondrichthyes IgNAR (Roux et al 1998 and Griffiths et al 2013, herein incorporated by reference in their entirety)

(ix) a VHH.

The total number of amino acid residues in a VHH or VH may be in the region of 110-140, more suitably 110-120.

The examples provided herein relate to compositions comprising immunoglobulin chain variable domains which bind to TNF-alpha and immunoglobulin chain variable domains which bind to IL-7R. The principles of the invention disclosed herein are, however, equally applicable to any compositions comprising polypeptides which bind to TNF-alpha and polypeptides which bind to IL-7R, such as antibodies and antibody fragments. For example, immunoglobulin chain variable domains may be incorporated into a polypeptide such as a full length antibody. Such an approach is demonstrated by McCoy et al., 2014, who provide an anti-HIV VHH engineered as a fusion with a human Fc region (including hinge, CH2 and CH3 domains), expressed as a dimer construct.

Suitably, the polypeptides of the present invention comprise an immunoglobulin chain variable domain. More suitably, the polypeptides of the present invention consist of immunoglobulin chain variable domains. Suitably, the polypeptides of the present invention are antibodies or antibody fragments. More suitably the polypeptides of the present invention are antibody fragments. Suitably the antibody fragment is a VHH, a VH, a VL, a V-NAR, an scFv, a Fab fragment, or a F(ab')2 fragment. Suitably the antibody fragment is an immunoglobulin chain variable domain (such as a VHH, a VH or a VL). Suitably the antibody fragment is an immunoglobulin heavy chain variable domain. More suitably the antibody fragment is a VHH or VH, and most suitably a VHH.

Specificity, Affinity, Avidity, Potency, Inhibition and Neutralisation

Specificity refers to the number of different targets (such as antigens or antigenic determinants) to which a particular binding polypeptide can bind. The specificity of a binding polypeptide is the ability of the binding polypeptide to recognise a particular target as a unique molecular entity and distinguish it from another.

Affinity, represented by the equilibrium constant for the dissociation of a target from a binding polypeptide (Kd), is a measure of the binding strength between a target and a binding site on a binding polypeptide: the lesser the value of the Kd, the stronger the binding strength between a target and the binding polypeptide (alternatively, the affinity can also be expressed as the affinity constant (Ka), which is 1/Kd). Affinity can be determined by known methods, depending on the specific antigen of interest. Suitably, affinity is determined using a dynamically switchable bio-surface (e.g. "SwitchSENSE®", see Knezevic et al 2012) or by surface plasmon resonance.

Avidity is the measure of the strength of binding between a binding polypeptide and the pertinent target. Avidity is related to both the affinity between a target and its binding site on the binding polypeptide and the number of pertinent binding sites present on the binding polypeptide.

Any Kd value less than $10^{-6}$ M is considered to indicate binding. Specific binding of a binding polypeptide to a target (such as an antigen or antigenic determinant) can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

Potency is a measure of the activity of a therapeutic agent (such as a binding polypeptide) expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target and the quantitative magnitude of this response. The term half maximal effective concentration (EC50) refers to the concentration of a therapeutic agent which causes a response halfway between the baseline and maximum after a specified exposure time. The therapeutic agent may cause inhibition (which may be referred to specifically as half maximal inhibitory concentration, 'IC50') or stimulation. EC50 and IC50 are commonly used, and are used herein, as a measure of potency. EC50 and IC50 are used interchangeably herein in respect of the TNF-alpha binding polypeptides and IL-7R binding polypeptides, due to both binding polypeptides causing inhibition of a target.

Specific assays which are suitable for ascertaining the potency of TNF-alpha binding polypeptides and IL-7R binding polypeptides are detailed below under the headings 'TNF-alpha binding polypeptides' and 'IL-7R binding polypeptides', respectively.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Threonine |
| | Asparagine |
| | Glutamine |
| Negatively charged | Aspartate |
| | Glutamate |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al 1991 Sequences of Proteins of Immunological Interest, Fifth Edition U.S. Department of Health and Human Services, NIH Publication Number 91-3242, herein incorporated by reference in its entirety). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

The Kabat numbering system is applied below to particular TNF-alpha and IL-7R binding polypeptides used in the examples provided herein.

The Kabat numbering system applied to ID-A62U, an IL-7R binding polypeptide

| H1 | H2 | H3 | H4 | H5 | H6 | H7 | H8 | H9 | H10 | H11 | H12 | H13 | H14 | H15 | H16 | H17 | H18 | H19 | H20 | H21 | H22 | H23 | H24 |
|----|----|----|----|----|----|----|----|----|-----|-----|-----|-----|-----|-----|-----|-----|-----|-----|-----|-----|-----|-----|-----|
| D | V | Q | L | V | E | S | G | G | G | L | V | Q | A | G | G | S | L | R | L | S | C | E | S |
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |

| | | | | | CDR-H1 | | | | | | | | | | | | | | |
|-----|-----|-----|-----|-----|-----|-----|-----|-----|-----|-----|-----|-----|-----|-----|-----|-----|-----|-----|-----|
| H25 | H26 | H27 | H28 | H29 | H30 | H31 | H32 | H33 | H34 | H35 | H36 | H37 | H38 | H39 | H40 | H41 | H42 | H43 | H44 |
| S | I | S | T | F | S | S | D | A | M | G | W | F | R | Q | A | P | G | K | E |
| 25 | 26 | 27 | 28 | 29 | 30 | 31 | 32 | 33 | 34 | 35 | 36 | 37 | 38 | 39 | 40 | 41 | 42 | 43 | 44 |

| | | | | | CDR-H2 | | | | | | | | | | | | | | |
|-----|-----|-----|-----|-----|-----|-----|-----|------|-----|-----|-----|-----|-----|-----|-----|-----|-----|-----|
| H45 | H46 | H47 | H48 | H49 | H50 | H51 | H52 | H52A | H53 | H54 | H55 | H56 | H57 | H58 | H59 | H60 | H61 | H62 |
| L | E | F | L | A | A | I | G | W | S | G | A | V | T | H | Y | S | D | S |
| 45 | 46 | 47 | 48 | 49 | 50 | 51 | 52 | 53 | 54 | 55 | 56 | 57 | 58 | 59 | 60 | 61 | 62 | 63 |

| CDR-H2 | | | | | | | | | | | | | | | | | | |
|-----|-----|-----|-----|-----|-----|-----|-----|-----|-----|-----|-----|-----|-----|-----|-----|-----|-----|-----|
| H63 | H64 | H65 | H66 | H67 | H68 | H69 | H70 | H71 | H72 | H73 | H74 | H75 | H76 | H77 | H78 | H79 | H80 | H81 |
| V | K | G | R | F | T | I | S | R | D | N | A | K | N | T | V | Y | L | Q |
| 64 | 65 | 66 | 67 | 68 | 69 | 70 | 71 | 72 | 73 | 74 | 75 | 76 | 77 | 78 | 79 | 80 | 81 | 82 |

| | | | | | | | | | | | | | | | CRD-H3 | | |
|-----|------|------|------|-----|-----|-----|-----|-----|-----|-----|-----|-----|-----|-----|-----|-----|-----|
| H82 | H82A | H82B | H82C | H83 | H84 | H85 | H86 | H87 | H88 | H89 | H90 | H91 | H92 | H93 | H94 | H95 | H96 |
| M | N | S | L | R | A | E | D | T | G | R | Y | Y | C | A | E | D | Y |
| 83 | 84 | 85 | 86 | 87 | 88 | 89 | 90 | 91 | 92 | 93 | 94 | 95 | 96 | 97 | 98 | 99 | 100 |

| | | CRD-H3 | | | | | | | | | | | | | | | |
|-----|-----|-----|------|-------|------|------|------|------|------|------|------|------|------|------|------|------|------|
| H97 | H98 | H99 | H100 | H100A | H101 | H102 | H103 | H104 | H105 | H106 | H107 | H108 | H109 | H110 | H111 | H112 | H113 |
| D | T | D | V | W | Q | Y | W | G | Q | G | T | Q | V | T | V | S | S |
| 101 | 102 | 103 | 104 | 105 | 106 | 107 | 108 | 109 | 110 | 111 | 112 | 113 | 114 | 115 | 116 | 117 | 118 |

Residue numbering from N- to C-terminus is provided in the bottom row. Kabat numbering includes the 'H' prefix and is provided in the second row. CDR1, CDR2 and CDR3 are labelled as 'CDR-H1', 'CDR-H2' and 'CDR-H3', respectively. The residues of each CDR or FR can also be numbered from the N- to the C-terminus of that CDR or FR.

The Kabat numbering system applied to ID-38F, a TNF-alpha binding polypeptide:

| Region | FR1 | FR1 | FR1 | FR1 | FR1 | FR1 | FR1 | FR1 | FR1 | FR1 | FR1 | FR1 | FR1 | FR1 | FR1 |
|--------|-----|-----|-----|-----|-----|-----|-----|-----|-----|-----|-----|-----|-----|-----|-----|
| Residue # | 1 | 2 | 3 | 4 | 5 | 6 | 7 | 8 | 9 | 10 | 11 | 12 | 13 | 14 | 15 |
| ID38F | D | V | Q | L | V | E | S | G | G | G | L | V | Q | P | G |
| Kabat numbering | H1 | H2 | H3 | H4 | H5 | H6 | H7 | H8 | H9 | H10 | H11 | H12 | H13 | H14 | H15 |

-continued

| Region | FR1 | FR1 | FR1 | FR1 | FR1 | FR1 | FR1 | FR1 | FR1 | FR1 | FR1 | FR1 | FR1 | FR1 | FR1 |
|---|---|---|---|---|---|---|---|---|---|---|---|---|---|---|---|
| Residue # | 16 | 17 | 18 | 19 | 20 | 21 | 22 | 23 | 24 | 25 | 26 | 27 | 28 | 29 | 30 |
| ID38F | G | S | L | K | L | S | C | A | A | S | G | F | D | F | S |
| Kabat numbering | H16 | H17 | H18 | H19 | H20 | H21 | H22 | H23 | H24 | H25 | H26 | H27 | H28 | H29 | H30 |

| Region | CDR1 | CDR1 | CDR1 | CDR1 | CDR1 | FR2 | FR2 | FR2 | FR2 | FR2 | FR2 | FR2 | FR2 | FR2 | FR2 |
|---|---|---|---|---|---|---|---|---|---|---|---|---|---|---|---|
| Residue # | 31 | 32 | 33 | 34 | 35 | 36 | 37 | 38 | 39 | 40 | 41 | 42 | 43 | 44 | 45 |
| ID38F | S | H | W | M | Y | W | V | R | Q | A | P | G | K | E | L |
| Kabat numbering | H31 | H32 | H33 | H34 | H35 | H36 | H37 | H38 | H39 | H40 | H41 | H42 | H43 | H44 | H45 |

| Region | FR2 | FR2 | FR2 | FR2 | CDR2 | CDR2 | CDR2 | CDR2 | CDR2 | CDR2 | CDR2 | CDR2 | CDR2 | CDR2 | CDR2 |
|---|---|---|---|---|---|---|---|---|---|---|---|---|---|---|---|
| Residue # | 46 | 47 | 48 | 49 | 50 | 51 | 52 | 53 | 54 | 55 | 56 | 57 | 58 | 59 | 60 |
| ID38F | E | W | L | S | E | I | N | T | N | G | L | I | T | H | Y |
| Kabat numbering | H46 | H47 | H48 | H49 | H50 | H51 | H52 | H52A | H53 | H54 | H55 | H56 | H57 | H58 | H59 |

| Region | CDR2 | CDR2 | CDR2 | CDR2 | CDR2 | CDR2 | FR3 | FR3 | FR3 | FR3 | FR3 | FR3 | FR3 | FR3 | FR3 |
|---|---|---|---|---|---|---|---|---|---|---|---|---|---|---|---|
| Residue # | 61 | 62 | 63 | 64 | 65 | 66 | 67 | 68 | 69 | 70 | 71 | 72 | 73 | 74 | 75 |
| ID38F | G | D | S | V | K | G | R | F | T | V | S | R | N | N | A |
| Kabat numbering | H60 | H61 | H62 | H63 | H64 | H65 | H66 | H67 | H68 | H69 | H70 | H71 | H72 | H73 | H74 |

| Region | FR3 | FR3 | FR3 | FR3 | FR3 | FR3 | FR3 | FR3 | FR3 | FR3 | FR3 | FR3 | FR3 | FR3 | FR3 |
|---|---|---|---|---|---|---|---|---|---|---|---|---|---|---|---|
| Residue # | 76 | 77 | 78 | 79 | 80 | 81 | 82 | 83 | 84 | 85 | 86 | 87 | 88 | 89 | 90 |
| ID38F | A | N | K | M | Y | L | E | L | T | R | L | E | P | E | D |
| Kabat numbering | H75 | H76 | H77 | H78 | H79 | H80 | H81 | H82 | H82A | H82B | H82C | H83 | H84 | H85 | H86 |

| Region | FR3 | FR3 | FR3 | FR3 | FR3 | FR3 | FR3 | FR3 | CDR3 | CDR3 | CDR3 | CDR3 | CDR3 | CDR3 | FR4 |
|---|---|---|---|---|---|---|---|---|---|---|---|---|---|---|---|
| Residue # | 91 | 92 | 93 | 94 | 95 | 96 | 97 | 98 | 99 | 100 | 101 | 102 | 103 | 104 | 105 |
| ID38F | T | A | L | Y | Y | C | A | R | N | Q | H | G | L | N | K |
| Kabat numbering | H87 | H88 | H89 | H90 | H91 | H92 | H93 | H94 | H95 | H96 | H97 | H98 | H101 | H102 | H103 |

| Region | FR4 | FR4 | FR4 | FR4 | FR4 | FR4 | FR4 | FR4 | FR4 | FR4 |
|---|---|---|---|---|---|---|---|---|---|---|
| Residue # | 106 | 107 | 108 | 109 | 110 | 111 | 112 | 113 | 114 | 115 |
| ID38F | G | Q | G | T | Q | V | T | V | S | S |
| Kabat numbering | H104 | H105 | H106 | H107 | H108 | H109 | H110 | H111 | H112 | H113 |

Numbering in the ID-38F figure above with the prefix 'H' is Kabat numbering, while numbering above the amino acid sequence is numbering of amino acids consecutively from N- to C-terminus. The residues of each CDR or FR can also be numbered from the N- to the C-terminus of that CDR or FR.

ID-38F is encoded by the polynucleotide sequence of SEQ ID NO: 17. ID-A62U is encoded by the polynucleotide sequence of SEQ ID NO: 18. Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

TNF-Alpha Binding Polypeptides
Functional Properties

An anti-TNF-alpha polypeptide, a polypeptide which interacts with TNF-alpha, or a polypeptide against TNF-alpha, are all effectively TNF-alpha binding polypeptides. A TNF-alpha binding polypeptide may bind to a linear or conformational epitope on TNF-alpha. Suitably the TNF-alpha binding polypeptide binds to human TNF-alpha.

Suitably, the TNF-alpha binding polypeptide binds to TNF-alpha with an equilibrium dissociation constant (Kd) of $10^{-6}$ M or less, more suitably $10^{-7}$ M or less, more suitably $10^{-8}$ M or less and more suitably $10^{-9}$ M or less.

Suitably the affinity of the TNF-alpha binding polypeptide is determined using a dynamically switchable biosurface (e.g. "SwitchSENSE®", see Knezevic et al 2012).

In one embodiment, the affinity of the TNF-alpha binding polypeptide is established at 25° C. by fusing the TNF-alpha binding polypeptide at its C-terminus to single stranded DNA and coupling the DNA-polypeptide fusion to a gold-electrode coated in the fluorescently-labelled complementary strand of single-stranded DNA, before exposing the chip-bound TNF-alpha binding polypeptide to a 10 kHz electrical current and human TNF-alpha at five different concentrations between 50 pM and 4.5 nM for 600 seconds and observing dissociation for 8 hours by time resolved fluorescence.

Suitably the TNF-alpha binding polypeptide neutralises TNF-alpha. A TNF-alpha-neutralising polypeptide is a polypeptide which defends a cell from the effects of TNF-alpha by, for example, inhibiting the biological effect of TNF-alpha. Conventionally, anti-TNF-alpha therapeutic antibody products have used an L929 murine cell line with a cell death endpoint as a neutralisation assay (Humphreys and Wilson 1999). An L929 assay can be performed to assay the ability of a TNF-alpha binding polypeptide to neutralise the effects of TNF-alpha cytotoxicity by ascertaining the half maximal effective concentration (EC50) of the TNF-alpha binding polypeptide. A detailed protocol for the L929 assay is provided below.

L929 Assay

L929 cells (10000 cells/well) are cultured for 24 h in the presence of soluble TNF-alpha (500 pg/ml) and actinomycin (0.75 ug/mL) together with dilutions of the purified polypeptides. At the end of the experiment cytotoxicity is determined using resazurin. The inhibition of soluble human TNF-induced cytotoxicity of mouse L929 cells is tested to determine TNF-alpha neutralising activity of each polypeptide binding human TNF-alpha.

Materials

L929 cells (10000 cells/well)

Sterile polypropylene 96-well plates

DMEM

Human TNF-alpha concentration: 500 pg/ml

Actinomycin D concentration: 0.75 ug/mL

Purified test polypeptide

Range of dilutions of the purified polypeptide (for example): 300 nM-5 pM (1:3 dilutions)

Human TNF-alpha dose-response curves: 10 ng/mL-0.5 pg/mL incubation times: 22 h

Resazurin cell viability reagent

Method 10000 cells/well in 100 ul are plated on day 0 in 96 wells micro-plates in DMEM complete medium and stored over night at 37 degrees C. and 5% $CO_2$. On day 1 serial dilutions 1:3 (in DMEM+Act.D+TNF) for each purified variable domain are set up (with volumes sufficient for triplicates for each point) starting from a top concentration of 300 nM.

The following controls are added to the plates:

1. DMEM complete+0.75 ug/mL Actinomycin D

2. DMEM complete+0.75 ug/mL Actinomycin D+0.5 ng/mL of h-TNF-alpha

3. DMEM complete+0.01% Triton (only in the plate containing the TNF-alpha dose responses)

4. DMEM complete (only in the plates containing the TNF-alpha dose responses)

The medium is removed from each well of the micro-plates and the cells are incubated with 100 ul of each polypeptide dilution or with 100 ul of the different controls. After 22 h of incubation at 37 degrees C. and 5% $CO_2$, 10 ul of resazurin is added to each well and the cells are incubated for 2 h at 37 degrees C. 50 ul of 3% SDS is subsequently added to each well. The plates are then read using a fluorescence plate reader Ex544 nm/Em590 nm.

Suitably the TNF-alpha binding polypeptide neutralizes human TNF-alpha cytotoxicity in the L929 assay with an EC50 of 100 nM or less, such as 50 nM or less, such as 10 nM or less, such as 5 mM or less, such as 1 nM or less, such as 0.9 nM or less, such as 0.8 nM or less, such as 0.7 nM or less, such as 0.6 nM or less, such as 0.5 nM or less, such as 0.4 nM or less, such as 0.3 nM or less, such as 0.2 nM or less, such as 0.15 nM or less.

The neutralising ability of a TNF-alpha binding polypeptide may also be ascertained by ELISA. Suitably, the TNF-alpha binding polypeptide inhibits binding of human TN F-alpha to TNFR1 in an ELISA assay with an EC50 of 30 nM or less, more suitably 10 nM or less, more suitably 3 nM or less, more suitably 1 nM or less, more suitably 0.6 nM or less, more suitably 0.5 nM or less, more suitably 0.4 nM or less.

Alternatively or in addition, the TNF-alpha binding polypeptide inhibits binding of human TNF-alpha to TNFR2 in an ELISA assay with an EC50 of 2 nM or less, more suitably 1 nM or less, more suitably 0.9 nM or less, more suitably 0.8 nM or less, more suitably 0.7 nM or less, more suitably 0.6 nM or less, more suitably 0.5 nM or less, more suitably 0.4 nM or less.

Suitably the ELISA is carried out as described in Example 2 of WO2018/060453.

In one embodiment, the affinity of the TNF-alpha binding polypeptide is established by coating directly on a Biacore (or equivalent) sensor plate wherein the polypeptide is flowed over the plate to detect binding. Suitably a Biacore T200 plate is used at 25° C. in HBS-EP+ (GE Healthcare) running buffer at 30 ul/min.

Structural Properties

Suitably the TNF-alpha binding polypeptide is a polypeptide comprising an antibody fragment. The polypeptide may be an antibody. Suitably the antibody fragment is selected from the group consisting of: V-NARs, scFvs, Fab fragments, F(ab')2 fragments or immunoglobulin chain variable domains such as VLs, VHHs and VHs. More suitably the antibody fragment is an immunoglobulin chain variable domain, more suitably a VHH or VH, most suitably a VHH.

Suitably the TNF-alpha binding polypeptide comprises three CDRs (CDR1, CDR2 and CDR3).

Suitably CDR1 of the TNF-alpha binding polypeptide comprises or more suitably consists of a sequence sharing 20% or greater, more suitably 40% or greater, more suitably 60% or greater, more suitably 80% or greater sequence identity with SEQ ID NO: 1.

Alternatively, CDR1 of the TNF-alpha binding polypeptide comprises or more suitably consists of a sequence having no more than 3, more suitably no more than 2, more suitably no more than 1 addition(s), substitution(s) and/or deletion(s) compared to SEQ ID NO: 1.

Suitably any residues of CDR1 of the TNF-alpha binding polypeptide differing from their corresponding residues in SEQ ID NO: 1 are conservative substitutions with respect to their corresponding residues. Suitably CDR1 comprises or more suitably consists of SEQ ID NO: 1.

Suitably CDR2 of the TNF-alpha binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 70% or greater, more suitably 75% or greater, more suitably 80% or greater, more suitably 85% or greater, more suitably 90% or greater sequence identity, with SEQ ID NO: 2.

Alternatively, CDR2 of the TN F-alpha binding polypeptide comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s), substitution(s) and/or deletion(s) compared to SEQ ID NO: 2.

Suitably any residues of CDR2 of the TNF-alpha binding polypeptide differing from their corresponding residues in SEQ ID NO: 2 are conservative substitutions with respect to their corresponding residues. Suitably the residue of CDR2 of the TNF-alpha binding polypeptide corresponding to residue number 10 of SEQ ID NO: 2 is R, H, D, E, N, Q, S, T, Y, G, A, V, L, W, P, M, C, F or I (most suitably H). Suitably CDR2 of the TNF-alpha binding polypeptide comprises or more suitably consists of SEQ ID NO: 2.

Suitably CDR3 of the TNF-alpha binding polypeptide comprises or more suitably consists of a sequence sharing 30%, more suitably 50%, more suitably 60%, more suitably 80% or greater sequence identity with SEQ ID NO: 3.

Alternatively, CDR3 of the TN F-alpha binding polypeptide comprises or more suitably consists of a sequence having no more than 3, more suitably no more than 2, more suitably no more than 1 addition(s), substitution(s) and/or deletion(s) compared to SEQ ID NO: 3.

Suitably any residues of CDR3 of the TNF-alpha binding polypeptide differing from their corresponding residues in SEQ ID NO: 3 are conservative substitutions with respect to their corresponding residues. Suitably the residue of CDR3 of the TNF-alpha binding polypeptide corresponding to residue number 3 of SEQ ID NO: 3 is R, H, D, E, N, Q, S, T, Y, G, A, V, L, W, P, M, C, F or I; or suitably R, H, D, E, N, Q, S, T, Y, G, V, L, W, P, M, C, F or I (most suitably H). Suitably the residue of CDR3 of the TNF-alpha binding polypeptide corresponding to residue number 3 of SEQ ID NO: 3 is H and any other residues of CDR3 of the TNF-alpha binding polypeptide differing from their corresponding residues in SEQ ID NO: 3 are conservative substitutions with respect to their corresponding residues. Suitably CDR3 of the TNF-alpha binding polypeptide comprises or more suitably consists of SEQ ID NO: 3.

Alternatively CDR3 of the TNF-alpha binding polypeptide comprises or more suitably consists of a sequence sharing 30%, such as 50%, such as 60%, such as 80% or greater sequence identity with SEQ ID NO: 3 and residue number 3 of CDR3 is R, D, N, C, E, Q, G, H, I, L, K, M, F, P, S, T, W, Y or V (suitably H or a conservative substitution of H; more suitably H). Alternatively residue number 3 of CDR3 is H or a conservative substitution of H (most suitably H) and any other residues of CDR3 differing from their corresponding residues in SEQ ID NO: 3 are conservative substitutions.

Suitably residue 1 of CDR1 of the TN F-alpha binding polypeptide is S, V or N; residues 2 to 4 are HWM and residue 5 is Y or C. Suitably, residues 1 to 9 of CDR2 of the TNF-alpha binding polypeptide are EINTNGLIT; residue 10 is H, K, S or N; residue 11 is Y, residue 12 is G, V, I or A; residue 13 is D; residue 14 is S or F; residue 15 is V or T; residue 16 is H, K, R or G and residue 17 is G. Suitably residue 1 of CDR3 of the TNF-alpha binding polypeptide is N; residue 2 is Q or E; residue 3 is H, K, M or R and residues 4 to 6 are GLN.

Suitably the TNF-alpha binding polypeptide comprises three CDRs (CDR1, CDR2 and CDR3) and four framework regions (FR1-FR4).

Suitably FR1 of the TNF-alpha binding polypeptide comprises or more suitably consists of a sequence sharing 5%, 12%, 18%, 26%, 32%, 38%, 46%, 52%, 58%, 62%, 66%, 68%, 72%, 75%, 78%, 82%, 85%, 90% or 95% or greater sequence identity, with SEQ ID NO: 4.

Suitably any residues of FR1 of the TNF-alpha binding polypeptide differing from their corresponding residues in SEQ ID NO: 4 are conservative substitutions with respect to their corresponding residues. Suitably the residue of FR1 of the TNF-alpha binding polypeptide corresponding to residue number 1 of SEQ ID NO: 4 is G, A, V, L, I, F, P, S, T, Y, C, M, K, R, H, W, D, E or N (more suitably D or E, most suitably D). Suitably the residue of FR1 of the TNF-alpha binding polypeptide corresponding to residue number 5 of SEQ ID NO: 4 is G, A, V, L, I, F, P, S, T, Y, C, M, K, R, H, W, D, E or N (suitably V). Suitably the residues of FR1 of the TNF-alpha binding polypeptide corresponding to residue numbers 1 to 5 of SEQ ID NO: 4 are DVQLV. Suitably the residue of FR1 of the TNF-alpha binding polypeptide corresponding to residue numbers 20 and/or 24 of SEQ ID NO: 4 are an amino acid which is hydrophobic (most suitably L or A, respectively). Suitably the residue of FR1 of the TNF-alpha binding polypeptide corresponding to residue number 29 of SEQ ID NO: 4 is F. Suitably FR1 of the TNF-alpha binding polypeptide comprises or more suitably consists of SEQ ID NO: 4.

Suitably FR2 of the TNF-alpha binding polypeptide comprises or more suitably consists of a sequence sharing 10%, 15%, 25%, 30%, 40%, 45%, 55%, 60%, 70%, 75%, 85% or 90% or greater sequence identity, with SEQ ID NO: 5.

Suitably any residues of FR2 of the TNF-alpha binding polypeptide differing from their corresponding residues in SEQ ID NO: 5 are conservative substitutions with respect to their corresponding residues. Suitably the residues of FR2 of the TNF-alpha binding polypeptide corresponding to residue numbers 8 to 11 of SEQ ID NO: 5 are KEXE, wherein X is R or L. Alternatively the residues of FR2 of the TNF-alpha binding polypeptide corresponding to residue numbers 9 to 12 of SEQ ID NO: 5 are GLEW. Suitably FR2 of the TN F-alpha binding polypeptide comprises or more suitably consists of SEQ ID NO: 5.

Suitably FR3 of the TNF-alpha binding polypeptide comprises or more suitably consists of a sequence sharing 8%, 15%, 20%, 26%, 32%, 40%, 45%, 52%, 58%, 65%, 70%, 76%, 80%, 82%, 85%, 90%, 92% or 95% or greater sequence identity, with SEQ ID NO: 6.

Suitably the residue of FR3 of the TNF-alpha binding polypeptide corresponding to residue number 26 of SEQ ID NO: 6 is an amino acid which is hydrophobic (suitably A). Suitably any residues of FR3 of the TNF-alpha binding polypeptide differing from their corresponding residues in SEQ ID NO: 6 are conservative substitutions with respect to their corresponding residues. Suitably FR3 of the TNF-alpha binding polypeptide comprises or more suitably consists of SEQ ID NO: 6.

Suitably FR4 of the TNF-alpha binding polypeptide comprises or more suitably consists of a sequence sharing 5%, 10%, 20%, 30%, 40%, 50%, 60%, 70%, 80% or 90% or greater sequence identity, with SEQ ID NO: 7.

Suitably any residues of FR4 of the TNF-alpha binding polypeptide differing from their corresponding residues in SEQ ID NO: 7 are conservative substitutions with respect to their corresponding residues. Suitably FR4 of the TNF-alpha binding polypeptide comprises or more suitably consists of SEQ ID NO: 7.

Suitably the TNF-alpha binding polypeptide comprises or more suitably consists of a sequence sharing 50%, 55%, 60%, 65%, 70%, 75%, 80%, 85%, 90%, 95%, 96%, 97%, 98% or 99% or greater sequence identity, with SEQ ID NO: 8. Suitably the N-terminus of the TNF-alpha binding polypeptide is D. Suitably the TNF-alpha binding polypeptide comprises or more suitably consists of SEQ ID NO: 8.

According to a specific embodiment, the TNF-alpha binding polypeptide has an amino acid sequence which is not exactly the same as (i.e. shares 100% sequence identity with) the amino acid sequence of a naturally occurring polypeptide.

IL-7R Binding Polypeptides

Functional Properties

An anti-IL-7R polypeptide, a polypeptide which interacts with IL-7R, or a polypeptide against IL-7R, are all effectively IL-7R binding polypeptides. An IL-7R binding polypeptide may bind to a linear or conformational epitope on IL-7R. Preferably, the IL-7R binding polypeptide binds to IL-7Ra.

Suitably, the IL-7R binding polypeptide will bind to human IL-7R. Suitably the IL-7R binding polypeptide binds to both soluble and membrane-bound IL-7R.

Suitably, the polypeptide of the invention will neutralise IL-7 and/or L-TSLP binding human IL-7R.

Suitably, the polypeptide of the invention will neutralise human IL-7 and/or human L-TSLP binding human IL-7R. More suitably, the polypeptide of the invention will neutralise human IL-7 and/or human L-TSLP binding both human and at least one additional primate IL-7R selected from the group consisting of baboon IL-7R, marmoset IL-7R, cynomolgus IL-7R and rhesus IL-7R. Most suitably, the polypeptide of the invention will neutralise human IL-7 and human L-TSLP binding human IL-7R.

Suitably the IL-7R binding polypeptide is directed against epitopes on IL-7R that lie in and/or form part of the IL-7 binding site(s) of the IL-7R, such that said polypeptide, upon binding to IL-7R, results in inhibiting or reducing signalling mediated by the IL-7R.

An IL-7R binding polypeptide is a neutralising polypeptide for the purposes of the invention if the polypeptide binds to IL-7R (suitably IL-7Ra), inhibiting the binding of IL-7R to IL-7 and/or L-TSLP as measured by ELISA. A specific ELISA method suitable for determining the level of inhibition in this context is detailed in Example 1 below.

Suitably the IL-7R binding polypeptide neutralizes IL-7R binding to IL-7 with an EC50 of 2.00 nM or less, such as 1.50 nM or less, such as 1.00 nM or less, such as 0.90 nM or less, such as 0.80 nM or less, such as 0.70 nM or less, such as 0.65 nM or less, such as 0.60 nM or less, such as 0.55 nM or less, such as 0.50 nM or less, such as 0.45 nM or less, such as 0.4 nM or less, such as 0.35 nM or less, such as 0.30 nM or less. Suitably the EC50 is established using the IL-7/IL-7R neutralisation ELISA detailed in Example 1 below.

Suitably the IL-7R binding polypeptide neutralizes IL-7R-dependent, IL-7-induced STAT5 phosphorylation in human lymphocytes with an EC50 of 100 nM or less, such as 50 nM or less, such as 25 nM or less, such as 10 nM or less, such as 8 nM or less, such as 6 nM or less, such as 5 nM or less, such as 4 nM or less, such as 3 nM or less, such as 2 nM or less, such as 1.5 nM or less, such as 1 nM or less. Suitably the EC50 is established using the IL-7-induced STAT5 phosphorylation assay detailed in Example 1 below.

Suitably, the affinity of the IL-7R binding polypeptide is determined by surface plasmon resonance.

Suitably, the IL-7R binding polypeptide binds to IL-7R with an equilibrium dissociation constant (Kd) of $10^{-7}$ M or less, more suitably $10^{-8}$ M or less, more suitably $10^{-9}$ M or less and more suitably $10^{-10}$ M or less.

In one embodiment, the affinity of the IL-7R binding polypeptide is established by coating directly on a Biacore (or equivalent) sensor plate, wherein the polypeptide is flowed over the plate to detect binding. Suitably a Biacore T200 plate is used at 25° C. in HBS-EP+(GE Healthcare) running buffer at 30 ul/min.

Structural Properties

Suitably the IL-7R binding polypeptide is a polypeptide comprising an antibody fragment. The polypeptide may be an antibody. Suitably the antibody fragment is selected from the group consisting of: V-NARs, scFvs, Fab fragments, F(ab')2 fragments or immunoglobulin chain variable domains such as VLs, VHHs and VHs. More suitably the antibody fragment is an immunoglobulin chain variable domain, more suitably a VHH or VH, most suitably a VHH.

Suitably the IL-7R binding polypeptide comprises three CDRs (CDR1, CDR2 and CDR3).

Suitably CDR1 of the IL-7R binding polypeptide comprises or more suitably consists of a sequence sharing 20%, 40%, 60%, or 80% or greater sequence identity, with SEQ ID NO: 9.

Alternatively, CDR1 of the polypeptide of the IL-7R binding polypeptide comprises or more suitably consists of a sequence having no more than 4, more suitably no more than 3, more suitably no more than 2, more suitably no more than 1 addition(s), substitution(s) and/or deletion(s) compared to SEQ ID NO: 9.

Suitably any residues of CDR1 of the IL-7R binding polypeptide differing from their corresponding residues in SEQ ID NO: 9 are conservative substitutions with respect to their corresponding residues. Suitably CDR1 of the IL-7R binding polypeptide comprises or more suitably consists of SEQ ID NO: 9.

Suitably the residues of CDR1 have the following identities (SEQ ID NO: 28):

| 1 | 2 | 3 | 4 | 5 |
|---|---|---|---|---|
| S/D | D | A | M | G |

More suitably CDR1 comprises or more suitably consists of SEQ ID NO: 9.

Suitably CDR2 of the IL-7R binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater sequence identity, with SEQ ID NO: 10.

Alternatively, CDR2 of the IL-7R binding polypeptide comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s), substitution(s) and/or deletion(s) compared to SEQ ID NO: 10.

Suitably any residues of CDR2 of the IL-7R binding polypeptide differing from their corresponding residues in SEQ ID NO: 10 are conservative substitutions with respect to their corresponding residues. Suitably CDR2 of the IL-7R binding polypeptide comprises or more suitably consists of SEQ ID NO: 10.

Suitably the residues of CDR2 have the following identities (SEQ ID NO: 29):

| 1 | 2 | 3 | 4 | 5 | 6 | 7 | 8 | 9 | 10 | 11 | 12 | 13 | 14 | 15 | 16 | 17 |
|---|---|---|---|---|---|---|---|---|----|----|----|----|----|----|----|----|
| A | I/T | G/N | W | S | G | A/T | V | T | H | Y | S/G | D | S | V | Q/K | G |

Suitably the residue of CDR2 corresponding to residue number 16 of SEQ ID NO: 10 is Q or K, most suitably K. Suitably CDR2 comprises or consists of SEQ ID NO: 10. More suitably CDR2 comprises or more suitably consists of SEQ ID NO: 10.

Suitably CDR3 of the IL-7R binding polypeptide comprises or more suitably consists of a sequence sharing 20% or greater, more suitably 30% or greater, more suitably 40% or greater, more suitably 50% or greater, more suitably 55% or greater, more suitably 60% or greater, more suitably 65% or greater, more suitably 70% or greater, more suitably 75% or greater, more suitably 80% or greater, more suitably 85% or greater, more suitably 90% or greater sequence identity with SEQ ID NO: 11.

Alternatively, CDR3 of the IL-7R binding polypeptide comprises or more suitably consists of a sequence having no more than 6, more suitably no more than 5, more suitably no more than 4, more suitably no more than 3, more suitably no more than 2, more suitably no more than 1 addition(s), substitution(s) and/or deletion(s) compared to SEQ ID NO: 11.

Suitably any residues of CDR3 of the IL-7R binding polypeptide differing from their corresponding residues in SEQ ID NO: 11 are conservative substitutions with respect to their corresponding residues.

Suitably the residues of CDR3 have the following identities (SEQ ID NO: 30):

| 1 | 2 | 3 | 4 | 5 | 6 | 7 | 8 | 9 |
|---|---|---|---|---|---|---|---|---|
| D | Y | D/V | T | D | V | W | Q | Y/H |

Suitably CDR3 of the IL-7R binding polypeptide comprises or more suitably consists of SEQ ID NO: 11.

Suitably the IL-7R binding polypeptide comprises three CDRs (CDR1, CDR2 and CDR3) and four framework regions (FR1-FR4).

Suitably FR1 of the IL-7R binding polypeptide comprises or more suitably consists of a sequence sharing 5%, 12%, 18%, 26%, 32%, 38%, 46%, 52%, 58%, 62%, 66%, 68%, 72%, 75%, 78%, 82%, 85%, 90% or 95% or greater sequence identity, with SEQ ID NO: 12.

Suitably any residues of FR1 differing from their corresponding residues in SEQ ID NO: 12 are conservative substitutions with respect to their corresponding residues. Suitably the residue of FR1 corresponding to residue number 1 of SEQ ID NO: 12 is D or E, most suitably D. Suitably the residues of FR1 corresponding to residue numbers 1 to 5 of SEQ ID NO: 12 are DVQLV. Suitably FR1 comprises or more suitably consists of SEQ ID NO: 12. Suitably the residue of FR1 corresponding to residue number 24 of SEQ ID NO: 12 is S.

Suitably FR2 of the IL-7R binding polypeptide comprises or more suitably consists of a sequence sharing 10%, 15%, 25%, 30%, 40%, 45%, 55%, 60%, 70%, 75%, 85% or 90% or greater sequence identity, with SEQ ID NO: 13.

Suitably any residues of FR2 differing from their corresponding residues in SEQ ID NO: 13 are conservative substitutions with respect to their corresponding residues. Suitably the residue of FR2 corresponding to residue number 10 of SEQ ID NO: 13 is R or L, most suitably L. Suitably the residues of FR2 corresponding to residue numbers 8 to 11 of SEQ ID NO: 13 are KEXE, wherein X is R or L, most suitably L. Alternatively the residues of FR2 corresponding to residue numbers 9 to 12 of SEQ ID NO: 13 are GLEW. Suitably FR2 comprises or more suitably consists of SEQ ID NO: 13. Suitably the residue of FR2 corresponding to residue number 2 of SEQ ID NO: 13 is F, more suitably, in addition, the residue of FR2 corresponding to residue number 14 of SEQ ID NO: 13 is A. Suitably the residues of FR2 corresponding to residues 9-14 of SEQ ID NO: 13 are ELEFLA (SEQ ID NO: 79). Suitably the residues of FR2 corresponding to residues 9-14 of SEQ ID NO: 13 are not GLEWVS (SEQ ID NO: 80). Suitably the residue of FR2 corresponding to residue number 9 of SEQ ID NO: 13 is not G. More suitably the residue of FR2 corresponding to residue number 9 of SEQ ID NO: 13 is E.

Suitably FR3 of the IL-7R binding polypeptide comprises or more suitably consists of a sequence sharing 8%, 15%, 20%, 26%, 32%, 40%, 45%, 52%, 58%, 65%, 70%, 76%, 80%, 82%, 85%, 90%, 92% or 95% or greater sequence identity, with SEQ ID NO: 14.

Suitably any residues of FR3 differing from their corresponding residues in SEQ ID NO: 14 are conservative substitutions with respect to their corresponding residues. Suitably FR3 comprises or more suitably consists of SEQ ID NO: 14. Suitably the residues of FR3 corresponding to residue numbers 18, 19 and 20 of SEQ ID NO: 14 are NSL. Suitably the residue of FR3 corresponding to residue number 21 of SEQ ID NO: 14 is R. Suitably the residue of FR3 corresponding to residue number 22 of SEQ ID NO: 14 is A.

Suitably FR4 of the IL-7R binding polypeptide comprises or more suitably consists of a sequence sharing 5%, 10%, 20%, 30%, 40%, 50%, 60%, 70%, 80% or 90% or greater sequence identity, with SEQ ID NO: 15.

Suitably any residues of FR4 of the IL-7R binding polypeptide differing from their corresponding residues in SEQ ID NO: 15 are conservative substitutions with respect to their corresponding residues. Suitably FR4 of the IL-7R binding polypeptide comprises or more suitably consists of SEQ ID NO: 15.

Suitably the IL-7R binding polypeptide comprises or more suitably consists of a sequence sharing 50%, 55%, 60%, 65%, 70%, 75%, 80%, 85%, 90%, 95%, 96%, 97%, 98% or 99% or greater sequence identity, with SEQ ID NO: 16.

Suitably the IL-7R binding polypeptide comprises or more suitably consists of SEQ ID NO: 16.

According to a specific embodiment, the IL-7R binding polypeptide has an amino acid sequence which is not exactly the same as (i.e. shares 100% sequence identity with) the amino acid sequence of a naturally occurring polypeptide. Particular Combined Structural and Functional Properties of Both the TNF-Alpha Binding Polypeptide and the IL-7R Binding Polypeptide Suitably both the TNF-alpha binding polypeptide and the IL-7R binding polypeptide are immunoglobulin chain variable domains wherein:

(a) CDR1 of the TNF-alpha binding polypeptide comprises a sequence sharing 40% or greater sequence identity with SEQ ID NO: 1;

(b) CDR2 of the TNF-alpha binding polypeptide comprises a sequence sharing 40% or greater sequence identity with SEQ ID NO: 2;

(c) CDR3 of the TNF-alpha binding polypeptide comprises a sequence sharing 50% or greater sequence identity with SEQ ID NO: 3;

(d) CDR1 of the IL-7R binding polypeptide comprises a sequence sharing 40% or greater sequence identity with SEQ ID NO: 9;

(e) CDR2 of the IL-7R binding polypeptide comprises a sequence sharing 40% or greater sequence identity with SEQ ID NO: 10;

(f) CDR3 of the IL-7R binding polypeptide comprises a sequence sharing 50% or greater sequence identity with SEQ ID NO: 11, more suitably wherein:

(a) CDR1 of the TN F-alpha binding polypeptide comprises a sequence sharing 60% or greater sequence identity with SEQ ID NO: 1;

(b) CDR2 of the TNF-alpha binding polypeptide comprises a sequence sharing 50% or greater sequence identity with SEQ ID NO: 2;

(c) CDR3 of the TNF-alpha binding polypeptide comprises a sequence sharing 60% or greater sequence identity with SEQ ID NO: 3;

(d) CDR1 of the IL-7R binding polypeptide comprises a sequence sharing 60% or greater sequence identity with SEQ ID NO: 9;

(e) CDR2 of the IL-7R binding polypeptide comprises a sequence sharing 50% or greater sequence identity with SEQ ID NO: 10;

(f) CDR3 of the IL-7R binding polypeptide comprises a sequence sharing 60% or greater sequence identity with SEQ ID NO: 11, more suitably wherein:

(a) CDR1 of the TNF-alpha binding polypeptide comprises a sequence sharing 60% or greater sequence identity with SEQ ID NO: 1;

(b) CDR2 of the TNF-alpha binding polypeptide comprises a sequence sharing 70% or greater sequence identity with SEQ ID NO: 2;

(c) CDR3 of the TNF-alpha binding polypeptide comprises a sequence sharing 65% or greater sequence identity with SEQ ID NO: 3;

(d) CDR1 of the IL-7R binding polypeptide comprises a sequence sharing 60% or greater sequence identity with SEQ ID NO: 9;

(e) CDR2 of the IL-7R binding polypeptide comprises a sequence sharing 70% or greater sequence identity with SEQ ID NO: 10;

(f) CDR3 of the IL-7R binding polypeptide comprises a sequence sharing 65% or greater sequence identity with SEQ ID NO: 11, more suitably wherein:

(a) CDR1 of the TNF-alpha binding polypeptide comprises a sequence sharing 80% or greater sequence identity with SEQ ID NO: 1;

(b) CDR2 of the TNF-alpha binding polypeptide comprises a sequence sharing 85% or greater sequence identity with SEQ ID NO: 2;

(c) CDR3 of the TNF-alpha binding polypeptide comprises a sequence sharing 80% or greater sequence identity with SEQ ID NO: 3;

(d) CDR1 of the IL-7R binding polypeptide comprises a sequence sharing 80% or greater sequence identity with SEQ ID NO: 9;

(e) CDR2 of the IL-7R binding polypeptide comprises a sequence sharing 85% or greater sequence identity with SEQ ID NO: 10;

(f) CDR3 of the IL-7R binding polypeptide comprises a sequence sharing 80% or greater sequence identity with SEQ ID NO: 11, and in each case wherein most suitably the TNF-alpha binding polypeptide neutralizes human TNF-alpha cytotoxicity in the L929 assay with an EC50 of 100 nM or less and the IL-7R binding polypeptide neutralizes IL-7R-dependent, IL-7-induced STAT5 phosphorylation in human lymphocytes with an EC50 of 100 nM or less; and/or wherein the TNF-alpha binding polypeptide binds to TNF-alpha with a Kd of $10^{-7}$ M or less and the IL-7R binding polypeptide binds to IL-7R with a Kd of $10^{-7}$ M or less. Most suitably the polypeptides above are provided in a bihead construct for use in the treatment of Crohn's disease or ulcerative colitis by oral administration.

Suitably both the TNF-alpha binding polypeptide and the IL-7R binding polypeptide are the same type of immunoglobulin chain variable domain, e.g. VHs, VHHs or VLs, more suitably VHs or VHHs.

Format of TNF-Alpha and IL-7R Binding Polypeptides

The TNF-alpha binding polypeptide and the IL-7R binding polypeptide may be linked or unlinked.

In one embodiment, the TNF-alpha binding polypeptide and the IL-7R binding polypeptide may be present in the composition of the invention independently from one another (i.e. the TNF-alpha and IL-7R binding polypeptides are not linked to each other). In a specific embodiment, the composition comprises (a) ID-38F (SEQ ID NO: 8) or a polypeptide having at least 75%, more suitably at least 85% identity thereto and (b) ID-A62U (SEQ ID NO: 16) or a polypeptide having at least 75%, more suitably at least 85% identity thereto.

In a further embodiment, the TNF-alpha binding polypeptide and the IL-7R binding polypeptide comprised in the composition of the invention are linked to each other (thereby forming a single construct). Such a format may be convenient for recombinant expression purposes. Such a construct of the invention is therefore multimeric and multivalent. If no further polypeptides are comprised within the construct, then such a construct may be referred to as a 'heterobihead'. A multivalent construct comprises two or more binding polypeptides and therefore provides two or more sites at which attachment to antigens can occur (suitably before or after cleavage of the labile peptide linker, if such a linker is present in the construct—see 'Linkers' below).

Suitably each polypeptide in the construct has a molecular weight of no greater than 300 kDa, such as 250 kDa, such as 200 kDa, such as 180 kDa, such as 160 kDa, such as 140 kDa, such as 120 kDa, such as 100 kDa, such as 80 kDa, such as 60 kDa, such as 40 kDa, such as 30 kDa, such as 20 kDa, such as 15 kDa.

Linkers

The TNF-alpha and IL-7R binding polypeptides, if linked, can be linked to each other directly (i.e. without use of a linker) or via a linker. Suitably a linker is used. The linker may be a protease-labile or a non-protease-labile linker. The linker is suitably a peptide, suitably selected so as to allow binding of the polypeptides to their epitopes. Suitably the linker is flexible, for example sufficiently flexible to allow both binding polypeptides to bind their targets simultaneously. If used for therapeutic purposes, the linker is suitably non-immunogenic in the subject to which the polypeptides are administered. Suitably the polypeptides and linker are expressed as a single contiguous polypeptide construct.

Suitably the peptide linker has a length of at least 5, such as at least 7, such as at least 10, such as at least 13, such as at least 16, such as at least 19, such as at least 20, such as at least 21 residues. Suitably the peptide linker has a length of no greater than 40, such as no greater than 35, such as no greater than 30, such as no greater than 25 residues.

Suitably the peptide linker consists of any amino acids selected from the list consisting of: arginine, histidine, lysine, aspartic acid, glutamic acid, serine, threonine, asparagine, glutamine, cysteine, glycine, proline, alanine, valine, isoleucine, leucine, methionine, phenylalanine, tyrosine and tryptophan. Proline may be a sub-optimal amino acid for inclusion in a linker and therefore more suitably the peptide linker consists of any amino acids selected from the list consisting of: arginine, histidine, lysine, aspartic acid, glutamic acid, serine, threonine, asparagine, glutamine, cysteine, glycine, alanine, valine, isoleucine, leucine, methionine, phenylalanine, tyrosine and tryptophan.

The TNF-alpha and IL-7R binding polypeptides, if linked, may be in the orientation (from N- to C-terminus) anti-TNF-alpha-linker-anti-IL-7R or may be in the orientation anti-IL-7R-linker-anti-TNF-alpha. Most suitably, they are in the orientation anti-TNF-alpha-linker-anti-IL-7R.

Compositions of the invention comprising TNF-alpha and IL-7R binding polypeptides linked by peptide linkers may for example be obtained by preparing a nucleic acid encoding the two binding polypeptides and a peptide linker using techniques for nucleic acid synthesis, followed by expression of the nucleic acid thus obtained (as detailed further under the heading 'preparative methods' below).

Non-Protease-Labile Linkers

Suitably the non-protease-labile linker is a peptide and does not comprise a cleavage site for a protease.

Suitably the non-protease-labile linker is of the format $-(G_aS_b)_x$- wherein a is 1 to 10, b is 1 to 5 and x is 1 to 15 (SEQ ID NO: 31). More suitably a is 1 to 5, b is 1 to 2 and x is 1 to 10. More suitably a is 4, b is 1 and x is 1 to 8 (SEQ ID NO: 32).

Protease-Labile Linkers

Protease-labile linkers are more suitable than non-protease-labile linkers because protease-labile linkers allow constituent monomers to be released and to freely bind their targets upon cleavage. A protease-labile linker (or 'labile peptide linker') is a peptide and comprises at least one cleavage site for a protease. Including a protease-labile linker in a construct of the invention allows, for example, the construct to be conveniently produced in the form of a heterobihead which is then later cleaved after administration into separate binding polypeptides.

In one embodiment of the invention, the labile peptide linker can be engineered such that it resists cleavage by proteases to a desired extent and/or is only cleaved upon exposure to a specific area of the intestinal tract. For example, if a construct is recombinantly produced in a host such as yeast, trypsin-like proteases produced by the yeast may cleave the recombinant construct product. This may result in difficulties in purification and cause regulatory, clinical and commercial complications.

This can be achieved by incorporating shielding residues into the labile peptide linker flanking the labile site(s). Shielding residues flank the labile site(s) of the labile peptide linker and reduce the lability thereof. Cleavage resistance can also be increased by positioning the labile site(s) closer to or at the periphery of the labile peptide linker. This concept is referred to as a "shielded labile site" and provides controlled lability.

The labile peptide linker can alternatively be engineered such that it is highly labile to cleavage by intestinal tract proteases, thereby quickly releasing the constituent polypeptides of the construct after oral administration. This is achieved by incorporating one or more labile sites into the labile peptide linker such that the labile site is exposed for proteolysis, for example by positioning the labile site(s) substantially centrally in the labile peptide linker and/or by the labile site not being shielded substantially by flanking residues. This concept is referred to as a "non-shielded labile site".

Incorporation of a P residue into the labile peptide linker of the construct of the invention immediately following an R or K residue is expected to substantially prevent cleavage of the labile peptide linker. Suitably the labile peptide linker does not comprise any P residues.

Trypsin Labile Sites

Suitably the labile peptide linker comprises a cleavage site for trypsin or a trypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 K residues. Suitably the labile peptide linker comprises at least 1, such as at least 2, such as at least 3, such as at least 4, such as at least 5, such as at least 6, such as at least 7, such as at least 8, such as at least 9, such as at least 10 R residues. Preferably the cleavage site(s) is/are one or more K residue(s).

Suitably the protease-labile linker comprises or more suitably consists of the format $[-(G_aS_b)_v-(G_cS_d)_w-B_t-(G_eS_f)_x-(G_gS_h)_y]_z$ wherein B is lysine or arginine; t is 1 to 5; a, c, e and g are each independently 0 to 10; b, d, f and h are each independently 0 to 5; v, w, x and y are each independently 0 to 10 and z is 1 to 5 (SEQ ID NO: 33). More suitably B is lysine or arginine; t is 1 to 2; a, c, e and g are each independently 1 to 5; b, d, f and h are each independently 1 to 3; v, w, x and y are each independently 1 to 3 and z is 1 to 3, more suitably B is lysine or arginine; t is 1; a, c, e and g are each independently 2 to 4; b, d, f and h are each independently 1 to 2; v, w, x and y are each independently 1 to 2 and z is 1.

Particularly favoured linkers of this format are selected from $-(G_4S)_x-K-(G_4S)_y$- wherein x and y are each independently 1 to 5 (SEQ ID NO: 34), more suitably $-(G_4S)_2-K-(G_4S)_2$- (i.e. -GGGGSGGGGSKGGGGSGGGGS- (SEQ ID NO: 21).

Suitably the labile peptide linker comprises or more suitably consists of a polypeptide sequence of the format:

$-B-(GaS)_x-B'-$ wherein
a is 1 to 10;
x is 1 to 10;
B is K or R and
B' is K or R (SEQ ID NO: 35).

In one embodiment, a is 2 to 5, more suitably a is 4. In a further embodiment x is 1 to 5. More suitably, x is 2. B may be present or not present. B' may be present or not present. Suitably, B is K. Suitably, B' is K.

Particularly favoured linkers of this format are selected from one of the list consisting of $-K-(G_4S)_2-K-$ (SEQ ID NO: 36), $-(G_4S)_2-K-$ (SEQ ID NO: 37), $-K-(G_4S)_2-$ (SEQ ID NO: 38), $-R-(G_4S)_2-R-$ (SEQ ID NO: 39), $-(G_4S)_2-R-$ (SEQ ID NO: 40) and $-R-(G_4S)_2-$ (SEQ ID NO: 41).

Suitably the labile peptide linker comprises or more suitably consists of a polypeptide sequence of the format:

$-B-(G_aS)_x-B'-(G_bS)_y-B''-$ wherein
a is 1 to 10;
b is 1 to 10;
x is 1 to 10;
y is 1 to 10;
B is K or R;
B' is K or R and
B'' is K or R (SEQ ID NO: 42).

In one embodiment, a is 2 to 5, more suitably a is 4. In one embodiment, b is 2 to 5, more suitably b is 4. In a further embodiment x is 1 to 5. More suitably, x is 2. In a further embodiment y is 1 to 5. More suitably, y is 2. Suitably, B is K. Suitably, B' is K. Suitably, B" is K.

Chymotrypsin Labile Sites

Alternatively, or in addition to trypsin labile sites, the labile peptide linker of the construct may comprise a cleavage site for chymotrypsin or a chymotrypsin-like protease. Suitably the labile peptide linker comprises at least 1, such as at least 2, such as at least 3, such as at least 4, such as at least 5, such as at least 6, such as at least 7, such as at least 8, such as at least 9, such as at least 10 residues selected from the list consisting of W, F, Y, L and M; more suitably W, F and Y. Suitably the labile peptide linker consists of residues selected from the list consisting of S, G, W, F, Y, L and M; such as S, G, W, F and Y.

Suitably the protease-labile linker comprises or more suitably consists of the format $[-(G_aS_b)_v-(G_cS_d)_w-J_t-(G_eS_f)_x-(G_gS_h)_y]_z$ wherein J is W, F, Y, L or M; t is 1 to 5; a, c, e and g are each independently 0 to 10; b, d, f and h are each independently 0 to 5; v, w, x and y are each independently 0 to 10 and z is 1 to 5 (SEQ ID NO: 43). More suitably J is W, F, Y, L or M; t is 1 to 2; a, c, e and g are each independently 1 to 5; b, d, f and h are each independently 1 to 3; v, w, x and y are each independently 1 to 3 and z is 1 to 3, more suitably J is W, F, Y, L or M; t is 1; a, c, e and g are each independently 2 to 4; b, d, f and h are each independently 1 to 2; v, w, x and y are each independently 1 to 2 and z is 1.

Enterokinase Labile Sites

Alternatively, or in addition to trypsin and/or chymotrypsin labile sites, the labile peptide linker of the construct may comprise a cleavage site for an enterokinase. Suitably the labile peptide linker comprises the sequence DDDDK (SEQ ID NO: 19), such as a sequence comprising or consisting of -G₄S-DDDDK-G₄S- (SEQ ID NO: 20).

MMP Labile Sites

In one embodiment, the labile peptide linker of the construct may comprise a cleavage site for MMP3, MMP10 or MMP12.

Other Labile Sites

In one embodiment, the labile peptide linker of the construct may comprise a cleavage site for other inflammatory or microbial proteases wherein the cleavage site is known.

Stability of Polypeptides within Constructs

In embodiments wherein the construct comprises a non-protease-labile linker, then suitably the construct as a whole (i.e. the binding polypeptides (which may be immunoglobulin chain variable domains) and the non-protease-labile linker) is substantially resistant to proteases such as trypsin and chymotrypsin. In embodiments wherein the construct comprises a protease-labile linker, then suitably the polypeptides (i.e. the binding polypeptides, which may be immunoglobulin chain variable domains) are substantially resistant to proteases such as trypsin and chymotrypsin but the protease-labile linker is labile to proteases such as trypsin or chymotrypsin.

Stability of Labile Peptide Linkers to Expression Hosts

Various organisms may be used to express recombinant polypeptides. Commonly used expression organisms include yeast, mould and mammalian cells. However, many of these expression organisms also produce proteases, such as trypsin-like proteases, which may cleave the expressed recombinant polypeptide. If the expressed polypeptide incorporates a peptide linker which is labile to one or more proteases present in the intestinal tract, then this peptide linker may undesirably also be labile to proteases produced by the expression organism, thus preventing effective expression of intact polypeptide.

It is advantageous for the labile peptide linker to be substantially non-labile to enzymes produced by the recombinant host used to produce the construct. Suitably the labile peptide linker is substantially resistant to proteases produced by a recombinant host such as bacteria such as *E. coli* or such as a yeast or mould belonging to the genera *Aspergillus, Saccharomyces, Kluyveromyces, Hansenula* or *Pichia*; such as *Saccharomyces cerevisiae* or *Pichia pastoris*.

Suitably the recombinant host is a yeast or a mould. Suitably the yeast belongs to the genera *Saccharomyces, Kluyveromyces, Hansenula, Pichia, Candida* or *Torulopsis*. Suitably the mould belongs to the genus *Aspergillus, Acremonium, Alternaria, Chrysosporium, Cladosporium, Dictyostelium, Fusarium, Mucor, Penicillium, Rhizopus, Stachybotrys, Trichoderma* and *Trichophyton*.

The Gastrointestinal Tract and Digestive Enzymes

The gastrointestinal tract (GIT) is an organ system responsible for consuming and digesting foodstuffs, absorbing nutrients, and expelling waste. In humans and other mammals, the GIT consists of the oesophagus, stomach, small intestine (duodenum, jejunum and ileum) and large intestine (cecum, colon, rectum and anal canal). Various pathogens may colonise and various diseases may manifest in different areas of the GIT. The intestinal tract (as opposed to the gastrointestinal tract) consists of the small and large intestine.

The different parts of the gastrointestinal tract each contain a complex mixture of digestive enzymes. Proteases are involved in digesting polypeptide chains into shorter fragments by splitting the peptide bonds that link amino acid residues (proteolysis). Some detach the terminal amino acids from the protein chain (exopeptidases), others attack internal peptide bonds of a protein (endopeptidases). Proteolysis can be highly promiscuous such that a wide range of protein substrates are hydrolysed. This is the case for proteases which cleave the wide array of ingested polypeptides in the intestinal tract into smaller polypeptide fragments.

Many proteases typically bind to a single amino acid (a labile site) on the substrate and so only have specificity for that residue. The proteases present in the intestinal tract include trypsin, trypsin-like proteases, chymotrypsin, chymotrypsin-like proteases, carboxypeptidase, elastase, aminopeptidase, carboxypeptidase and enteropeptidase. Trypsin-like proteases cleave peptide bonds following lysine or arginine residues. Chymotrypsin-like proteases cleave peptide bonds following hydrophobic residues, such as tyrosine, phenylalanine, tryptophan, leucine and methionine. Particularly tyrosine, phenylalanine and tryptophan.

Particularly in the context of an oral medicament, it may be desirable for the binding polypeptides to be substantially resistant to one or more (such as all) proteases of the intestinal tract, while the labile peptide linker (if used) is labile to one or more (such as all) proteases of the intestinal tract.

Suitably the polypeptides in the construct are substantially resistant to one or more proteases and suitably the labile peptide linker (if present) is labile to one or more proteases, wherein said one or more proteases are present in the small or large intestine, more suitably the jejunum, the ileum and/or the cecum. A substantially resistant polypeptide substantially retains neutralisation ability and/or potency when exposed to one or more proteases.

Such proteases include proteases sourced from gastrointestinal tract commensal microflora or pathogenic bacteria, for example wherein the proteases are cell membrane-attached proteases, secreted proteases and proteases released on cell lysis. Such proteases may also include IBD inflammatory proteases such as MMP3, MMP10 and MMP12. Suitably the one or more proteases are serine proteases. Suitably the one or more proteases are selected from the group consisting of enteropeptidase, trypsin, trypsin-like proteases, chymotrypsin and chymotrypsin-like proteases.

Suitably, the polypeptides substantially retain neutralisation ability and/or potency when delivered orally and after exposure to the intestinal tract (for example, after exposure to proteases of the small and/or large intestine and/or IBD inflammatory proteases). Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, rat, guinea pig, hamster, rabbit, human, cynomolgus monkey or mouse. The small intestine suitably consists of the duodenum, jejunum and ileum. The large intestine suitably consists of the cecum, colon, rectum and anal canal.

The polypeptides substantially retain neutralisation ability when suitably at least 10%, more suitably 20%, more suitably 30%, more suitably 40%, more suitably 50%, more suitably 60%, more suitably 70%, more suitably 80%, more suitably 90%, more suitably 95%, more suitably 100% of the original neutralisation ability of the polypeptides or construct is retained after exposure to proteases present in the small and/or large intestine and/or IBD inflammatory proteases; after a given time period of exposure at a given temperature. This concept is referred to herein as '% survival'.

Suitably the polypeptide substantially retains neutralisation ability after exposure to proteases present in the small and/or large intestine and/or IBD inflammatory proteases for, for example, up to at least 2, more suitably up to at least 3, more suitably up to at least 4, more suitably up to at least 5, more suitably up to at least 5.5, more suitably up to at least 6, more suitably up to at least 12, more suitably up to at least 14 or more suitably up to at least 16 hours, at 37 degrees C.

The polypeptides substantially retain neutralisation ability when suitably at least 10%, more suitably at least 20%, more suitably at least 30%, more suitably at least 40%, more suitably at least 50%, more suitably at least 60%, more suitably at least 70%, more suitably at least 80%, more suitably at least 90%, more suitably at least 95%, more suitably at least 100% of the original neutralisation ability of the polypeptides or construct is retained after exposure to human faecal supernatant or mouse small intestinal fluid; after a given time period of exposure at a given temperature. This concept is referred to herein as '% survival'.

Suitably the polypeptide substantially retains neutralisation ability after exposure to human faecal supernatant or mouse small intestinal fluid for, for example, up to at least 2, more suitably up to at least 3, more suitably up to at least 4, more suitably up to at least 5, more suitably up to at least 5.5, more suitably up to at least 6, more suitably up to at least 12, more suitably up to at least 14 or more suitably up to at least 16 hours, at 37 degrees C.

Autoimmune Diseases and/or Inflammatory Diseases

The compositions and constructs provided by the invention may in particular find utility in the prevention or treatment of autoimmune diseases and/or inflammatory diseases. Suitably the autoimmune disease and/or inflammatory disease is inflammatory bowel disease and/or mucositis, most suitably inflammatory bowel disease (such as Crohn's disease, ulcerative colitis or check-point inhibitor induced colitis, most suitably ulcerative colitis or Crohn's disease).

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

Autoimmune Diseases and/or Inflammatory Diseases of the GIT

The chronic inflammatory bowel diseases (IBD) Crohn's disease and ulcerative colitis, which afflict both children and adults, are examples of autoimmune and inflammatory diseases of the GIT (gastrointestinal tract) (Hendrickson et al 2002, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al 2002, herein incorporated by reference in its entirety).

Other diseases of the GIT include for example the inflammatory disease mucositis (suitably drug- and radiation induced-mucositis) where inflammatory lesions are present in the mucosa disrupting the epithelial tight junctions. In mucositis the lesions can occur anywhere from mouth to anus and for mouth and oesophagus lesions a mouthwash or cream preparation containing the composition may be used. For anal and rectal lesions, suppositories, creams or foams containing the composition would be suitable for topical application. The composition will be cleared from the lamina propria or other inflammatory sites via absorption into the bloodstream at sites of inflammation or via lymphatic clearance and subsequent entry into the bloodstream. The composition will therefore reach the liver via the bloodstream and will be cleared via glomerular filtration in the kidney. There is therefore good rationale that the composition of the invention will function therapeutically in diseases such as autoimmune hepatitis, type II diabetes and glomerular nephritis.

Suitably the composition of the invention is used in the treatment or prevention of an autoimmune and/or inflammatory disease of the GIT.

Suitably the composition of the invention is for use in the treatment of an autoimmune and/or inflammatory disease of the GIT selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis, oesophagitis and check-point inhibitor induced colitis (more suitably Crohn's disease, ulcerative colitis or check-point inhibitor induced colitis, most suitably ulcerative colitis or Crohn's disease).

Oral delivery of the composition will ideally treat inflammatory diseases where TNF-alpha (or TNF-alpha receptor) and/or IL-7R (or IL-7 or L-TSLP) contributes to at least a proportion of the pathology and more suitably wherein the immunoglobulin chain variable domain can access the tissue where these cytokines are biologically active.

Autoimmune Diseases and/or Inflammatory Diseases of the Skin

Psoriasis is a debilitating autoimmune, dermatological, disease. Plaque psoriasis, the most common form of the disease, is characterized by red skin covered with silvery scales. Histologically the picture is one of disordered differentiation and hyperproliferation of keratinocytes within the psoriatic plaque with inflammatory cell infiltrates (Ortonne, 1999). The psoriatic skin lesions are inflammatory, red, sharply delimited plaques of various shapes with characteristic silvery lustrous scaling. The term psoriasis includes psoriasis and the symptoms of psoriasis including erythema, skin thickening/elevation and scaling.

Biological agents of use in the treatment of psoriasis include anti-TNF-alpha therapies (such as monoclonal antibodies against TNF, e.g. adalimumab and infliximab, or TNF-alpha receptor fusion proteins such as etanercept), humanised antibodies to CD11a (efalizumab) or agents which bind to CD2 such as alefacept (thereby blocking the CD2 LFA3 interaction). It should be noted that not all of the biological agents listed here have been approved for use in the treatment of psoriasis.

The composition of the invention may be incorporated into a cream/ointment or other topical carrier for administration to inflammatory skin lesions where TNF-alpha (or TNF-alpha receptor) and/or IL-7R (or IL-7 or L-TSLP) contributes to the pathology of such lesions.

Suitably the composition of the invention is for use in the treatment of an autoimmune and/or inflammatory disease of the skin selected from the list consisting of pemphigus, psoriasis, eczema and scleroderma.

In one embodiment the polypeptide or construct of the invention is for use in the treatment or prevention of atopic dermatitis, suitably by topical delivery to and/or through the skin, suitably in the form of a cream, nanoparticles, ointment or hydrogel.

Therapeutic Use and Delivery

Suitably the composition of the invention is for use as a medicament, suitably administered by oral administration, suitably for use in the treatment or prevention of diseases of the GIT and/or the treatment or prevention of diseases such as autoimmune disease and/or inflammatory disease, such as inflammatory bowel disease. Suitably the construct of the invention is for use as a medicament, suitably administered by oral administration. The composition of the invention may also be used in the treatment or prevention of other medical conditions by oral administration such as metabolic disorders, such as obesity. In one embodiment, the composition of the invention is intended to have local effect in the intestinal tract. In one embodiment, the composition of the invention is not for use in the treatment or prevention of diseases by delivery into the circulation in therapeutically effective quantities.

In one aspect of the invention there is provided a method of treating autoimmune disease and/or inflammatory disease comprising administering to a person in need thereof a therapeutically effective amount of the inventive composition. Suitably the autoimmune disease and/or inflammatory disease is inflammatory bowel disease and/or mucositis.

The anti-TNF-alpha binding polypeptide and the anti-IL-7R binding polypeptide may be co-formulated in a composition of the invention or alternatively may be separately formulated and administered separately, sequentially or simultaneously.

The TNF-alpha binding polypeptide and the IL-7R binding polypeptide may be administered by the same route or by different routes. For example, the TNF-alpha binding polypeptide may be administered orally while the IL-7R binding polypeptide may be administered rectally.

In one aspect of the invention, there is provided a TNF-alpha binding polypeptide for use in the treatment or prevention of an autoimmune disease and/or inflammatory disease, together with an IL-7R binding polypeptide. In a further aspect, there is provided an IL-7R binding polypeptide for use in the treatment or prevention of an autoimmune disease and/or inflammatory disease, together with a TNF-alpha binding polypeptide.

In a further aspect of the invention there is provided a method of treating autoimmune disease and/or inflammatory disease comprising administering to a person in need thereof a TNF-alpha binding polypeptide, together with an IL-7R binding polypeptide. There is also provided a method of treating autoimmune disease and/or inflammatory disease comprising administering to a person in need thereof an IL-7R binding polypeptide, together with a TNF-alpha binding polypeptide.

In a further aspect of the invention there is provided a composition comprising a TNF-alpha binding polypeptide and an IL-7R binding polypeptide for use in the treatment or prevention of inflammatory bowel disease and/or mucositis.

In a further aspect of the invention there is provided a composition comprising a TNF-alpha binding polypeptide and an IL-7R binding polypeptide for use in the treatment or prevention of inflammatory bowel disease and/or mucositis, wherein the composition is orally administered.

In a further aspect of the invention there is provided the use of a composition comprising a TNF-alpha binding polypeptide and an IL-7R binding polypeptide in the manufacture of a medicament for the treatment or prevention of autoimmune disease and/or inflammatory disease, suitably inflammatory bowel disease and/or mucositis.

In a further aspect of the invention there is provided the use of a composition comprising a TNF-alpha binding polypeptide and an IL-7R binding polypeptide in the manufacture of a medicament for the treatment or prevention of autoimmune disease and/or inflammatory disease, suitably inflammatory bowel disease and/or mucositis, by oral administration.

In a further aspect of the invention there is provided a method of treating or preventing inflammatory bowel disease and/or mucositis comprising administering to a person in need thereof a composition comprising a TNF-alpha binding polypeptide and an IL-7R binding polypeptide.

In a further aspect of the invention there is provided a method of treating or preventing inflammatory bowel disease and/or mucositis comprising orally administering to a person in need thereof a composition comprising a TNF-alpha binding polypeptide and an IL-7R binding polypeptide.

In the embodiments above, the inflammatory disease is suitably mucositis or oesophagitis and the inflammatory bowel disease is suitably Crohn's disease, ulcerative colitis or check-point inhibitor induced colitis, most suitably ulcerative colitis or Crohn's disease. Furthermore, in the embodiments above, the TNF-alpha binding polypeptide is suitably a polypeptide comprising an antibody fragment and/or the IL-7R binding polypeptide is suitably a polypeptide comprising an antibody fragment. More suitably, the TNF-alpha binding polypeptide and the IL-7R binding polypeptide are both polypeptides comprising an antibody fragment. More suitably, both polypeptides are ICVDs.

Administration of one binding polypeptide 'together' with another binding polypeptide means that the therapeutic windows of each binding polypeptide overlap with each other. This means that, for example, a therapeutically effective amount of each binding polypeptide is present in the body of the subject at the same time. In a particular embodiment, a therapeutically effective amount of each binding polypeptide is present at the site of therapeutic need at the same time.

A therapeutically effective amount of a composition of the invention is an amount which is effective, upon single or multiple dose administration to a subject, in neutralising the biological effects of a chosen target to a significant extent in a subject. A therapeutically effective amount may vary according to factors such as the disease state, age, sex, and weight of the individual, and the ability of the construct to elicit a desired response in the individual. A therapeutically effective amount is also one in which any toxic or detrimental effects of the construct are outweighed by the therapeutically beneficial effects. The composition of the invention can be incorporated into pharmaceutical compositions suitable for oral administration to a subject.

A composition of the invention may be formulated for oral delivery. The compositions of the invention may be in a variety of forms. These include, for example, liquid, semi-solid and solid dosage forms, such as liquid solutions, dispersions or suspensions, tablets, pills and powders. Solid dosage forms are preferred. Suitably the composition of the invention is provided in a tablet, more suitably a minitablet. Suitably the construct of the invention is provided in a tablet, more suitably a minitablet, for the treatment of ulcerative colitis or Crohn's disease. More suitably the construct of the invention is provided in a minitablet with an enteric coating for oral administration.

For the treatment of eosinophilic esophagitis, delivery in the form of a lozenge is particularly preferred. For the treatment of atopic dermatitis, delivery in the form of a cream is particularly preferred.

The composition may comprise a pharmaceutically acceptable excipient, and suitably may be used in the form of ingestible tablets, buccal tablets, troches, capsules, elixirs, suspensions, syrups, wafers, and the like.

Typically, the composition comprises a pharmaceutically acceptable excipient such as a carrier, forming a pharmaceutical composition. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids. Suitably, the polypeptides in the composition of the invention are lyophilised before being incorporated into a pharmaceutical composition.

A composition of the invention may also be provided with an enteric coating. An enteric coating is a polymer barrier applied on oral medication which protects the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the composition of the invention will be released at about the time that the dosage reaches the target region of the intestinal tract.

The pharmaceutical composition of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary concentrations of polypeptide in a pharmaceutical composition may range from about 1 mg/mL to about 200 mg/ml or from about 50 mg/mL to about 200 mg/mL, or from about 150 mg/mL to about 200 mg/mL.

An aqueous formulation of the pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylenepolyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptides against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the pharmaceutical composition of the invention are those to produce the desired therapeutic effect. The dosage range required depends on the precise nature of the pharmaceutical composition or construct, the target region of the intestinal tract, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of pharmaceutical composition of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week.

The TNF-alpha binding polypeptide and the IL-7R binding polypeptide, when present in the inventive composition and when not linked to each other, may be present in a TNF-alpha binding polypeptide to IL-7R binding polypeptide molar ratio of 20:1 to 1:20, such as 15:1 to 1:15, more suitably 10:1 to 1:10, more suitably 5:1 to 1:5, more suitably 3:1 to 1:3, more suitably 2:1 to 1:2, more suitably 1.5:1 to 1:1.5, most suitably about 1:1.

Treatment of diseases also embraces treatment of exacerbations thereof, amelioration of symptoms thereof and also embraces treatment of patients in remission from disease symptoms to prevent relapse of disease symptoms.

Combination Therapy

A pharmaceutical composition of the invention may also comprise one or more active agents (e.g. active agents suitable for treating diseases such as those mentioned herein). It is within the scope of the invention to use the pharmaceutical composition of the invention in therapeutic methods for the treatment of autoimmune and/or inflammatory diseases as an adjunct to, or in conjunction with, other established therapies normally used in the treatment of bacterial, autoimmune and/or inflammatory diseases.

For the treatment of inflammatory bowel disease (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL-23p19 specific antibodies (eg brazikumab, risankizumab or mirikizumab), anti-IL6R antibodies or small molecule IL12/IL23 inhibitors (e.g., apilimod); anti-oncostatin M antibodies, anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK1 inhibitors (e.g., filgotinib or upadacitinib); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are JAK1 inhibitors (e.g., filgotinib or upadacitinib); JAK3 inhibitors (e.g., tofacitinib or R348), anti-IL12/IL23 antibodies (e.g., ustekinumab); anti-IL-23p19 specific antibodies (eg brazikumab, risankizumab or mirikizumab) or anti-alpha-4-beta-7 antibodies (e.g., vedolizumab).

Hence another aspect of the invention provides a pharmaceutical composition of the invention in combination with one or more further active agents, for example one or more active agents described above. In a further aspect of the invention, the pharmaceutical composition or construct is administered sequentially, simultaneously or separately with at least one active agent selected from the list above.

Similarly, another aspect of the invention provides a combination product comprising:

(A) a pharmaceutical composition of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a pharmaceutical composition or construct of the present invention and another therapeutic agent, in admixture with a pharmaceutically acceptable adjuvant, diluent or carrier.

The invention also encompasses a kit of parts comprising components:

(i) a pharmaceutical composition of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of bacterial infection such as *Clostridium difficile* infection, autoimmune and/or inflammatory diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Vectors and Hosts

The term "vector", as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode the polypeptides in the composition of the invention. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a vector comprising the polynucleotide encoding a construct of the invention or cDNA comprising said polynucleotide. In a further aspect of the invention there is provided a host cell transformed with said vector, which is capable of expressing the construct of the invention. Suitably the host cell is a yeast such as a yeast belonging to the genera *Aspergillus, Saccharomyces, Kluyveromyces, Hansenula* or *Pichia*, such as *Saccharomyces cerevisiae, Escherichia coli* or *Pichia pastoris*.

Preparative Methods

Polypeptides and constructs comprising polypeptides can be obtained and manipulated using the techniques disclosed for example in Green and Sambrook 2012.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Köhler et al., 1975 and Nelson et al., 2000, herein incorporated by reference in their entirety).

A monoclonal antibody directed against a determined antigen can, for example, be obtained by:
a) immortalizing lymphocytes obtained from the peripheral blood of an animal previously immunized with a determined antigen, with an immortal cell and preferably with myeloma cells, in order to form a hybridoma,
b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:
a) cloning into vectors, especially into phages and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection,
d) recovering the antibodies having the desired specificity.

Methods for immunizing camelids, cloning the VHH repertoire of B cells circulating in blood (Chomezynnski et al., 1987), and isolation of antigen-specific VHHs from immune (Arbabi-Ghahroudi et al., 1997) and nonimmune (Tanha et al 2002) libraries using phage, yeast, or ribosome display are known (WO92/01047, Nguyen et al., 2001 and Harmsen et al., 2007. These references are herein incorporated by reference in their entirety.

Antibody fragments such as the scFv and Fv fragments can be isolated and expressed in *E. coli* (Miethe et al., 2013, Skerra et al., 1988 and Ward et al., 1989, herein incorporated by reference in their entirety).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli, P. pastoris* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984, Sakamar et al., 1988, Wells et al., 1985 and Grundstrom et al., 1985, herein incorporated by reference in their entirety). A gene encoding a polypeptide can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma et al., 1998)

Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:

a) cloning in a Bluescript vector (Agilent Technologies) a DNA or cDNA sequence coding for the VHH (for example obtained from lymphocytes of camelids or produced synthetically) optionally including a His-tag, b) recovering the cloned fragment after amplification using a 5' primer specific for the VHH containing an XhoI site and a 3' primer containing the SpeI site having the sequence TC TTA ACT AGT GAG GAG ACG GTG ACC TG (SEQ ID NO: 13), c) cloning the recovered fragment in phase in the Immuno PBS vector (Huse et al., 1989, herein incorporated by reference in its entirety) after digestion of the vector with XhoI and SpeI restriction enzymes, d) transforming host cells, especially *E. coli* by transfection with the recombinant Immuno PBS vector of step c, e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:

a) obtaining a DNA or cDNA sequence coding for a VHH, having a determined specific antigen binding site, b) amplifying the obtained DNA or cDNA, using a 5' primer containing an initiation codon and a HindIII site, and a 3' primer containing a termination codon having a XhoI site, c) recombining the amplified DNA or cDNA into the HindIII (position 2650) and XhoI (position 4067) sites of a plasmid pMM984 (Merchlinsky et al., 1983, herein incorporated by reference in its entirety), d) transfecting permissive cells especially NB-E cells (Faisst et al., 1995, herein incorporated by reference in its entirety) with the recombinant plasmid, e) recovering the obtained products.

Further, immunoglobulin chain variable domains such as VHHs or VHs can be produced using *E. coli* or *S. cerevisiae* according to the methods disclosed in Frenken et al., 2000 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski et al., 1987), and first strand cDNA synthesis (e.g. using a cDNA kit such as RON 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 bp are purified via agarose gel electrophoresis and ligated in the *E. coli* phagemid vector pUR4536 or the episomal *S. cerevisiae* expression vector pUR4548, respectively. pUR4536 is derived from pHEN (Hoogenboom et al., 1991, herein incorporated by reference in its entirety) and contains the lacI$^q$ gene and unique restriction sites to allow the cloning of the llama VHH and VH genes. pUR4548 is derived from pSY1 (Harmsen et al., 1993, herein incorporated by reference in its entirety). From this plasmid, the BstEII site in the leu2 gene is removed via PCR and the cloning sites between the SUC2 signal sequence and the terminator are replaced in order to facilitate the cloning of the VH/VHH gene fragments. The VH/VHHs have the c-myc tag at the C-terminus for detection. Individual *E. coli* JM109 colonies are transferred to 96 well microtiter plates containing 150 ml 2TY medium supplemented with 1% glucose and 100 mg L$^{-1}$ ampicillin. After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual *S. cerevisiae* colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGal medium (comprising 1% yeast extract, 2% bacto peptone and 5% galactose). After 24 and 48 h of growth, the cells are pelleted and the culture supernatant can be analysed in an ELISA. Absorbance at 600 nm (OD600) is optionally measured.

Further, immunoglobulin chain variable domains such as VH/VHHs can be produced using *S. cerevisiae* or *P. pastoris* using the procedure as follows:

Isolate a naturally-occurring DNA sequence encoding the VH/VHH or obtain a synthetically produced DNA sequence encoding the VH/VHH, including a 5'-UTR, signal sequence, stop codons and flanked with SacI and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1×TAE buffer and then perform gel extraction for example using QIAquick Gel Extraction Kit (Qiagen)). Set-up a ligation of digested MCI vector and digested DNA encoding the VH/VHH as follows: 100 ng vector, 30 ng VHH gene, 1.5 ul 10×ligase buffer, 1 ul T4 DNA ligase, and ddH$_2$O. Then perform ligation overnight at 16 degrees C.

Next transform the *E. coli* cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 *E. coli* cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into *E. coli* as detailed above, *S. cerevisiae* or *P. pastoris* can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semi-permeable so the DNA can pass the membrane.

Preparation for yeast transformation: perform a HpaI digestion of the midi-prep prepared from the selected *E. coli* colony expressing the VH/VHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20×YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YPD (Yeast Extract Peptone Dextrose) overnight at 30 degrees C. Next day prepare about 600 ml YPD and use to fill 3 flasks with 275 ml, 225 ml and 100 ml YPD. Add 27.5 ul yeast YPD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing: 240 ul PEG, 50 ul cells, 36uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatorgraphy with a strong anion resin (such as Capto S). On day 1, inoculate the selected yeast colony expressing the VH/VHH in 5 ml YPD medium (YP medium+2% glucose) and grow the cells in 25 mL sealed sterile tubes at 30 degrees C. overnight (shaking at 180 rpm). On day 2, dilute the 5 ml overnight culture in 50 mL freshly prepared YP medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al., 1985 (herein incorporated by reference in its entirety). Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptides can be produced in a fungus such as a yeast (for example, *S. cerevisiae* or *P. pastoris*) comprising growth of the fungus on a medium comprising a carbon source wherein 50-100 wt % of said carbon source is ethanol, according to the methods disclosed in WO02/48382. Large scale production of VHH fragments in *S. cerevisiae* is described in Thomassen et al., 2002 (herein incorporated by reference in its entirety).

In one aspect of the invention there is provided a method of making a composition of the invention comprising the step of expressing a polynucleotide encoding a TNF-alpha binding polypeptide using a suitable host and expressing a polynucleotide encoding an IL-7R binding polypeptide in a suitable host and adding both polypeptides to a composition. In a further aspect of the invention there is provided a method of making a construct of the invention comprising the step of expressing a polynucleotide encoding a construct of the invention using a suitable host.

Further embodiments of the invention are set out in the following clauses.

CLAUSES

1. A composition comprising a TNF-alpha binding polypeptide and an IL-7R binding polypeptide.
2. The composition according to clause 1 wherein:
    (a) the TNF-alpha binding polypeptide comprises three complementarity determining regions (CDR1-CDR3), wherein CDR1 comprises a sequence sharing 60% or greater sequence identity with SEQ ID NO: 1, CDR2 comprises a sequence sharing 50% or greater sequence identity with SEQ ID NO: 2 and CDR3 comprises a sequence sharing 60% or greater sequence identity with SEQ ID NO: 3; and
    (b) the IL-7R binding polypeptide comprises three complementarity determining regions (CDR1-CDR3), wherein CDR1 comprises a sequence sharing 60% or greater sequence identity with SEQ ID NO: 9, CDR2 comprises a sequence sharing 50% or greater sequence identity with SEQ ID NO: 10 and CDR3 comprises a sequence sharing 60% or greater sequence identity with SEQ ID NO: 11.
3. The composition according to either clause 1 or 2 wherein the polypeptide comprising an antibody fragment is an immunoglobulin chain variable domain.
4. The composition according to any one of clauses 1 to 3 wherein the TNF-alpha binding polypeptide binds to TNF-alpha with a Kd of $10^{-7}$ M or less and the IL-7R binding polypeptide binds to IL-7R with a Kd of $10^{-7}$ M or less.
5. The composition according to any one of clauses 1 to 4 wherein the TNF-alpha binding polypeptide neutralizes human TNF-alpha cytotoxicity in an L929 assay with an EC50 of 100 nM or less and the IL-7R binding polypeptide neutralizes IL-7R-dependent, IL-7-induced STAT5 phosphorylation in human lymphocytes with an EC50 of 100 nM or less.
6. The composition according to any one of clauses 1 to 5 wherein the TNF-alpha binding polypeptide and the IL-7R binding polypeptide are linked.
7. The composition according to clause 6 wherein the TNF-alpha binding polypeptide and the IL-7R binding polypeptide are linked by a protease-labile peptide linker.
8. The composition according to clause 7 wherein the protease-labile peptide linker comprises a K and/or R residue.
9. The composition according to any one of clauses 1 to 8 wherein the polypeptides are substantially resistant to one or more proteases present in the small or large intestine.
10. A pharmaceutical composition comprising the composition according to any one of clauses 1 to 9 and a pharmaceutically acceptable excipient.
11. The composition according to any one of clauses 1 to 10 wherein the composition comprises an enteric coating.
12. The composition according to any one of clauses 1 to 11 wherein the composition is suitable for oral administration.
13. The composition according to any one of clauses 1 to 12 for use in the treatment or prevention of an autoimmune disease and/or inflammatory disease.
14. A TNF-alpha binding polypeptide for use in the treatment or prevention of an autoimmune disease and/or inflammatory disease, together with an IL-7R binding polypeptide.
15. An IL-7R binding polypeptide for use in the treatment or prevention of an autoimmune disease and/or inflammatory disease, together with a TNF-alpha binding polypeptide.

The present invention will now be further described by means of the following non-limiting examples.

EXAMPLES

Examples 1 to 3 provide information on the properties of specific IL-7R binding polypeptides. Examples 4 and 5 provide information on experiments involving IL-7R binding polypeptides and TNF-alpha binding polypeptides used in conjunction. Example 6 details the production of a construct comprising an IL-7R binding polypeptide and a TNF-alpha binding polypeptide.

Example 1: Potency of IL-7R Binding Polypeptides ID-A40U, V7R-2E9 and ID-A62U, Compared to an IL-7R Binding Polypeptide of the Prior Art The inhibitory potency and efficacy (maximal inhibition) of IL-7R binding polypeptides ID-A40U (SEQ ID NO: 24) and V7R-2E9 (SEQ ID NO: 25), both produced in *E. coli*, were assayed in vitro in an L-7/IL-7R neutralisation ELISA and compared to mAb829, a clinical anti-IL-7R antibody (also known as "GSK2618960", an anti-IL-7Ra monoclonal antibody disclosed in Ellis et al 2019).

A 7-point dilution series of ICVDs was prepared in 1% BSA (at 2× the assay concentration) starting at 300 nM and using a 3.2 dilution factor. A mAb829 comparator antibody was used as a positive control in the ELISA with a concentration range between 10 nM and 0.088 nM (2× the assay concentration). Volumes sufficient for triplicates were prepared for each ICVD dilution, while a volume sufficient for 2 triplicates (2 plates) was prepared for mAb829. 85 μL (or 170 μL) of each ICVD (or mAb829) dilution were mixed with 85 μL (or 170 μL) of 10 ng/mL IL-7 (2× the assay concentration). 85 μL of IL-7 were mixed with 85 μL of block buffer to have the IL-7 (1×) full binding signal in each plate. Block buffer alone was also added to each plate as blank. Bound IL-7 was then measured using biotinylated anti-hIL-7 followed by Extravidin-HRP. TMB reaction was stopped after 30 minutes.

$EC_{50}$ values were generated in Graphpad prism using the ELISA signal blank corrected A450 data and 'log (inhibitor) vs. response—Variable slope (four parameters)' to fit curves and generate EC50.

In addition, the ability of ID-A40U and V7R-2E9 to inhibit IL-7 binding to IL-7Ra and hamper STAT5 phosphorylation was tested, in vitro, in human lymphocytes. Human peripheral blood mononuclear cells (PBMCs) respond to exogenous IL-7 by stimulation of intracellular STAT5 phosphorylation though IL-7R signalling but this response can be negated by IL-7Ra-specific ICVDs that prevent IL-7/IL-7R binding.

A lymphocyte enriched population was isolated from human buffy coat and stored in 90% FBS 10% DMSO in liquid nitrogen. Cells were thawed and rested, for recovery, in complete RPMI-1640. After recovery, cells were plated in a round-bottom 96 well plate in 100p1, $2.5 \times 10^5$ cells/well and starved for 1 h in complete RPMI without FBS. After starvation, the desired ICVD concentrations were added to each well (50 μL/well), and plate incubated for 15 min at room temperature. Then 50 μL/well of IL-7 was added to each well and plate incubated for 15 min at 37° C. 5% $CO_2$. Reaction was stopped by quickly chilling the plate on ice followed by centrifugation and supernatant removal. Cells were then processed for fixation, permeabilization and pSTAT5 intracellular staining. Cells were incubated for 20 min on ice with 100 μL/well Cytofix/Cytoperm solution (BD Bioscience #554722), washed twice with 150p1/well 1×Perm/Wash buffer (BD Bioscience #554723), incubated on ice for 30 min with 200 μL/well Perm buffer III (BD Bioscience #558050) and washed twice with 150 μL/well of 1×PBS 2% BSA (FACS buffer). Cells were subsequently stained for 1 h room temperature with 25 μL/well of pSTAT5 antibody ([47/Stat5(pY694)] (A488) (BD Bioscience #612598)) or the isotype control Mouse IgG1 ([B11/6] (FITC) (Abcam #ab91356)). Reaction was stopped by adding 150 μL/well of FACS buffer. After 1 wash/centrifugation step, cells were finally resuspended in 200 μL/well of FACS buffer and data acquired in the CytoFlex flow cytometer (Beckman Coulter). Data analysis was performed using the FlowJo software.

The results of these experiments shown in Table 1a, alongside the comparator.

TABLE 1a

| Construct | IL-7/IL-7R ELISA $EC_{50}$ nM | IL-7 induced pSTAT5 in hPBMCs $EC_{50}$ nM |
|---|---|---|
| ID-A40U | 0.544 | 1-2 |
| V7R-2E9 | 0.818 | 2.86 |
| mAb829 | 0.8 | 2.6 |

In separate experiments, this same IL-7/IL-7R neutralisation ELISA was performed on ID-A62U (SEQ ID NO: 16) (produced in *S. cerevisiae*) alongside a comparator. The results are shown in Table 1b. ID-A62U comprises E1D and R45L mutations relative to ID-A40U.

TABLE 1b

| Construct | IL-7/IL-7R ELISA $EC_{50}$ nM |
|---|---|
| ID-A62U | 0.4 |
| mAb829 | 0.424 |

The ability of V7R-2E9 to neutralise the L-TSLP/TSLP-R complex binding to IL-7Ra was tested. 96-well plates were coated with 0.25 μg/mL recombinant human IL-7Ra-His$_6$-Fc+5 μg/mL BSA and then blocked. V7R-2E9 was serially diluted and mixed 1:1:1 with recombinant human L-TSLP (15 ng/mL final concentration) and human TSLP-R (20 ng/mL final concentration). Then the mixtures were incubated for 30 minutes to allow binding before adding to the IL-7Ra coated plates. Following 2 hours' incubation, bound L-TSLP was detected with 50 μL/well 0.3 μg/mL Biotinylated Rabbit anti-hTSLP antibody and then 50 μL/well 1/2000 Extravidin-HRP, and levels of neutralisation of L-TSLP/TSLP-R complex binding to IL-7Ra by the ICVD was determined using GraphPad Prism. The results are shown in Table 1c below.

TABLE 1c

| Construct | TSLP/TSLPR/IL-7R ELISA $EC_{50}$ nM |
|---|---|
| ID-A62U | 0.74 |
| mAb829 | 0.99 |

In summary, ID-A62U and ID-A40U were demonstrated to have comparable or greater potency than comparator clinical anti-IL-7R antibody mAb829. It is noteworthy that both ID-A40U and ID-A62U, which belong to the same family of ICVD, maintain high potency even though they do not have identical sequences (ID-A62U comprises E1D and R45L mutations relative to ID-A40U) and are produced using different organisms.

Example 2: Biacore Estimation of ICVD—IL-7R Binding Affinity

The binding kinetics of ID-A40U were compared against the mAb829 clinical antibody in a Biacore study. The IL-7Ra-His$_6$-Fc was coated directly on the Biacore sensor plate (for mAb829 analysis) or captured by an anti-human IgG Fc (for the ICVD analysis), and ICVD/Ab were flowed over the plate to detect binding. ID-A40U had an affinity (Ko) of $7.8 \times 10^{-11}$ M, and mAb829 had a slightly lower affinity (Ko) of $5.67 \times 10^{-10}$ M. The results indicate that ID-A40U demonstrates strong binding to the antigen. ID-A62U comprises E1D and R45L mutations relative to ID-A40U.

Example 3: Resistance to Gastrointestinal Extracts

Ex vivo incubation in intestinal supernatants can predict the stability of ICVDs in the intestinal tract of cynomolgus monkeys and man. The activities of the major small intestinal proteases, trypsin and chymotrypsin, are conserved across mammalian species, whereas proteases present in the large intestine are likely to be produced by host species-specific gut microflora. To generate testing matrices that reflect these two environments, pooled mouse small intestinal supernatants and pooled faecal supernatants were prepared. Both of these matrices are highly digestive towards unselected, un-engineered ICVDs.

It has previously been shown that the anti-TNF-alpha ICVD ID-38F has high stability in these matrices (see WO2016/156465) and that this property was predictive of high stability during transit through the gut for ID-38F.

V7R-2E9 and ID-A40U were tested for their survival in gastrointestinal extracts from both murine and human sources. ICVDs were incubated for 6 hours at 37° C. with mouse small intestinal supernatants, and 16 hours with human faecal supernatant. Survival was measured by the IL-7/IL-7R neutralising ELISA detailed above under Example 1. Both constructs demonstrated good survival in the digestive matrices tested (FIG. 1, wherein "SI"=mouse small intestinal fluid and "HF"=human faecal supernatant).

Figure 2:
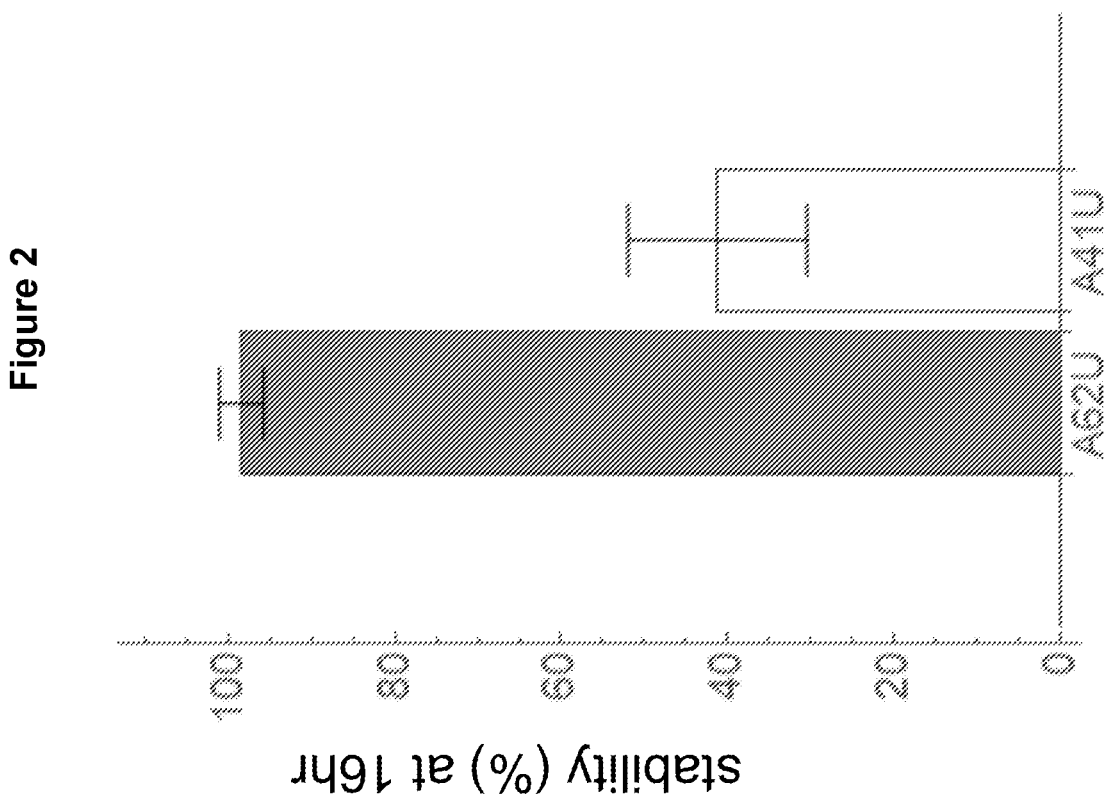
FIG. 2—% survival of ID-A62U and ID-A41U in human faecal supernatant

In a separate experiment, ID-A62U was tested for survival in the same human faecal supernatant assay, alongside ID-A41U (an unstable comparator ICVD). ID-A62U displayed approximately 100% survival compared to approximately 40% survival for ID-A41U (FIG. 2, ID-A62U labelled 'A62U' and ID-A41U labelled 'A41U').

These were stringent tests involving extended incubation periods. Therefore, either of these ICVDs would be expected to survive very well in the gastrointestinal environment.

Example 4: Investigation of the Inhibitory Effects of a TNF-Alpha Binding Polypeptide and an IL-7R Binding Polypeptide, Administered Separately and in Combination, on the Phosphorylation of Signalling Proteins in Ex Vivo Cultured IBD Tissue A study was conducted to investigate the inhibitory effects of a TNF-alpha binding polypeptide and an IL-7R binding polypeptide on the levels of phosphoprotein biomarkers and the spontaneous production of inflammatory cytokines in ex vivo cultures of inflamed colonic mucosal tissue obtained from patients with UC. The polypeptides tested were both ICVDs. The ICVDs were ID-A62U (an IL-7R binding ICVD discussed in Examples 1-3 above) and ID-38F (a TNF-alpha binding ICVD disclosed in WO2016/156465). Effects of the individual ICVDs were compared with a mixture of the two ICVDs together and a negative control ICVD ("ID-2A", an irrelevant ICVD which binds to neither target) to assess the effects of combining the different anti-cytokine mechanisms.

Figure 3:
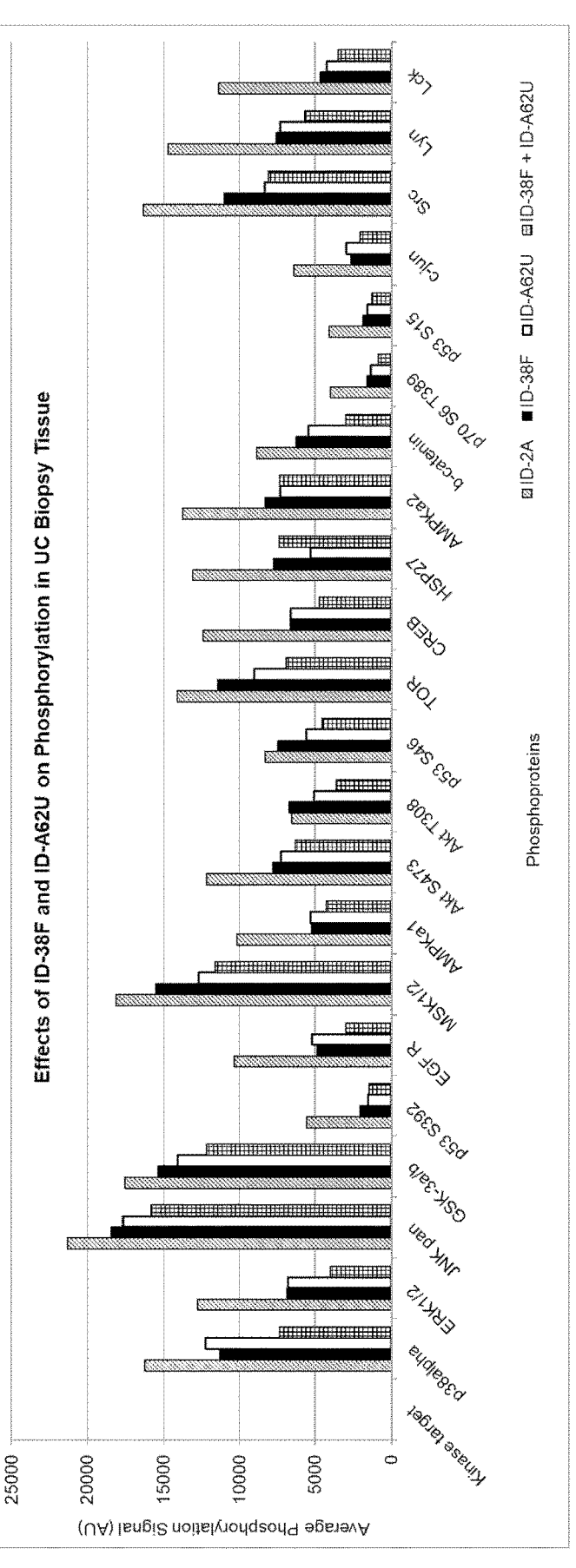
FIG. 3—Effects of combined ID-38F and ID-A62U on phosphorylation in UC biopsy tissue (phosphoproteins p38alpha to Lck)
Figure 4:
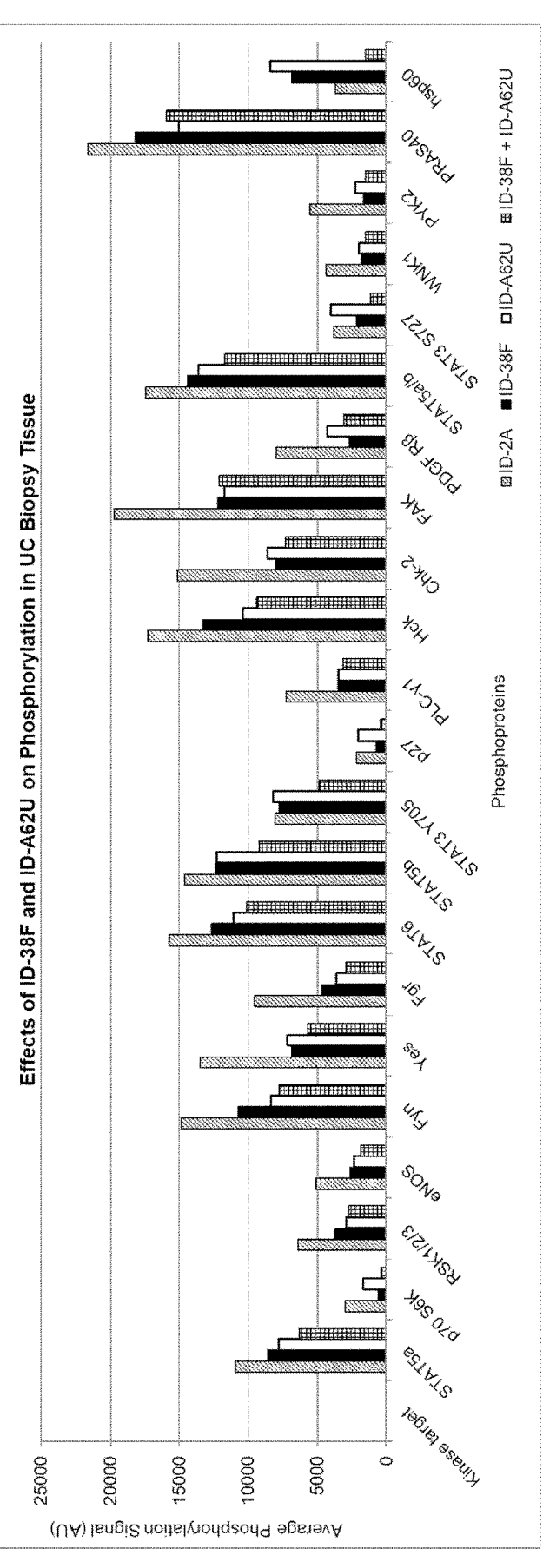
FIG. 4—Effects of combined ID-38F and ID-A62U on phosphorylation in UC biopsy tissue (phosphoproteins STAT5a to hsp60)

Biopsies from each of four different UC patients were incubated for 24 hours with the different ICVDs (control ID-2A 50 nM, ID-38F 50 nM, ID-A62U 50 nM or ID-38F+ ID-A62U, each 50 nM) and following treatment, the tissue lysates were analysed on phosphoprotein antibody arrays. The resultant histograms (FIGS. 3-4) provide a visual representation of the combined phospho-intensity data obtained for each of the biopsies (4 per treatment). The inhibitory effects of the different ICVD treatments are demonstrated by a shift from predominantly high phospho-intensity values for biopsies treated with the control ICVD ID-2A, to relatively low phospho-intensity values for biopsies treated with the anti-TNF-alpha or anti-IL-7R ICVD or a combination of the two. These mean results show consistent overall inhibitory effects of ID-A62U and ID-38F on tissue phosphorylation levels with a greater effect when the two ICVDs were combined. It is not known which, if any, of the phosphoproteins might be more important in this analysis so the overall effects of treatment on protein phosphorylation in each biopsy were assessed.

Figure 5:
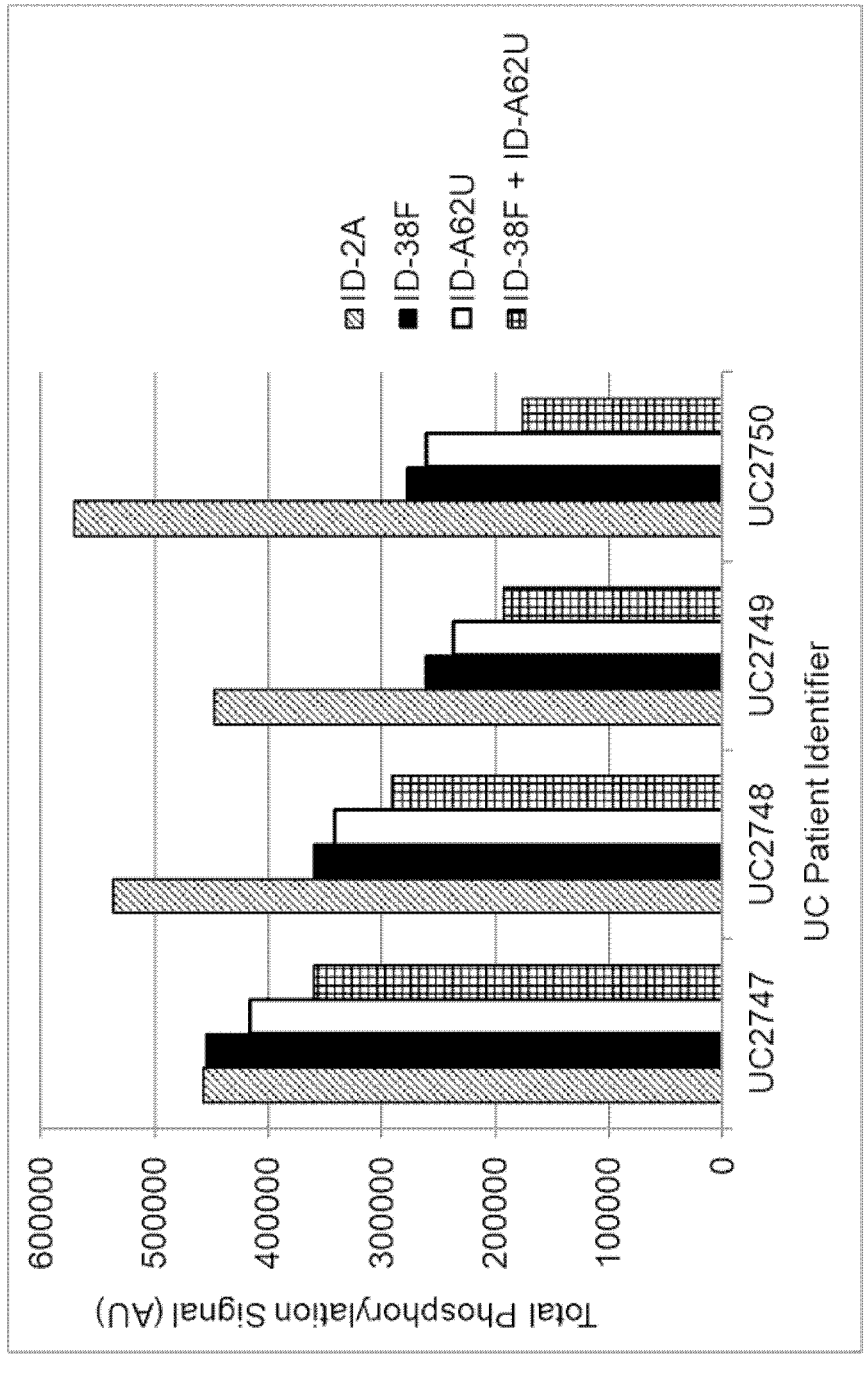
FIG. 5—Total phospho-intensity values measured for biopsies from patients UC2747, UC2748, UC2749 and UC2750 after treatment with separate and combined agents FIG. 6—Mean cytokine production measured for biopsies from all patients after treatment with separate and combined agents (IL-1β and IL-6)

Results presented in FIG. 5 show the total phospho-intensity values measured for the four biopsies from each patient. For each biopsy, a total phosphorylation level was calculated by adding together the intensity values measured for all of the 45 proteins on the array. For each patient, the total phosphorylation levels measured for each treatment are shown. Three patients (UC2748, UC2749 and UC2750) showed marked inhibition (about 50% with the combination) while the fourth UC2747 also showed marked inhibition but was generally less responsive.

The combined inhibitory effects of treatment with ID-38F plus ID-A62U exceeded those achieved with the single ICVDs and resulted in close to maximal inhibition of most of the phosphoproteins. Due to the unexpectedly high levels of inhibition observed in this experiment, definitive evidence for synergistic effects of the combined agents in UC tissue will need to be explored further. However, evidence for the marked inhibition of inflammatory biomarkers in UC tissue by IL-7R and TNF-alpha binding polypeptides is encouraging and suggests good potential for observable synergy when lower concentrations of the polypeptides are combined.

Overall, these results demonstrate at least additive, and potentially synergistic, effects of co-administered anti-TNF-alpha and anti-IL-7R polypeptides.

Figure 6:
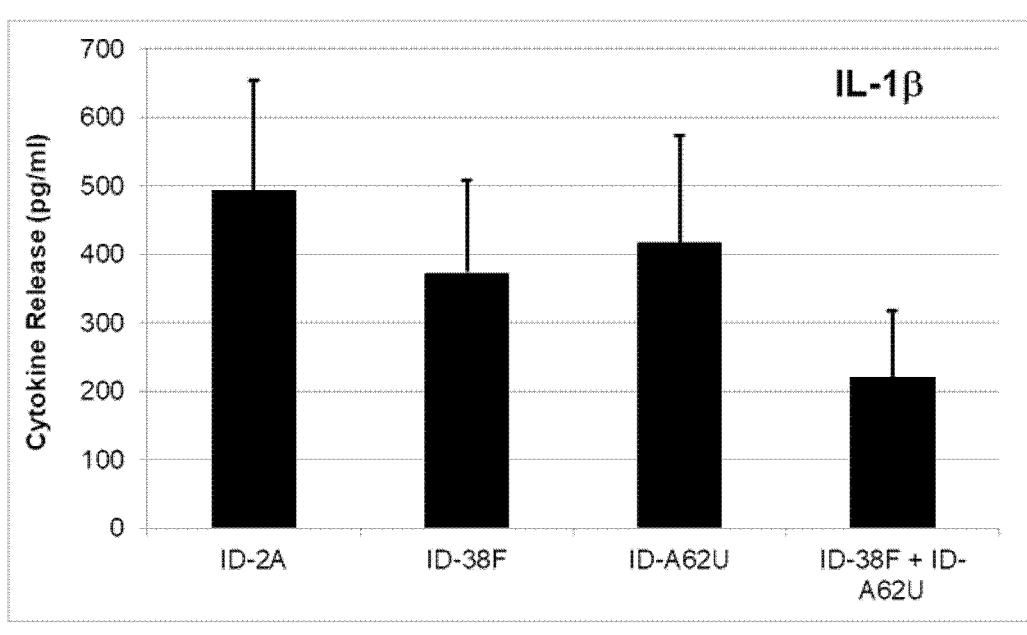
Figure 6:
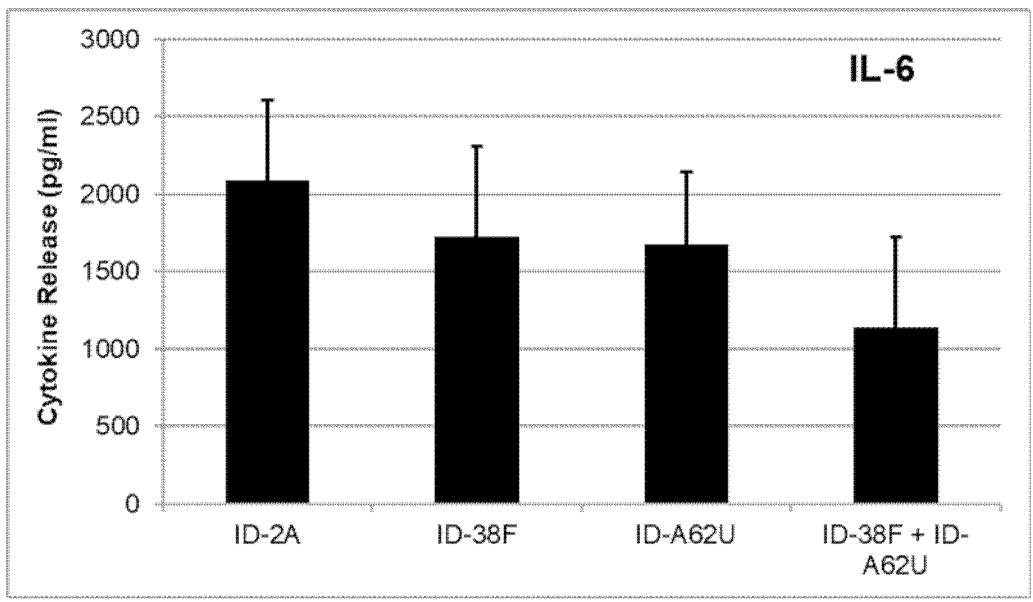
Figure 7:
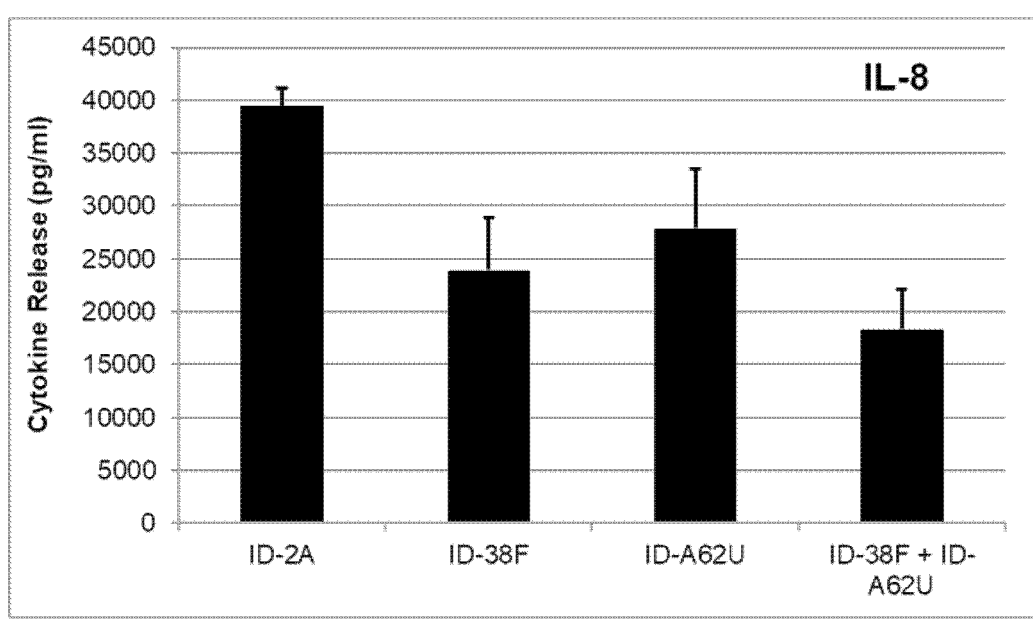
FIG. 7—Mean cytokine production measured for biopsies from all patients after treatment with separate and combined agents (IL-8 and TNF-alpha)
Figure 7:
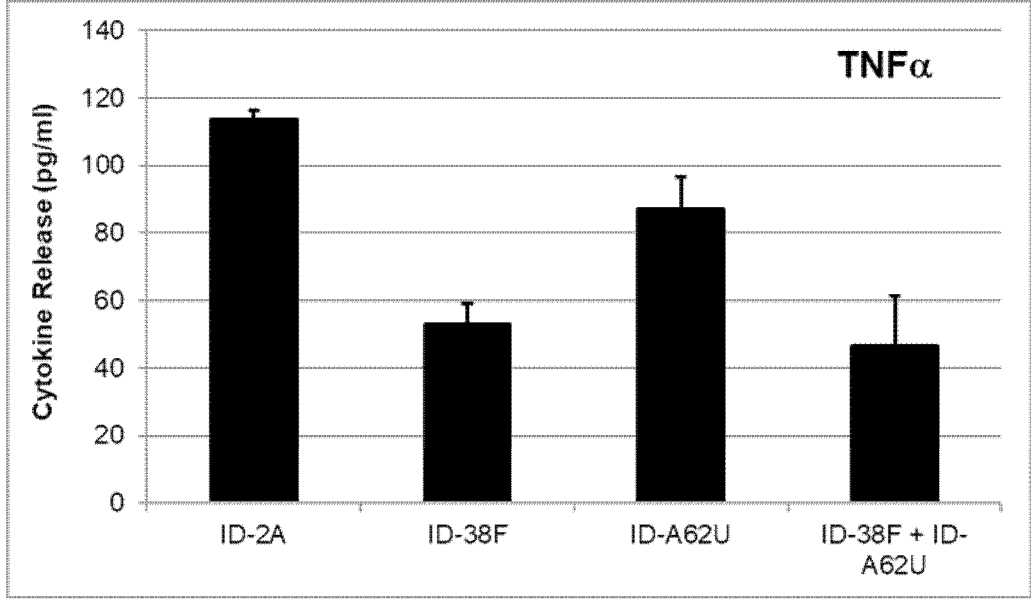
Figure 8:
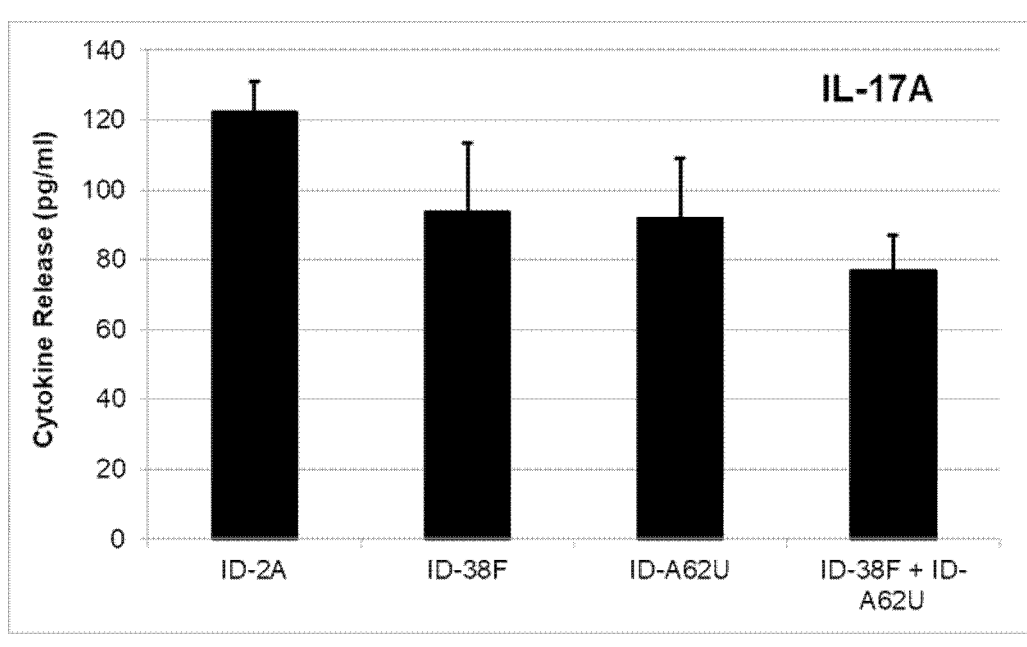
FIG. 8—Mean cytokine production measured for biopsies from all patients after treatment with separate and combined agents (IL-17A and IL-10)
Figure 8:
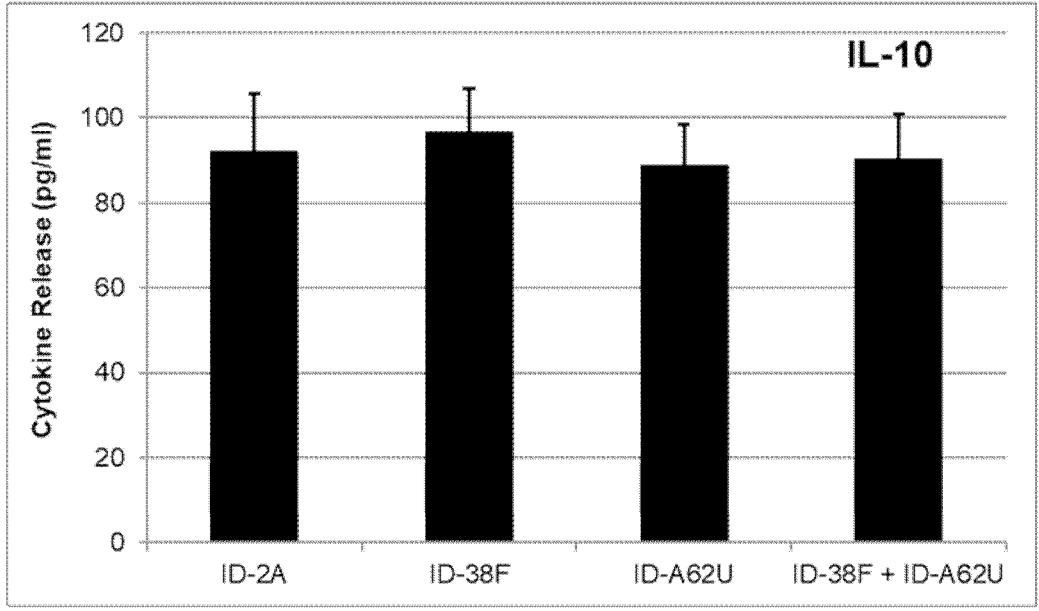

Example 5: Investigation of the Inhibitory Effects of a TNF-Alpha Binding Polypeptide and an IL-7R Binding Polypeptide, Administered Separately and in Combination, on the Production of Cytokines in Ex Vivo Cultures of IBD Tissue The effects of the different treatments on mean spontaneous cytokine production in the biopsies discussed under Example 4 above are presented in FIGS. 6-8. ID-38F or ID-A62U treatment alone inhibited the production of IL-8, TNFα and IL-17F but had little effect on other cytokines. However, when ID-38F and ID-A62U were combined the inhibitory effects on IL-1β, IL-6, IL-8, IL-17A and IL-33 were clearly greater than those seen with the individual ICVDs. Inhibitory effects of the combination on TNFα and IL-17F production were no greater than those of the individual ICVDs noted above.

In conclusion, results obtained for three of the patients in this study showed that individually, treatments with either ID-38F or ID-A62U inhibited production of some proinflammatory cytokines (IL-8, TN Fa, IL-17F). The inhibitory effects on other cytokines were small/partial, and this probably reflected the sub-maximal concentrations of the ICVDs chosen for this study. Importantly, when the two ICVDs were combined, the inhibitory effects on the production of most cytokines including IL-1β, IL-6, IL-8, IL-17A and IL-33 were increased.

Overall, these results demonstrate at least additive, and potentially synergistic, effects of co-administered anti-TNF-alpha and anti-IL-7R polypeptides.

Example 6: Production, Cleavage and Testing of a Heterobihead Comprising a TNF-Alpha Binding Polypeptide and an IL-7R Binding Polypeptide Linked by a Labile Linker A bihead construct called "FU3K" was produced combining ID-38F and ID-A62U, separated by a flexible $(G_4S)_2$ linker with a central lysine (K) residue (SEQ ID NO: 21) to create a trypsin-cleavable site.

FU3K was cloned on a Sad/HindIII fragment into vector pUR9013 to facilitate stable, multi-copy, integration into the chromosome of an *S. cerevisiae* expression strain. This was achieved following standard cloning procedures. Using this integration and expression system, FU3K was under the control of a galactose-inducible promoter and bihead secretion was achieved via a yeast mating factor alpha signal sequence. Expression of FU3K from the yeast chromosome was assessed in 50 mL induction cultures. Full-length FU3K expressed well in small-scale yeast cultures.

Figure 9:
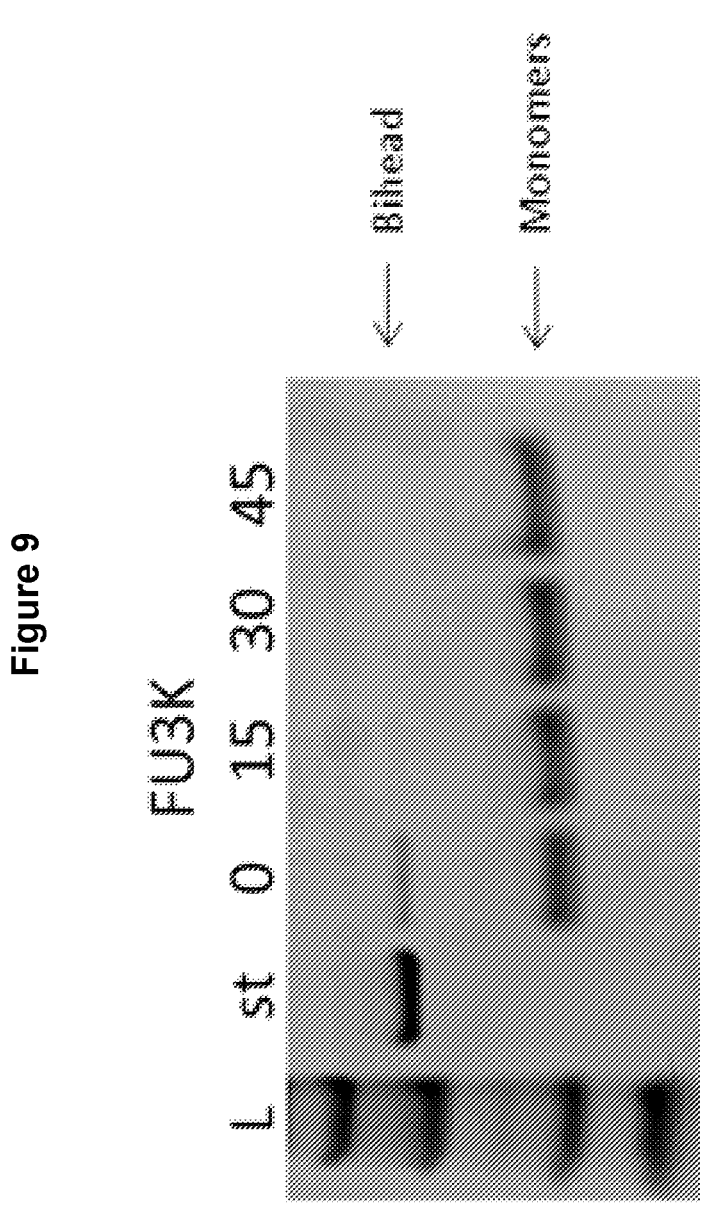
FIG. 9—SDS PAGE analysis of ID-38F and ID-A62U release from bihead construct FU3K before and after trypsin treatment FIG. 10—Potency of FU3K and ID-A62U before and after trypsin treatment using an IL-7/IL-7R ELISA FIG. 11—Potency of FU3K and ID-38F before and after trypsin treatment using a biotinylated Humira competition ELISA FIG. 12—% survival of (a) ID-A62U, (b) ID-38F, (c) ID-A62U and ID-38F after release from FU3K and (d) ID-A41U, in human faecal supernatant

Incubation of FU3K with trypsin at 37° C. resulted in rapid separation of ID-38F and ID-A62U monomer arms. Analysis was conducted by SDS PAGE (FIG. 9, wherein lanes are time in minutes, St=standard (no trypsin added), L=molecular weight marker, equal volumes loaded per lane). Bands corresponding to the uncleaved FU3K bihead (approximately 27 kDa) and cleaved monomers (approximately 13.5 kDa) are clearly visible. This confirms that FU3K is well-formatted for quick release of both monomer arms on exposure to trypsin in the human small intestine, or microbial trypsin-like proteases in the colon.

Figure 10:
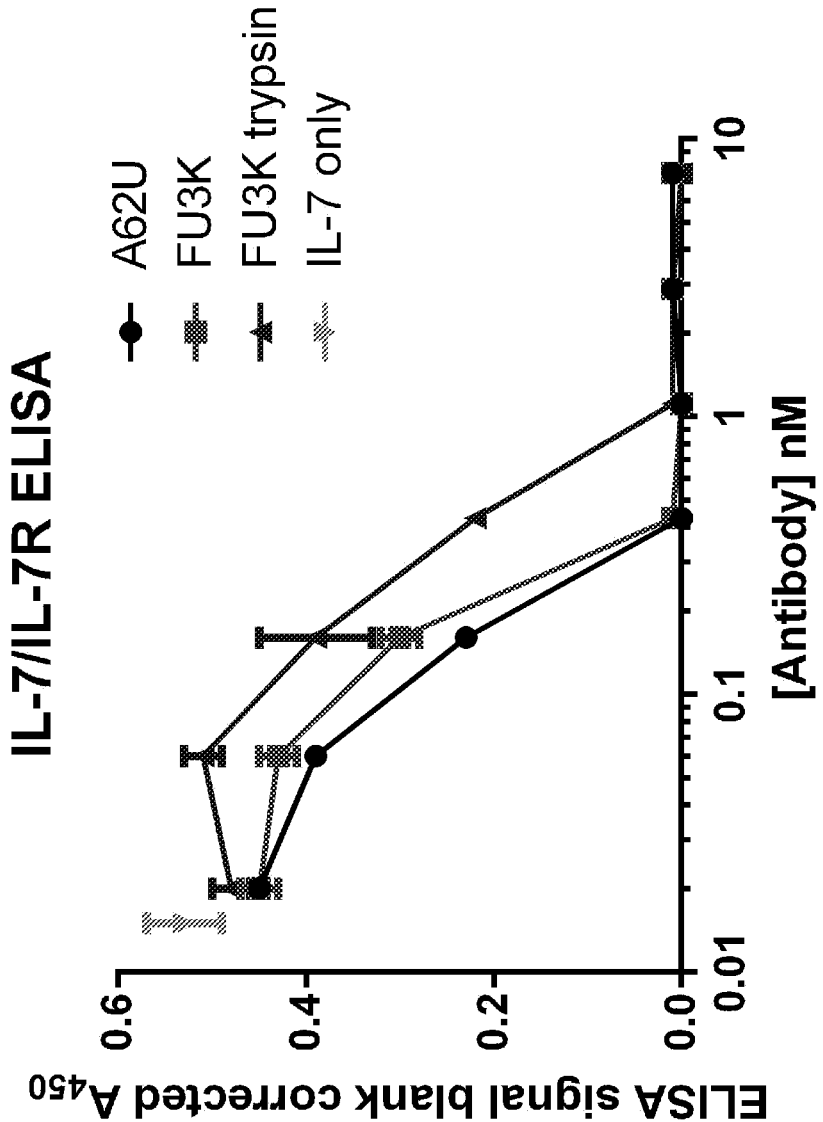

An IL-7/IL-7R ELISA was performed using the method described under Example 1 above. Pre-digestion FU3K was as potent against IL-7R as ID-A62U and post-digestion, FU3K retained high (sub-nanomolar) potency against IL-7R (FIG. 10, ID-A62U labelled "A62U").

A biotinylated Humira competition ELISA was performed to measure competition for the overlapping epitope of ID-38F and Humira on TNFα. ELISA plates were coated with 100 ng/mL human TNFα in 250 µg/mL bovine serum albumin (BSA) in phosphate buffered saline (1×PBS) and blocked with 1% BSA in 1×PBS. Biotinylated adalimumab was mixed 1:1 with all standards and samples to give a final concentration of 2 nM biotinylated adalimumab before adding the mixtures to the plates. Bound biotinylated adalimumab was detected using ExtrAvidin-horseradish peroxidase and visualized using TMB Microwell Substrate before stopping with 0.5M $H_2SO_4$ and reading at 450 nm.

Figure 11:
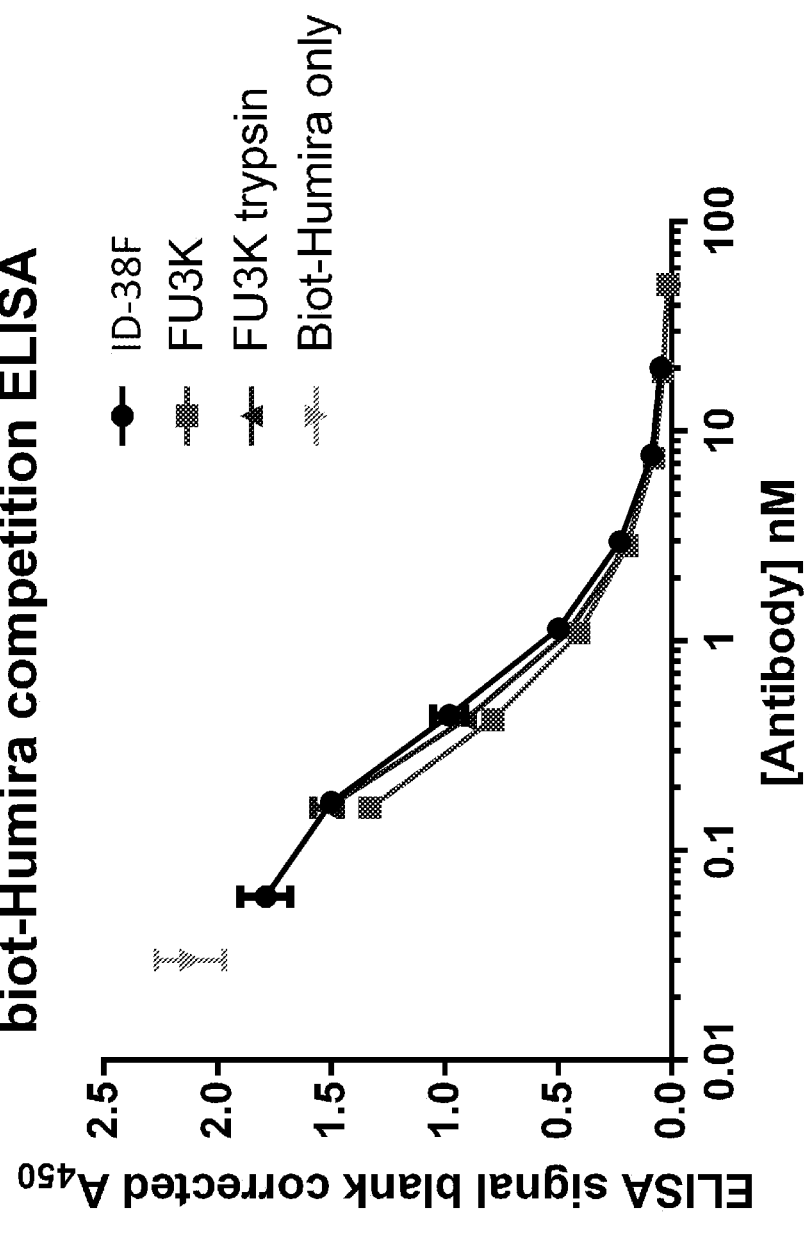

It was found that pre- and post-digestion FU3K was as potent as ID-38F in this competition ELISA (FIG. 11).

Figure 12:
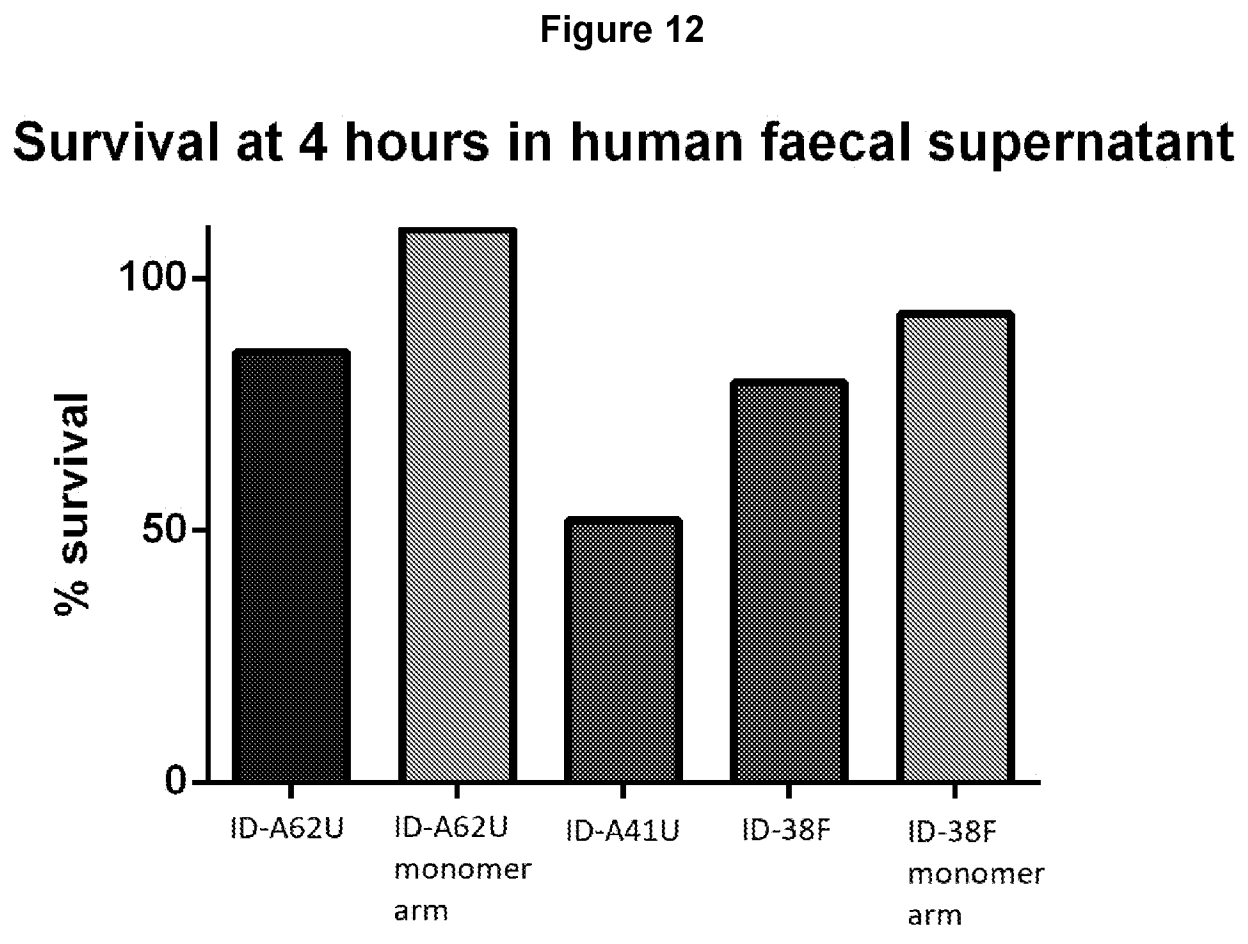

Both of the monomer arms of FU3K were shown to retain the favourable stability characteristics of parent monomers ID-38F and ID-A62U following incubation for 4 hours in human faecal supernatant, performed as described in Example 2 above (FIG. 12).

These data demonstrate that FU3K is a suitable format to deliver high concentrations of each of these monomers as a dual therapy direct to the colon in man.

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

REFERENCES

Arbabi-Ghahroudi et al *FEBS Lett* 1997 414:521-526
Blattler et al *Biochemistry* 1985 24:1517-1524
Binz et al. *Journal of Molecular Biology* 2003 332(2):489-503
Coppieters et al 2006 *Arthritis & Rheumatism* 54(6):1856-1866
Chomezynnski et al *Anal Biochem* 1987 162:156-159
Desmet et al 2014 *Nature Communications* 5:5237
Ebersbach et al. *J. Mol. Biol.* 372 (1): 172-185
Ellis et al *Br J Clin Pharmacol.* 2019 85(2): 304-315
Faisst et al *J Virol* 1995 69:4538-4543
Fornasa et al *J Allergy Clin Immunol.* 2015 136(2):413-422
Frenken et al *J Biotech* 2000 78:11-21
Goldberg et al 2016 *Protein Eng Des Sel.* 29(12):563-572
Green and Sambrook *Molecular Cloning: A Laboratory Manual* 2012 4$^{th}$ Edition Cold Spring Harbour Laboratory Press
Grabulovski 2007 *J Biol Chem.* 282(5):3196-3204
Griffiths et al *Antibodies* 2013 2:66-81
Grundstrom et al 1985 *Nucl. Acids Res* 13:3305-3316
Hamers-Casterman et al *Nature* 1993 363(6428):446-448
Harmsen et al *Gene* 1993 125:115-123
Harmsen et al *Appl Microbiol Biotechnol* 2007 77(1):13-22)
Hendrickson et al *Clin Microbiol Rev* 2002 15(1):79-94
Hoogenboom et al *Nucl Acid Res* 1991 19:4133-4137
Humphreys and Wilson 1999 *Cytokine* 11(10):773-782
Huse et al *Science* 1989 246 (4935):1275-1281
Johnson et al 2012 *Anal. Chem.* 84(15):6553-6560
Kabat et al Sequences of Proteins of Immunological Interest, *Fifth Edition U.S. Department of*
Health and Human Services, 1991 NIH Publication Number 91-3242
Knezevic et al *J. Am. Chem. Soc.* 2012, 134(37):15225-15228
Köhler et al *Nature* 1975 256:495-497
Koide and Koide 2007 *Methods Mol. Biol.* 352: 95-109
Krehenbrink et al 2008 *J. Mol. Biol.* 383 (5):1058-1068.
Ling et al *Anal Biochem* 1997 254(2):157-178
Lipovsek 2011 *Protein Eng Des Sel.* 24(1-2):3-9
McCoy et al *Retrovirology* 2014 11:83
Merchlinsky et al *J. Virol.* 1983 47:227-232
Miethe et al *J Biotech* 2013 163(2):105-111
Muyldermans et al *Protein Eng* 1994 7(9):1129-1135
Muyldermans *Annu Rev Biochem* 2013 82:775-797
Nambiar et al *Science* 1984 223:1299-1301
Nelson et al *Molecular Pathology* 2000 53(3):111-117
Nguyen et al *Adv Immunol* 2001 79:261-296
Nixon and Wood 2006 *Curr Opin Drug Discov Devel.* 9(2):261-268
Nygren *FEBS J.* 2008 275(11):2668-76

Ortonne, Brit *J Dermatol* 1999 140 (suppl 54):1-7

Padlan *Mol Immunol* 1994 31:169-217

Rose-John *Int J Biol Sci.* 2012; 8(9):1237-47

Roux et al *Proc Natl Acad Sci USA* 1998 95:11804-11809

Sakamar et al *Nucl. Acids Res* 1988 14:6361-6372

Silverman et al 2005 *Nat. Biotechnol.* 23(12):1556-1561

Skerra et al *Science* 1988 240(4855):1038-1041

Skerra et al 2008 *FEBS J.* 275 (11): 2677-83

Suderman 2017 *Protein Expression and Purification* 134: 114-124

Tanha et al *J Immunol Methods* 2002 263:97-109

Thomassen et al *Enzyme and Micro Tech* 2002 30:273-278

Tsilingiri et al *Cell Mol Gastroenterol Hepatol.* 2017 3(2): 174-182

Verma et al *Annu Rev Biochem* 1998 67:99-134

Verstraete et al *Nat Commun.* 2017 8:14937. doi: 10.1038/ ncomms14937

Ward et al *Nature* 1989 341:544-546

---

The invention claimed is:

1. A composition comprising a TNF-alpha binding polypeptide and an IL-7R binding polypeptide, wherein:
   (a) the IL-7R binding polypeptide comprises three complementarity determining regions (CDR1-CDR3), wherein CDR1 comprises the amino acid sequence set forth in SEQ ID NO: 9, CDR2 comprises the amino acid sequence set forth in SEQ ID NO: 10 and CDR3 comprises the amino acid sequence set forth in SEQ ID NO: 11; and
   (b) the TNF-alpha binding polypeptide comprises three complementarity determining regions (CDR1-CDR3), wherein CDR1 comprises the amino acid sequence set forth in SEQ ID NO: 1, CDR2 comprises the amino acid sequence set forth in SEQ ID NO: 2, and CDR3 comprises the amino acid sequence set forth in SEQ ID NO: 3.

2. The composition according to claim 1, wherein the TNF-alpha binding polypeptide and the IL-7R binding polypeptide are antibodies or antibody fragments.

3. The composition according to claim 2, wherein the TNF-alpha binding polypeptide and the IL-7R binding polypeptide each comprise or consist of an immunoglobulin chain variable domain.

4. The composition according to claim 3, wherein the TNF-alpha binding polypeptide and the IL-7R binding polypeptide each comprise a VHH.

5. The composition according to claim 1, wherein the TNF-alpha binding polypeptide neutralizes human TNF-alpha cytotoxicity in an L929 assay with an EC50 of 100 nM or less, and the IL-7R binding polypeptide neutralizes IL-7R-dependent, IL-7-induced STAT5 phosphorylation in human lymphocytes with an EC50 of 100 nM or less.

6. The composition according to claim 1, wherein:
   (a) the TNF-alpha binding polypeptide comprises or consists of a sequence sharing at least 90% identity to SEQ ID NO: 8; and (b) the IL-7R binding polypeptide comprises or consists of a sequence sharing at least 90% identity to SEQ ID NO: 16.

7. The composition according to claim 6, wherein:
   (a) the TNF-alpha binding polypeptide comprises SEQ ID NO: 8; and
   (b) the IL-7R binding polypeptide comprises SEQ ID NO: 16.

8. The composition according to claim 7, wherein the TNF-alpha binding polypeptide and the IL-7R binding polypeptide are coupled by a protease-labile peptide linker.

9. The composition according to claim 8, wherein the protease-labile linker comprises or consists of the sequence set forth in SEQ ID NO: 34 comprising the format -(G$_4$S)$_x$-K-(G$_4$S)$_y$-, wherein x and y are each independently 1 to 5.

10. The composition according to claim 9, wherein the protease-labile linker comprises or consists of the sequence set forth in SEQ ID NO: 33 comprising the format [-(GaS)x-B-(GbS)y-] z, wherein:
   a is 1 to 10;
   b is 1 to 10;
   x is 1 to 10;
   y is 1 to 10;
   z is 1 to 10; and
   B is K or R.

11. The composition according to claim 10, wherein the polypeptides are substantially resistant to one or more proteases present in the small or large intestine, wherein the one or more proteases are trypsin or chymotrypsin.

12. The composition according to claim 8, wherein the protease-labile linker comprises of the sequence set forth in SEQ ID NO: 21.

13. The composition according to claim 8, wherein the protease-labile linker consists of the sequence set forth in SEQ ID NO: 21.

14. A pharmaceutical composition comprising the TNF-alpha binding polypeptide and the IL-7R binding polypeptide according to claim 1 and a pharmaceutically acceptable excipient.

15. The composition according to claim 1, wherein the TNF-alpha binding polypeptide and the IL-7R binding polypeptide comprises a polypeptide comprising an amino acid sequence at least 90% identical to that set forth in SEQ ID NO: 26.

16. The composition according to claim 1, wherein the TNF-alpha binding polypeptide and the IL-7R binding polypeptide comprises a polypeptide comprising an amino acid sequence set forth in SEQ ID NO: 26.

17. A pharmaceutical composition comprising a polypeptide comprising an amino acid sequence set forth in SEQ ID NO: 26 and a pharmaceutically acceptable excipient.

18. A method of treating or preventing autoimmune disease and/or inflammatory disease comprising administering to a person in need thereof a composition according to claim 1.

19. The method according to claim 18, wherein the autoimmune and/or inflammatory disease is inflammatory bowel disease and/or mucositis.

20. The method according to claim 18, wherein the autoimmune and/or inflammatory disease is atopic dermatitis.

21. The method according to claim 18, wherein the composition is for use in oral administration.

22. The method according to claim 18, wherein the composition is for use in topical administration.

* * * * *

SEQUENCE LISTING

```
<160> NUMBER OF SEQ ID NOS: 43

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Ser His Trp Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 2

Glu Ile Asn Thr Asn Gly Leu Ile Thr His Tyr Gly Asp Ser Val Lys
1               5                   10                  15

Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 3

Asn Gln His Gly Leu Asn
1               5

<210> SEQ ID NO 4
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 4

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence
```

-continued

<400> SEQUENCE: 5

Trp Val Arg Gln Ala Pro Gly Lys Glu Leu Glu Trp Leu Ser
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 6

Arg Phe Thr Val Ser Arg Asn Asn Ala Ala Asn Lys Met Tyr Leu Glu
1               5                   10                  15

Leu Thr Arg Leu Glu Pro Glu Asp Thr Ala Leu Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 7

Lys Gly Gln Gly Thr Gln Val Thr Val Ser Ser
1               5                   10

<210> SEQ ID NO 8
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 8

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
    50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
            100                 105                 110

Val Ser Ser
        115

<210> SEQ ID NO 9
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 9

Ser Asp Ala Met Gly
1            5

<210> SEQ ID NO 10
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 10

Ala Ile Gly Trp Ser Gly Ala Val Thr His Tyr Ser Asp Ser Val Lys
1            5                10              15

Gly

<210> SEQ ID NO 11
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 11

Asp Tyr Asp Thr Asp Val Trp Gln Tyr
1            5

<210> SEQ ID NO 12
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 12

Asp Val Gln Leu Val Glu Ser Gly Gly Gly Leu Val Gln Ala Gly Gly
1            5                10              15

Ser Leu Arg Leu Ser Cys Glu Ser Ser Ile Ser Thr Phe Ser
          20             25            30

<210> SEQ ID NO 13
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 13

Trp Phe Arg Gln Ala Pro Gly Lys Glu Leu Glu Phe Leu Ala
1            5                10

<210> SEQ ID NO 14
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 14

Arg Phe Thr Ile Ser Arg Asp Asn Ala Lys Asn Thr Val Tyr Leu Gln
1            5                10              15

Met Asn Ser Leu Arg Ala Glu Asp Thr Gly Arg Tyr Tyr Cys Ala Glu
          20             25           30

<210> SEQ ID NO 15
<211> LENGTH: 11

<212> TYPE: PRT
<213> ORGANISM: Artificial Sequence
<220> FEATURE:
<223> OTHER INFORMATION: Synthetic Sequence

<400> SEQUENCE: 15

Trp Gly Gln Gly Thr Gln Val Thr Val Ser Ser
1               5                   10

<210> SEQ ID NO 16
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 16

Asp Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
            20                  25                  30

Ala Met Gly Trp Phe Arg Gln Ala Pro Gly Lys Glu Leu Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
            100                 105                 110

Gln Val Thr Val Ser Ser
        115

<210> SEQ ID NO 17
<211> LENGTH: 351
<212> TYPE: DNA
<213> ORGANISM: Artificial Sequence
<220> FEATURE:
<223> OTHER INFORMATION: Synthetic Sequence

<400> SEQUENCE: 17
gatgttcaat tggttgaatc tggtggtggt ttggttcaac caggtggttc tttgaaattg        60
tcttgtgctg cttctggttt cgatttctct tctcattgga tgtactgggt tagacaagct       120
ccaggtaaag aattggaatg gttgtctgaa atcaacacca cggtttgat tacccattat        180 ggtgattctg tcaagggtag attcactgtc tctagaaaca atgctgctaa caagatgtac       240
ttggaattga ccagattgga accagaagat actgccttgt attactgcgc tagaaatcaa       300
catggtttga caaaggtca aggtactcaa gttaccgttt cctcataatg a                  351

<210> SEQ ID NO 18
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 18
gatgttcaat tggttgaatc tggtggtggt ttggttcaag ccggtggttc tttgagattg        60
tcttgtgaat cttctatctc caccttctca tctgatgcta tgggttggtt tagacaagct       120

```
ccaggtaaag aattggaatt tttggctgct attggttgga gtggtgctgt tactcattat    180
tccgattctg ttaaaggtcg tttcaccatt tctagagata acgctaagaa caccgtctac    240
ttgcaaatga actctttgag agctgaagat accggtagat attactgcgc tgaagattac    300
gatactgatg tttggcaata ttggggtcaa ggtactcaag ttactgtctc ctcatgataa    360
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 19

Asp Asp Asp Asp Lys
1               5
```

```
<210> SEQ ID NO 20
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 20

Gly Gly Gly Gly Ser Asp Asp Asp Asp Lys Gly Gly Gly Gly Ser
1               5                  10                  15
```

```
<210> SEQ ID NO 21
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 21

Gly Gly Gly Gly Ser Gly Gly Gly Gly Ser Lys Gly Gly Gly Gly Ser
1               5                  10                  15

Gly Gly Gly Gly Ser
            20
```

```
<210> SEQ ID NO 22
<211> LENGTH: 159
<212> TYPE: PRT
<213> ORGANISM: Homo sapiens

<400> SEQUENCE: 22

Met Phe Pro Phe Ala Leu Leu Tyr Val Leu Ser Val Ser Phe Arg Lys
1               5                  10                  15

Ile Phe Ile Leu Gln Leu Val Gly Leu Val Leu Thr Tyr Asp Phe Thr
                20                  25                  30

Asn Cys Asp Phe Glu Lys Ile Lys Ala Ala Tyr Leu Ser Thr Ile Ser
            35                  40                  45

Lys Asp Leu Ile Thr Tyr Met Ser Gly Thr Lys Ser Thr Glu Phe Asn
        50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110
```

```
Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155
```

```
<210> SEQ ID NO 23
<211> LENGTH: 63
<212> TYPE: PRT
<213> ORGANISM: Homo sapiens

<400> SEQUENCE: 23

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
                20                  25                  30

Lys Arg Lys Val Thr Thr Asn Lys Cys Leu Glu Gln Val Ser Gln Leu
        35                  40                  45

Gln Gly Leu Trp Arg Arg Phe Asn Arg Pro Leu Leu Lys Gln Gln
    50                  55                  60
```

```
<210> SEQ ID NO 24
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 24

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
                20                  25                  30

Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
        115
```

```
<210> SEQ ID NO 25
<211> LENGTH: 118
<212> TYPE: PRT
<213> ORGANISM: Artificial Sequence
<220> FEATURE:
<223> OTHER INFORMATION: Synthetic Sequence

<400> SEQUENCE: 25

Glu Val Gln Leu Val Glu Ser Gly Gly Gly Leu Val Gln Ala Gly Gly
1               5                   10                  15

Ser Leu Arg Leu Ser Cys Glu Ser Ser Ile Ser Thr Phe Ser Ser Asp
                20                  25                  30
```

-continued

```
Ala Met Gly Trp Phe Arg Gln Ala Pro Gly Lys Glu Arg Glu Phe Leu
        35                  40                  45

Ala Ala Ile Gly Trp Ser Gly Ala Val Thr His Tyr Ser Asp Ser Val
        50                  55                  60

Gln Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Gly Arg Tyr Tyr Cys
                85                  90                  95

Ala Glu Asp Tyr Asp Thr Asp Val Trp Gln Tyr Trp Gly Gln Gly Thr
                100                 105                 110

Gln Val Thr Val Ser Ser
        115

<210> SEQ ID NO 26
<211> LENGTH: 254
<212> TYPE: PRT
<213> ORGANISM: Artificial sequence
<220> FEATURE:
<223> OTHER INFORMATION: Synthetic Sequence

<400> SEQUENCE: 26

Asp Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
        20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
        50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
                85                  90                  95

Ala Arg Asn Gln His Gly Leu Asn Lys Gly Gln Gly Thr Gln Val Thr
                100                 105                 110

Val Ser Ser Gly Gly Gly Gly Ser Gly Gly Gly Ser Lys Gly Gly
        115                 120                 125

Gly Gly Ser Gly Gly Gly Gly Ser Glu Val Gln Leu Val Glu Ser Gly
        130                 135                 140

Gly Gly Leu Val Gln Ala Gly Gly Ser Leu Arg Leu Ser Cys Glu Ser
145                 150                 155                 160

Ser Ile Ser Thr Phe Ser Ser Asp Ala Met Gly Trp Phe Arg Gln Ala
                165                 170                 175

Pro Gly Lys Glu Leu Glu Phe Leu Ala Ala Ile Gly Trp Ser Gly Ala
                180                 185                 190

Val Thr His Tyr Ser Asp Ser Val Lys Gly Arg Phe Thr Ile Ser Arg
                195                 200                 205

Asp Asn Ala Lys Asn Thr Val Tyr Leu Gln Met Asn Ser Leu Arg Ala
        210                 215                 220

Glu Asp Thr Gly Arg Tyr Tyr Cys Ala Glu Asp Tyr Asp Thr Asp Val
225                 230                 235                 240

Trp Gln Tyr Trp Gly Gln Gly Thr Gln Val Thr Val Ser Ser
                245                 250

<210> SEQ ID NO 27
```

```
<211> LENGTH: 768
<212> TYPE: DNA
<213> ORGANISM: Artificial Sequence
<220> FEATURE:
<223> OTHER INFORMATION: Synthetic Sequence

<400> SEQUENCE: 27
gatgttcaat tggttgaatc tggtggtggt ttggttcaac caggtggttc tttgaaattg        60
tcttgtgctg cttctggttt cgatttctct tctcattgga tgtactgggt tagacaagct       120
ccaggtaaag aattggaatg gttgtctgaa atcaacacca acggtttgat tacccattat       180
ggtgattctg tcaagggtag attcactgtc tctagaaaca atgctgctaa caagatgtac       240
ttggaattga ccagattgga accagaagat actgccttgt attactgcgc tagaaatcag       300
catggtttga acaaaggtca aggtactcaa gttactgttt cttctggtgg aggcggttca       360
ggcggaggtg gctctaaggg cggtggcgga agtggtggag cgggttcaga agttcaatta       420
gttgagagtg gtggcggttt agtacaagct ggtggttcat taagattgtc ctgcgaatct       480
tctatctcca ccttttcatc tgatgctatg ggttggttca gacaagcacc tggaaaagag       540
ttagaattct tggctgctat tggttggagt ggtgctgtta ctcattactc tgattcagtt       600
aagggtcgtt tcaccatctc aagagataat gctaagaaca ccgtctactt gcagatgaat       660
tctttgagag ctgaagatac aggtaggtac tattgtgctg aagattacga tactgatgtc       720
tggcaatatt ggggacaagg cacccaagtt acagttagtt cttaatga              768
```

```
<210> SEQ ID NO 28
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is Ser or Asp

<400> SEQUENCE: 28

Xaa Asp Ala Met Gly
1               5
```

```
<210> SEQ ID NO 29
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa is Ile or Thr
<220> FEATURE:
<221> NAME/KEY: MISC_FEATURE
<222> LOCATION: (3)..(3)
<223> OTHER INFORMATION: Xaa is Gly or Asn
<220> FEATURE:
<221> NAME/KEY: MISC_FEATURE
<222> LOCATION: (7)..(7)
<223> OTHER INFORMATION: Xaa is Ala or Thr
<220> FEATURE:
<221> NAME/KEY: MISC_FEATURE
<222> LOCATION: (12)..(12)
<223> OTHER INFORMATION: Xaa is Ser or Gly
<220> FEATURE:
<221> NAME/KEY: MISC_FEATURE
<222> LOCATION: (16)..(16)
<223> OTHER INFORMATION: Xaa is Gln or Lys
```

```
<400> SEQUENCE: 29

Ala Xaa Xaa Trp Ser Gly Xaa Val Thr His Tyr Xaa Asp Ser Val Xaa
1               5                   10                  15

Gly

<210> SEQ ID NO 30
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (3)..(3)
<223> OTHER INFORMATION: Xaa is Asp or Val
<220> FEATURE:
<221> NAME/KEY: MISC_FEATURE
<222> LOCATION: (9)..(9)
<223> OTHER INFORMATION: Xaa is Tyr or His

<400> SEQUENCE: 30

Asp Tyr Xaa Thr Asp Val Trp Gln Xaa
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(15)
<223> OTHER INFORMATION: Said residues may be present 1 to 15 times
<220> FEATURE:
<221> NAME/KEY: VARIANT
<222> LOCATION: (2)..(10)
<223> OTHER INFORMATION: None, some or all of said Gly residues may be
      present
<220> FEATURE:
<221> NAME/KEY: VARIANT
<222> LOCATION: (12)..(15)
<223> OTHER INFORMATION: None, some or all of said Ser residues may be
      present

<400> SEQUENCE: 31

Gly Gly Gly Gly Gly Gly Gly Gly Gly Gly Ser Ser Ser Ser Ser
1               5                   10                  15

<210> SEQ ID NO 32
<211> LENGTH: 5
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(5)
<223> OTHER INFORMATION: Said residues  may be present 1 to 8 times

<400> SEQUENCE: 32

Gly Gly Gly Gly Ser
1               5

<210> SEQ ID NO 33
<211> LENGTH: 65
<212> TYPE: PRT
<213> ORGANISM: Artificial Sequence
<220> FEATURE:
<223> OTHER INFORMATION: Synthetic Sequence
```

```
<220> FEATURE:
<221> NAME/KEY: VARIANT
<222> LOCATION: (1)..(65)
<223> OTHER INFORMATION: Said residues may be present 1 to 5 times
<220> FEATURE:
<221> NAME/KEY: VARIANT
<222> LOCATION: (1)..(15)
<223> OTHER INFORMATION: Said residues may be present 0 to 10 times
<220> FEATURE:
<221> NAME/KEY: VARIANT
<222> LOCATION: (2)..(10)
<223> OTHER INFORMATION: None, some, or all of said Gly residues may be
      present
<220> FEATURE:
<221> NAME/KEY: VARIANT
<222> LOCATION: (12)..(15)
<223> OTHER INFORMATION: None, some, or all of said Ser residues may be
      present
<220> FEATURE:
<221> NAME/KEY: VARIANT
<222> LOCATION: (16)..(30)
<223> OTHER INFORMATION: Said residues may be present 0 to 10 times
<220> FEATURE:
<221> NAME/KEY: VARIANT
<222> LOCATION: (17)..(25)
<223> OTHER INFORMATION: None, some, or all of said Gly residues may be
      present
<220> FEATURE:
<221> NAME/KEY: VARIANT
<222> LOCATION: (27)..(30)
<223> OTHER INFORMATION: None, some, or all of said Ser residues may be
      present
<220> FEATURE:
<221> NAME/KEY: MISC_FEATURE
<222> LOCATION: (31)..(35)
<223> OTHER INFORMATION: Xaa is Lys or Arg
<220> FEATURE:
<221> NAME/KEY: VARIANT
<222> LOCATION: (32)..(35)
<223> OTHER INFORMATION: None, some, or all of said Xaa residues may be
      present
<220> FEATURE:
<221> NAME/KEY: VARIANT
<222> LOCATION: (36)..(50)
<223> OTHER INFORMATION: Said residues may be present 0 to 10 times
<220> FEATURE:
<221> NAME/KEY: VARIANT
<222> LOCATION: (37)..(45)
<223> OTHER INFORMATION: None, some, or all of said Gly residues may be
      present
<220> FEATURE:
<221> NAME/KEY: VARIANT
<222> LOCATION: (47)..(50)
<223> OTHER INFORMATION: None, some, or all of said Ser residues may be
      present
<220> FEATURE:
<221> NAME/KEY: VARIANT
<222> LOCATION: (51)..(65)
<223> OTHER INFORMATION: Said residues may be present 0 to 10 times
<220> FEATURE:
<221> NAME/KEY: VARIANT
<222> LOCATION: (52)..(60)
<223> OTHER INFORMATION: None, some, or all of said Gly residues may be
      present
<220> FEATURE:
<221> NAME/KEY: VARIANT
<222> LOCATION: (62)..(65)
<223> OTHER INFORMATION: None, some, or all of said Ser residues may be
      present

<400> SEQUENCE: 33

Gly Gly Gly Gly Gly Gly Gly Gly Gly Gly Ser Ser Ser Ser Ser Gly
1               5                   10                  15

Gly Gly Gly Gly Gly Gly Gly Gly Gly Ser Ser Ser Ser Ser Xaa Xaa
            20                  25                  30

Xaa Xaa Xaa Gly Gly Gly Gly Gly Gly Gly Gly Gly Gly Ser Ser Ser
```

```
            35                  40                  45
Ser Ser Gly Gly Gly Gly Gly Gly Gly Gly Gly Ser Ser Ser Ser
    50                  55                  60

Ser
65
```

```
<210> SEQ ID NO 34
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(5)
<223> OTHER INFORMATION: Said residues may be present 1 to 5 times
<220> FEATURE:
<221> NAME/KEY: VARIANT
<222> LOCATION: (7)..(11)
<223> OTHER INFORMATION: Said residues may be present 1 to 5 times

<400> SEQUENCE: 34

Gly Gly Gly Gly Ser Lys Gly Gly Gly Gly Ser
1               5                   10
```

```
<210> SEQ ID NO 35
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: VARIANT
<222> LOCATION: (2)..(12)
<223> OTHER INFORMATION: Said residues may be present 1 to 10 times
<220> FEATURE:
<221> NAME/KEY: VARIANT
<222> LOCATION: (3)..(11)
<223> OTHER INFORMATION: None, some, or all of said Gly residues may be
      present
<220> FEATURE:
<221> NAME/KEY: MISC_FEATURE
<222> LOCATION: (13)..(13)
<223> OTHER INFORMATION: Xaa is Lys or Arg

<400> SEQUENCE: 35

Xaa Gly Gly Gly Gly Gly Gly Gly Gly Gly Gly Ser Xaa
1               5                   10
```

```
<210> SEQ ID NO 36
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 36

Lys Gly Gly Gly Gly Ser Gly Gly Gly Gly Ser Lys
1               5                   10
```

```
<210> SEQ ID NO 37
<211> LENGTH: 11
<212> TYPE: PRT
<213> ORGANISM: Artificial Sequence
<220> FEATURE:
<223> OTHER INFORMATION: Synthetic Sequence
```

```
<400> SEQUENCE: 37

Gly Gly Gly Gly Ser Gly Gly Gly Gly Ser Lys
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 38

Lys Gly Gly Gly Gly Ser Gly Gly Gly Gly Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 39

Arg Gly Gly Gly Gly Ser Gly Gly Gly Gly Ser Arg
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 40

Gly Gly Gly Gly Ser Gly Gly Gly Gly Ser Arg
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 41

Arg Gly Gly Gly Gly Ser Gly Gly Gly Gly Ser
1               5                   10

<210> SEQ ID NO 42
<211> LENGTH: 25
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is Lys or Arg
<220> FEATURE:
<221> NAME/KEY: VARIANT
<222> LOCATION: (2)..(12)
<223> OTHER INFORMATION: Said residues may be present 1 to 10 times
<220> FEATURE:
<221> NAME/KEY: VARIANT
<222> LOCATION: (3)..(11)
<223> OTHER INFORMATION: None, some, or all of said Gly residues may be
      present
<220> FEATURE:
```

```
<221> NAME/KEY: MISC_FEATURE
<222> LOCATION: (13)..(13)
<223> OTHER INFORMATION: Xaa is Lys or Arg
<220> FEATURE:
<221> NAME/KEY: VARIANT
<222> LOCATION: (14)..(24)
<223> OTHER INFORMATION: Said residues may be present 1 to 10 times
<220> FEATURE:
<221> NAME/KEY: VARIANT
<222> LOCATION: (15)..(23)
<223> OTHER INFORMATION: None, some, or all of said Gly residues may be
      present
<220> FEATURE:
<221> NAME/KEY: MISC_FEATURE
<222> LOCATION: (25)..(25)
<223> OTHER INFORMATION: Xaa is Lys or Arg

<400> SEQUENCE: 42

Xaa Gly Gly Gly Gly Gly Gly Gly Gly Gly Gly Ser Xaa Gly Gly Gly
1               5                   10                  15

Gly Gly Gly Gly Gly Gly Gly Ser Xaa
            20                  25

<210> SEQ ID NO 43
<211> LENGTH: 61
<212> TYPE: PRT
<213> ORGANISM: Artificial Sequence
<220> FEATURE:
<223> OTHER INFORMATION: Synthetic Sequence
<220> FEATURE:
<221> NAME/KEY: VARIANT
<222> LOCATION: (1)..(61)
<223> OTHER INFORMATION: Said residues may be present 1 to 5 times
<220> FEATURE:
<221> NAME/KEY: VARIANT
<222> LOCATION: (1)..(15)
<223> OTHER INFORMATION: Said residues may be present 0 to 10 times
<220> FEATURE:
<221> NAME/KEY: VARIANT
<222> LOCATION: (2)..(10)
<223> OTHER INFORMATION: None, some, or all of said Gly residues may be
      present
<220> FEATURE:
<221> NAME/KEY: VARIANT
<222> LOCATION: (12)..(15)
<223> OTHER INFORMATION: None, some, or all of said Ser residues may be
      present
<220> FEATURE:
<221> NAME/KEY: VARIANT
<222> LOCATION: (16)..(30)
<223> OTHER INFORMATION: Said residues may be present 0 to 10 times
<220> FEATURE:
<221> NAME/KEY: VARIANT
<222> LOCATION: (17)..(25)
<223> OTHER INFORMATION: None, some, or all of said Gly residues may be
      present
<220> FEATURE:
<221> NAME/KEY: VARIANT
<222> LOCATION: (27)..(30)
<223> OTHER INFORMATION: None, some, or all of said Ser residues may be
      present
<220> FEATURE:
<221> NAME/KEY: MISC_FEATURE
<222> LOCATION: (31)..(31)
<223> OTHER INFORMATION: Xaa is 1 to 5 residues selected from Trp, Phe,
      Tyr, Leu and Met
<220> FEATURE:
<221> NAME/KEY: VARIANT
<222> LOCATION: (32)..(46)
<223> OTHER INFORMATION: Said residues may be present 0 to 10 times
<220> FEATURE:
<221> NAME/KEY: VARIANT
<222> LOCATION: (33)..(41)
<223> OTHER INFORMATION: None, some, or all of said Gly residues may be
      present
<220> FEATURE:
```

-continued

```
<221> NAME/KEY: VARIANT
<222> LOCATION: (43)..(46)
<223> OTHER INFORMATION: None, some, or all of said Ser residues may be
      present
<220> FEATURE:
<221> NAME/KEY: VARIANT
<222> LOCATION: (47)..(61)
<223> OTHER INFORMATION: Said residues may be present 0 to 10 times
<220> FEATURE:
<221> NAME/KEY: VARIANT
<222> LOCATION: (48)..(56)
<223> OTHER INFORMATION: None, some, or all of said Gly residues may be
      present
<220> FEATURE:
<221> NAME/KEY: VARIANT
<222> LOCATION: (58)..(61)
<223> OTHER INFORMATION: None, some, or all of said Ser residues may be
      present

<400> SEQUENCE: 43

Gly Gly Gly Gly Gly Gly Gly Gly Gly Gly Ser Ser Ser Ser Ser Gly
1               5                   10              15

Gly Gly Gly Gly Gly Gly Gly Gly Gly Ser Ser Ser Ser Ser Xaa Gly
            20                  25              30

Gly Gly Gly Gly Gly Gly Gly Gly Gly Ser Ser Ser Ser Ser Gly Gly
        35                  40                  45

Gly Gly Gly Gly Gly Gly Gly Gly Ser Ser Ser Ser Ser
    50                  55              60
```